(12) United States Patent
Wittek et al.

(10) Patent No.: US 9,315,729 B2
(45) Date of Patent: Apr. 19, 2016

(54) POLYMERIZABLE COMPOUNDS AND THEIR USE IN LIQUID CRYSTAL MEDIA AND LIQUID CRYSTAL DISPLAYS

(75) Inventors: Michael Wittek, Erzhausen (DE); Norihiko Tanaka, Darmstadt (DE); Andreas Taugerbeck, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 81 days.

(21) Appl. No.: 14/122,333

(22) PCT Filed: May 15, 2012

(86) PCT No.: PCT/EP2012/002078
§ 371 (c)(1),
(2), (4) Date: Nov. 26, 2013

(87) PCT Pub. No.: WO2012/163478
PCT Pub. Date: Dec. 6, 2012

(65) Prior Publication Data
US 2014/0125938 A1    May 8, 2014

(30) Foreign Application Priority Data

May 27, 2011    (DE) .......................... 10 2011 102 592

(51) Int. Cl.
| | |
|---|---|
| *C07C 22/08* | (2006.01) |
| *C07C 25/13* | (2006.01) |
| *C07C 25/18* | (2006.01) |
| *C07C 25/24* | (2006.01) |
| *C09K 19/12* | (2006.01) |
| *C09K 19/54* | (2006.01) |
| *C09K 19/52* | (2006.01) |
| *C09K 19/02* | (2006.01) |
| *C09K 19/20* | (2006.01) |
| *C09K 19/34* | (2006.01) |
| *C09K 19/46* | (2006.01) |
| *C08F 120/30* | (2006.01) |
| *C08F 122/26* | (2006.01) |
| *C09K 19/04* | (2006.01) |

(52) U.S. Cl.
CPC ............... *C09K 19/542* (2013.01); *C07C 22/08* (2013.01); *C07C 25/13* (2013.01); *C07C 25/18* (2013.01); *C07C 25/24* (2013.01); *C08F 120/30* (2013.01); *C08F 122/26* (2013.01); *C09K 19/0275* (2013.01); *C09K 19/20* (2013.01); *C09K 19/3402* (2013.01); *C09K 19/46* (2013.01); *C09K 2019/0448* (2013.01); *C09K 2019/0466* (2013.01); *C09K 2019/2042* (2013.01)

(58) Field of Classification Search
CPC ...... C07C 69/602; C07C 22/08; C07C 25/13; C07C 25/18; C07C 25/24; C09K 19/0275; C09K 19/20; C09K 19/46; C09K 19/542; C09K 2019/0448; C09K 2019/0466
See application file for complete search history.

(56) References Cited

U.S. PATENT DOCUMENTS

| | | |
|---|---|---|
| 8,895,117 B2 | 11/2014 | Jansen et al. |
| 2004/0011996 A1 | 1/2004 | Klasen-Memmer et al. |
| 2009/0059132 A1 | 3/2009 | Yamamoto et al. |
| 2009/0109392 A1 | 4/2009 | Hsieh et al. |
| 2009/0268143 A1 | 10/2009 | Takeuchi et al. |
| 2010/0078593 A1 | 4/2010 | Takeuchi et al. |
| 2010/0103366 A1 | 4/2010 | Farrand et al. |
| 2011/0261311 A1 | 10/2011 | Jansen et al. |
| 2014/0158934 A1* | 6/2014 | Wittek et al. ............ 252/299.61 |
| 2014/0362334 A1 | 12/2014 | Jansen et al. |

FOREIGN PATENT DOCUMENTS

| | | |
|---|---|---|
| CN | 102241988 A | 11/2011 |
| WO | 2008/061606 A1 | 5/2008 |

OTHER PUBLICATIONS

International Search Report dated Jun. 22, 2012 issued in corresponding PCT/EP2012/002078 application (pp. 1-2).
Chinese Office Action dated Sep. 28, 2014 issued in corresponding CN 201280025759.4 application (pp. 1-7).
English Translation of the Chinese Office Action dated Sep. 28, 2014 issued in corresponding CN 201280025759.4 application (pp. 1-9).
English Translation Abstract of CN 102241988 A published Nov. 16, 2011.

* cited by examiner

*Primary Examiner* — Shean C Wu
(74) *Attorney, Agent, or Firm* — Miller, White, Zelano, Branigan, P.C.

(57) ABSTRACT

The present invention relates to polymerizable compounds, liquid-crystalline media comprising the compounds, in particular liquid-crystal (LC) media and LC displays having a polymer-stabilised blue phase, and LC media for LC displays of the PS or PSA type ("polymer sustained" or "polymer sustained alignment") type.

29 Claims, No Drawings

POLYMERIZABLE COMPOUNDS AND THEIR USE IN LIQUID CRYSTAL MEDIA AND LIQUID CRYSTAL DISPLAYS

The present invention relates to polymerisable compounds, to liquid-crystalline media comprising the compounds, in particular liquid-crystal (LC) media and LC displays having a polymer-stabilised blue phase, and LC media for LC displays of the PS or PSA ("polymer sustained" or "polymer sustained alignment") type.

Media for display elements which operate in the liquid-crystalline blue phase (blue phase for short) are known from the prior art. Such displays are described, for example, in WO 2004/046805 A1 and WO 2008/061606 A1.

The blue phase is generally observed at the transition from the chiral nematic state to the optically isotropic state. The medium in the liquid-crystalline blue phase (blue; historical origin) is generally colourless for display use. The aim of efforts to date was to extend the temperature range of the blue phase from less than one degree to a range which is useful in practice (cf. H. Kikuchi et al., *Nature Materials* (2002), 1(1), 64-68; Kikuchi, H. et al., *Polymeric Materials Science and Engineering*, (2003), 89, 90-91).

For this purpose, it has been proposed in the prior art to add a polymerisable compound to the LC medium, and then to polymerise this compound in situ in the LC medium. The polymer or polymer network formed in the process is claimed to stabilise the blue phase.

The polymer-stabilised blue phases described to date in the prior art use, for example, a monoreactive non-mesogenic monomer together with a direactive mesogenic monomer as monomers.

WO 2005/080529 A1 describes, for example, polymer-stabilised blue phases comprising mono- and multireactive monomers.

The present invention was based on the object of finding suitable monomers and corresponding polymers for the stabilisation of blue phases. The polymer is intended, in particular, to have the following effects on the properties of the stabilised LC phase:
broad temperature range of the blue phase,
fast response time,
low operating voltage ($V_{op}$),
small variation of the operating voltage with temperature,
low hysteresis of the transmission of a cell when the operating voltage is changed in order to achieve defined grey shades.

In addition, monomers which are stable to exposure to light and temperature are required. Good solubility in LC materials or good miscibility with the LC medium is furthermore necessary in order to achieve a good distribution in the LC medium.

The present invention is thus based on the object of providing improved polymerisable compounds, and LC media comprising such compounds, in particular for use in LC displays having a polymer-stabilised blue phase. The polymerisable compounds according to the invention are intended to stabilise the blue phase. The LC media according to the invention are intended to have one or more improved properties, in particular selected from the properties mentioned above. In particular, the LC media are intended to have a broad blue phase, enable fast switching, have a good voltage holding ratio (VHR), require low voltages ($V_{op}$) for the switching process and exhibit low hysteresis ($\Delta V$) and have a low memory effect (ME). The LC media are intended to be stable to exposure to light and temperature.

Furthermore, so-called PS and PSA ("polymer sustained" and "polymer sustained alignment" respectively) displays, for which the term "polymer stabilised" is also occasionally used, are known from the prior art. In these displays, a small amount (for example 0.3% by weight, typically <1% by weight) of one or more polymerisable compound(s) is added to the LC medium and, after introduction into the LC cell, is polymerised or crosslinked in situ, usually by UV photopolymerisation, with or without an applied electrical voltage between the electrodes. The addition of polymerisable mesogenic or liquid-crystalline compounds, also known as reactive mesogens or "RMs", to the LC mixture has proven particularly suitable.

The term "PSA" is used below, unless indicated otherwise, as representative of PS displays and PSA displays.

In the meantime, the PS(A) principle is being used in diverse classical LC displays. Thus, for example, PSA-VA, PSA-OCB, PSA-IPS, PSA-FFS and PSA-TN displays are known. The polymerisation of the polymerisable compound(s) is preferably carried out with an applied electrical voltage in the case of PSA-VA and PSA-OCB displays and with or without an applied electrical voltage in the case of PSA-IPS displays. As can be shown in test cells, the PS(A) method results in a "pretilt" in the cell. In the case of PSA-OCB displays, for example, the bend structure can be stabilised, so that an offset voltage is unnecessary or can be reduced. In the case of PSA-VA displays, the pretilt has a positive effect on the response times. For PSA-VA displays, a standard MVA or PVA pixel and electrode layout can be used. In addition, however, only one structured electrode side and no protrusions, for example, are also sufficient, which significantly simplifies production and at the same time results in very good contrast at the same time as very good light transmission.

PSA-VA displays are described, for example, in JP 10-036847 A, EP 1 170 626 A2, U.S. Pat. Nos. 6,861,107, 7,169,449, US 2004/0191428 A1, US 2006/0066793 A1 and US 2006/0103804 A1. PSA-OCB displays are described, for example, in T.-J-Chen et al., Jpn. J. Appl. Phys. 45, 2006, 2702-2704 and S. H. Kim, L.-C-Chien, Jpn. J. Appl. Phys. 43, 2004, 7643-7647. PSA-IPS displays are described, for example, in U.S. Pat. No. 6,177,972 and Appl. Phys. Lett. 1999, 75(21), 3264. PSA-TN displays are described, for example, in Optics Express 2004, 12(7), 1221.

PSA displays, like the conventional LC displays described above, can be operated as active-matrix or passive-matrix displays. In the case of active-matrix displays, individual pixels are usually addressed by integrated, nonlinear, active elements, such as, for example, transistors (for example thin-film transistors or "TFTs"), while in the case of passive-matrix displays, the addressing is usually carried out by the multiplex method, both methods being known from the prior art.

However, not all combinations consisting of LC mixture and polymerisable component are suitable for PSA displays, since, for example, an inadequate tilt, or none at all, is established or since, for example, the so-called "voltage holding ratio" (VHR or HR) is inadequate for TFT display applications. In addition, it has been found that the LC mixtures and RMs known from the prior art still have some disadvantages on use in PSA displays. Thus, not every known RM which is soluble in LC mixtures is suitable for use in PSA displays.

In addition, the selected combination of LC host mixture/RM should have the lowest possible rotational viscosity and the best possible electrical properties. In particular, it should have the highest possible VHR. In the case of PSA displays, a high VHR after irradiation with UV light is particularly necessary since UV exposure is a necessary part of the display production process, but also occurs as normal exposure during operation of the finished display.

In particular, it would be desirable to have available novel materials for PSA displays which generate a particularly low pretilt angle. Preference is given here to materials which generate a lower pretilt angle during polymerisation for the same exposure time than the materials known to date, and/or whose use enables the (higher) pretilt angle that can be achieved with the known materials to be achieved already after a shorter exposure time. It is thus possible for the production time ("tact time") of the display to be shortened and for the costs of the production process to be reduced.

A further problem in the production of PSA displays is the presence or removal of residual amounts of unpolymerised RMs, in particular after the polymerisation step for generation of the pretilt angle in the display. For example, unreacted RMs of this type may adversely affect the properties of the display by polymerising in an uncontrolled manner, for example during operation after completion of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off, or after other pixels have been addressed.

It is therefore desirable for the polymerisation of the RMs during production of the PSA display to proceed as completely as possible and for the presence of unpolymerised RMs in the display to be excluded as far as possible or reduced to a minimum. To this end, materials which enable the most effective and complete polymerisation possible are required.

There is thus still a great demand for PSA displays and LC media and polymerisable compounds for use in such displays, which do not exhibit the disadvantages described above or only do so to a small extent and have improved properties. In addition, there is a great demand for PSA displays, and materials for use in PSA displays, which have advantageous properties, in particular facilitate a high specific resistance at the same time as a large working-temperature range, short response times, even at low temperatures, and a low threshold voltage, a low pretilt angle, a multiplicity of grey shades, high contrast and a broad viewing angle, and high values of the voltage holding ratio (VHR) after UV exposure and low-temperature stability, also known as "LTS", i.e. the stability of the LC mixture to individual components spontaneously crystallising out.

The invention is thus based on the further object of providing novel suitable materials, in particular RMs and LC media comprising them, for use in PSA displays, which do not have the disadvantages indicated above or only do so to a reduced extent, polymerise as quickly and completely as possible, enable a low pretilt angle to be established as quickly as possible, reduce or prevent the occurrence of image sticking in the display, and preferably at the same time facilitate very high specific resistance values, low threshold voltages and short response times. In addition, the LC media should have favourable LC phase properties and high VHR and LTS values.

The objects described above have been achieved in accordance with the invention by the provision of materials, processes and LC displays as described in the present application. In particular, it has been found, surprisingly, that the objects described above can be achieved in part or full by using LC media which comprise one or more polymerisable compounds according to the invention, as described below, for the production of such LC displays or by providing LC displays having a blue phase or PSA displays which contain one or more compounds according to the invention in polymerised form.

The polymerisable compounds according to the invention contain a central mesogenic group and at least two polymerisable groups which are linked to the mesogenic group directly or via spacer groups, where the central mesogenic group consists of two cyclic radicals which are linked to one another by a bridging group (for example —$CF_2O$— or —(CO)O—, etc.).

The use of the polymerisable compounds according to the invention in LC media according to the invention for LC displays having a polymer-stabilised blue phase results in significant stabilisation of the blue phase. In addition, it has been found, surprisingly, that a significant reduction in hysteresis ($\Delta V_{50}$) and an increase in contrast are achieved on use of the polymerisable compounds according to the invention in LC media having a polymer-stabilised blue phase, compared with polymerisable compounds and LC media as described in the prior art.

In PSA displays, the use of the polymerisable compounds according to the invention in LC media according to the invention results in the desired pretilt being achieved particularly quickly and in significantly shortened times during production of the display.

The prior art, such as, for example, U.S. Pat. No. 7,440,160 (WO 2004/046805 A1) and the documents cited therein, describes LC media for LC display elements which operate in the liquid-crystalline blue phase (blue phase for short). WO 2005/080529 A1 describes polymer-stabilised blue phases comprising mono- and multireactive monomers. US 2009/0267025 A1 (WO 2006/063662 A1), US 2009/051855 A1, US 2009/0059132 A1, US 2009/0059157 A1 and WO 2008/061606 A1 describe the polymer stabilisation of blue phases comprising liquid-crystalline reactive components (also known as reactive mesogens, "RMs" for short). In the publications mentioned above, however, preference is given to the use of RMs containing three phenyl radicals, such as, for example, the following RMs:

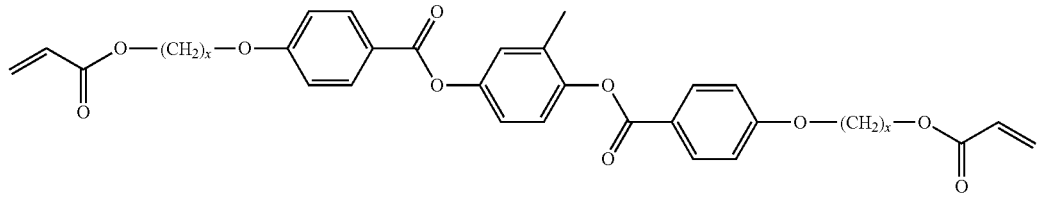

in which both x denote either 3 or 6.

However, the use of reactive components, which preferably consist of polymerisable compounds according to the invention, for polymer-stabilised blue phases or in PSA displays is neither described in nor obvious from the prior art.

U.S. Pat. No. 7,070,838 describes polymerisable compounds containing a 2-di- or -trifluoromethyl-1,4-phenyl ring, and the use thereof in polymerisable mixtures, LC polymers and LC displays having a cholesteric phase and in optical films. Specific compounds of a formula 1a-2-19 having the following structure are also disclosed therein:

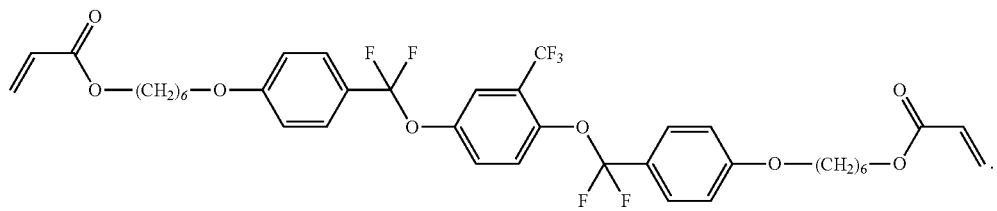

However, no properties of this compound on use in an LC display are disclosed. In addition, the use of compounds of this type for the stabilisation of blue phases or in PSA displays is neither described in nor obvious from U.S. Pat. No. 7,070,838.

JP 2005-015473 A discloses polymerisable compounds containing unsaturated spacer groups (alkynylene or alkenylene). Specific compounds of the formulae 1-13-77 to 1-13-84, 1-13-134, 1-13-135, 1-56-9, 1-56-10, 1-56-23, 1-56-24, which contain phenyl rings linked via $CF_2O$ bridges, and the use thereof for the production of optically anisotropic films and in ferroelectric LC media are also disclosed therein. Specific compounds, for example having the following structures, are also disclosed therein:

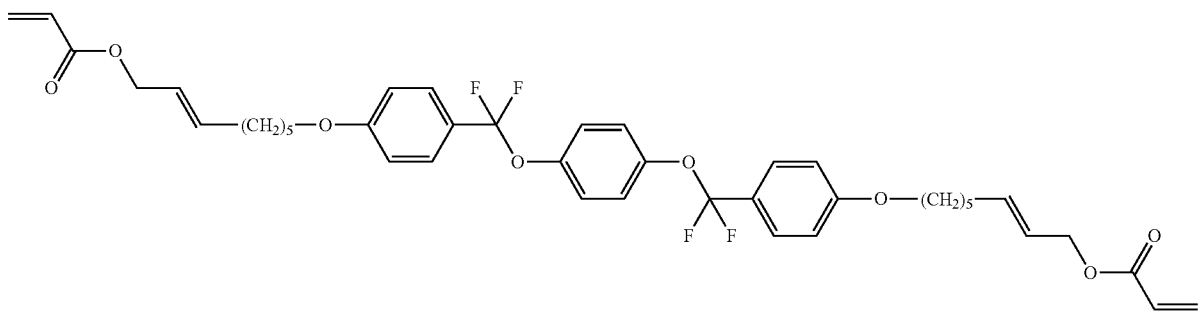

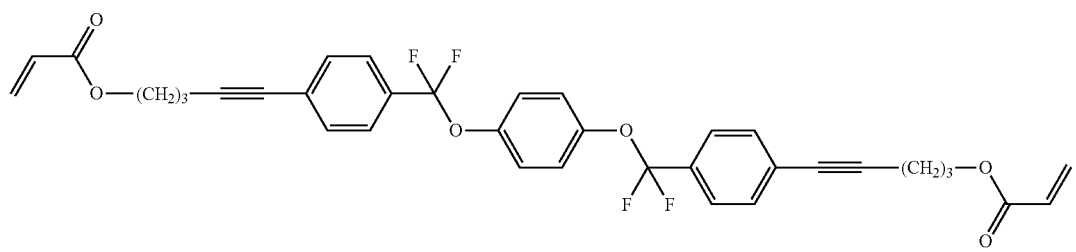

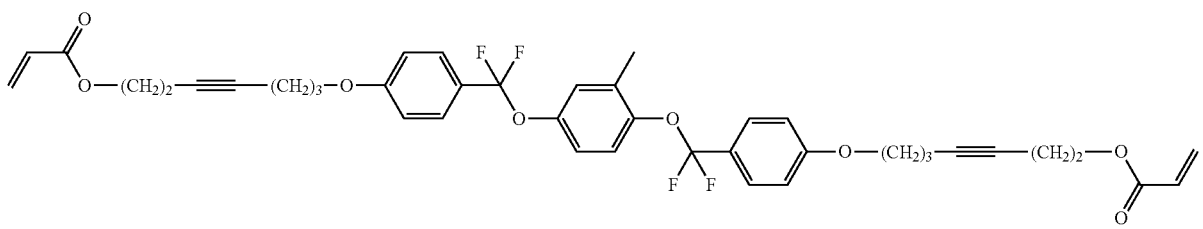

However, the use of compounds of this type for the stabilisation of blue phases or in PSA displays is neither described in nor obvious from JP 2005-015473 A.

The specifications US 2009/0268143 and US 2010/0078593 claim difluorooxymethylene-bridged polymerisable compounds containing a ring system having negative dielectric anisotropy as a component in liquid-crystal mixtures for anisotropic films.

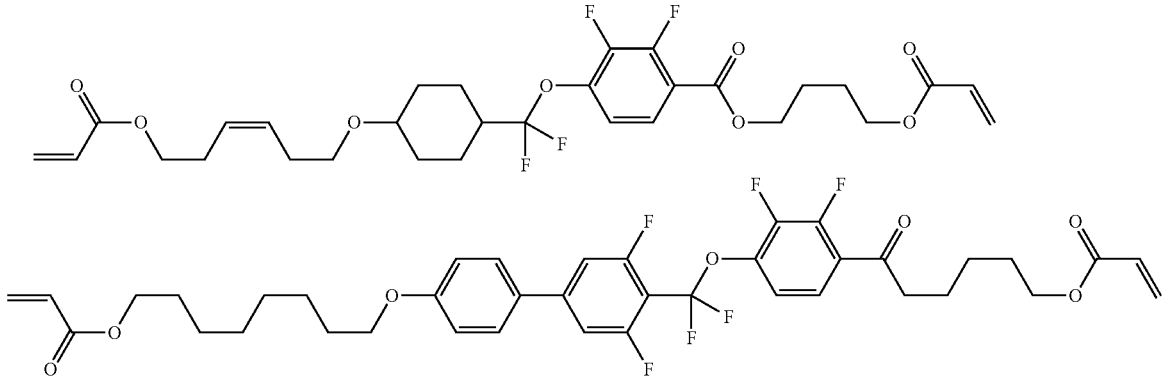

However, no properties of these compounds on use in an LC display are disclosed. In addition, the use of compounds of this type for the stabilisation of blue phases or in PSA displays is neither describe in nor obvious from these specifications.

The invention relates to the compounds of the formula I and to an LC medium comprising one or more compounds of the formula I $$P^a\text{-}(Sp^a)_{s1}\text{-}(A^1\text{-}Z^1)_{n1}\text{-}A^2\text{-}Q^1\text{-}A^3\text{-}(Z^4\text{-}A^4)_{n2}\text{-}(Sp^b)_{s2}\text{-}P^b \qquad I$$

in which the individual radicals have the following meanings:
$P^a$ denotes a polymerisable group,
$P^b$ denotes a polymerisable group, H or F, preferably a polymerisable group,
$Sp^a$, $Sp^b$ each, independently of one another, denote a spacer group,
s1, s2 each, independently of one another, denote 0 or 1,
n1, n2 each, independently of one another, denote 0 or 1, preferably 0,
$Q^1$ denotes —CF$_2$O—, —OCF$_2$—, —CH$_2$O—, —OCH$_2$—, —(CO)O—, —O(CO)—, —(CH$_2$)$_4$—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —(CH$_2$)$_3$O—, —O(CH$_2$)$_3$—, —CH=CF—, —C≡C—, —O—, —CH$_2$—, —(CH$_2$)$_3$—, —CF$_2$—, preferably —CF$_2$O—,
$Z^1$, $Z^4$ denote a single bond, —CF$_2$O—, —OCF$_2$—, —CH$_2$O—, —OCH$_2$—, —(CO)O—, —O(CO)—, —(CH$_2$)$_4$—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —(CH$_2$)$_3$O—, —O(CH$_2$)$_3$—, —CH=CF—, —C≡C—, —O—, —CH$_2$—, —(CH$_2$)$_3$—, —CF$_2$—, where $Z^1$ and $Q^1$ or $Z^2$ and $Q^1$ do not simultaneously denote a group selected from —CF$_2$O— and —OCF$_2$—,
$A^1$, $A^2$, $A^3$, $A^4$
each, independently of one another, denote a radical selected from the following groups:
a) the group consisting of 1,4-phenylene and 1,3-phenylene, in which, in addition, one or two CH groups may be replaced by N and in which, in addition, one or more H atoms may be replaced by L,
b) the group consisting of trans-1,4-cyclohexylene, 1,4-cyclohexenylene and 1,4'-bicyclohexylene, in which, in addition, one or more non-adjacent CH$_2$ groups may be replaced by —O— and/or —S— and in which, in addition, one or more H atoms may be replaced by F or Cl,
c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may, in addition, be mono- or polysubstituted by L,
d) the group consisting of saturated, partially unsaturated or fully unsaturated, and optionally substituted, polycyclic radicals having 5 to 20 cyclic C atoms, one or more of which may also be replaced by heteroatoms, preferably selected from the group consisting of bicyclo[1.1.1]-pentane-1,3-diyl, bicyclo[2.2.2]octane-1,4-diyl, spiro[3.3]-heptane-2,6-diyl,

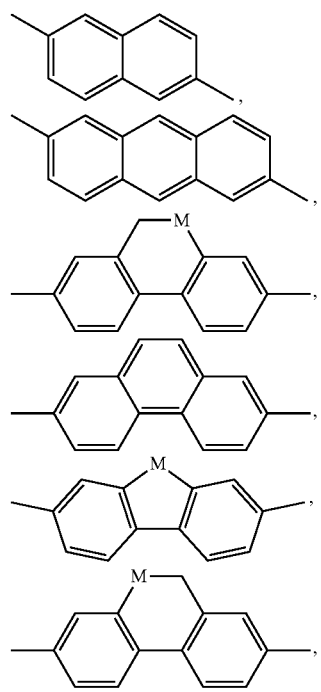

-continued

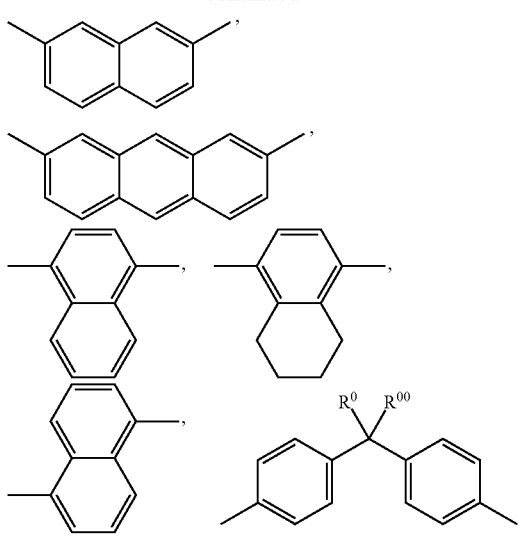

where, in addition, one or more H atoms in these radicals may be replaced by L, and/or one or more double bonds may be replaced by single bonds, and/or one or more CH groups may be replaced by N, L on each occurrence, identically or differently, denotes F, Cl, CN, SCN, $SF_5$ or straight-chain or branched, in each case optionally fluorinated alkyl, alkoxy, alkylcarbonyl, alkoxycarbonyl, alkylcarbonyloxy or alkoxycarbonyloxy having 1 to 12 C atoms, $R^0$, $R^{00}$ each, independently of one another, denote H, F or straight-chain or branched alkyl having 1 to 12 C atoms, in which, in addition, one or more H atoms may be replaced by F, M denotes —O—, —S—, —$CH_2$—, —$CHY^1$— or —$CY^1Y^2$—, and $Y^1$ and $Y^2$ each, independently of one another, have one of the meanings indicated above for $R^0$, or denote Cl or CN, one of the groups $Y^1$ and $Y^2$ alternatively also denotes —$OCF_3$, preferably denote H, F, Cl, CN or $CF_3$, or to a medium comprising a polymer obtainable by polymerisation of one or more compounds of the formula I, and to the use in LC displays having a blue phase or in LC displays of the PS or PSA type.

The invention furthermore relates to an LC medium comprising one or more compounds of the formula I and optionally additionally one or more further polymerisable compounds.

The invention furthermore relates to an LC medium comprising one or more compounds of the formula I and one or more additional compounds, which may also be mesogenic, liquid-crystalline and/or polymerisable.

The invention furthermore relates to an LC medium comprising a polymer obtainable by polymerisation of one or more compounds of the formula I, and optionally comprising one or more additional compounds, which may also be mesogenic, liquid-crystalline and/or polymerisable.

The invention furthermore relates to an LC medium comprising
 a polymerisable component comprising one or more polymerisable compounds of the formula I, or the polymerised form of this polymerisable component, and
 a liquid-crystalline component, also referred to below as "LC host mixture", comprising one or more, preferably two or more, low-molecular-weight (i.e. monomeric and unpolymerisable) compounds as described above and below, which are preferably mesogenic or liquid-crystalline.

The invention furthermore relates to the use of LC media comprising one or more compounds of the formula I in LC displays having a blue phase or in LC displays of the PS or PSA type.

The invention furthermore relates to a process for the preparation of an LC medium as described above and below in which one or more low-molecular-weight liquid-crystalline compounds, or an LC host mixture (liquid-crystal mixture) as described above and below, are mixed with one or more compounds of the formula I and optionally with chiral and/or optically active compounds and/or additives.

The invention furthermore relates to the use of compounds of the formula I and LC media according to the invention comprising them in LC displays for stabilisation of the blue phase, in particular over the largest possible temperature range.

The invention furthermore relates to the use of compounds of the formula I and LC media according to the invention comprising them in PS and PSA displays for the generation of a tilt angle in the LC medium by in situ polymerisation of the compound(s) of the formula I in the PSA display, preferably with application of an electric or magnetic field.

The invention furthermore relates to an LC display containing one or more compounds of the formula I, a polymer obtainable by polymerisation of one or more compounds of the formula I or an LC medium according to the invention, in particular a PS or PSA display, particularly preferably a display having a blue phase, a PSA-VA, PSA-OCB, PSA-IPS, PSA-FFS or PSA-TN display.

The invention furthermore relates to an LC display of the PS or PSA type containing an LC cell having two substrates and two electrodes, where at least one substrate is transparent to light and at least one substrate has one or two electrodes, and a layer, located between the substrates, of an LC medium comprising a polymerised component and a low-molecular-weight component, where the polymerised component is obtainable by polymerisation of one or more polymerisable compounds between the substrates of the LC cell in the LC medium, preferably with application of an electrical voltage to the electrodes, characterised in that at least one of the polymerisable compounds is selected from formula I.

The invention furthermore relates to a process for the production of an LC display as described above and below in which an LC medium comprising one or more low-molecular-weight liquid-crystalline compounds or an LC host mixture as described above and below and one or more polymerisable compounds, at least one of which is selected from formula I, is introduced into an LC cell having two substrates and two electrodes as described above and below, and the polymerisable compounds are polymerised, preferably with application of an electrical voltage to the electrodes.

The PS and PSA displays according to the invention have two electrodes, preferably in the form of transparent layers, which are applied to one or both of the substrates which form the LC cell. Either in each case one electrode is applied to each of the two substrates, as, for example, in PSA-VA, PSA-OCB or PSA-TN displays according to the invention, or both electrodes are applied to only one of the two substrates, while the other substrate has no electrode, as, for example, in PSA-IPS or PSA-FFS displays according to the invention.

The invention furthermore relates to novel compounds of the formula I, to processes for the preparation thereof, and to novel intermediates used in or obtained from these processes, in particular compounds of the formula I, and sub-formulae thereof as defined above and below, in which one or more of the radicals $A^1$ and $A^2$ are selected from the group d) as defined in formula I, consisting of optionally substituted, saturated or partially or fully unsaturated, polycyclic radicals having 5 to 20 cyclic C atoms, one or more of which may also be replaced by heteroatoms.

Particular preference is given to an LC medium, an LC display, a process or the use as described above and below in which the LC medium or the polymerisable or polymerised component present therein does not comprise any compounds of the following formula:

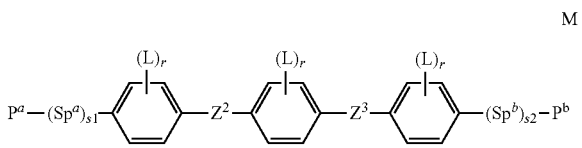

in which $P^a$, $P^b$, $Sp^a$, $Sp^b$, s1, s2 and L have the meanings indicated above and below, r denotes 0, 1, 2, 3 or 4, and $Z^2$ and $Z^3$ each, independently of one another, denote —(CO)O— or —O(CO)—.

The following meanings apply above and below:

The term "cyclic C atom" denotes a C atom which forms a carbo- or heterocyclic radical with other C atoms and/or heteroatoms.

The terms "tilt" and "tilt angle" relate to a tilted alignment of the LC molecules of an LC medium relative to the surfaces of the cell in an LC display (here preferably a PS or PSA display). The tilt angle here denotes the average angle (<90°) between the longitudinal molecular axes of the LC molecules (LC director) and the surface of the plane-parallel outer plates which form the LC cell. A low value of the tilt angle (i.e. a large deviation from the 90° angle) corresponds to a large tilt here. A suitable method for measurement of the tilt angle is given in the examples. Unless indicated otherwise, tilt angle values disclosed above and below relate to this measurement method.

The term "mesogenic group" is known to the person skilled in the art and is described in the literature, and denotes a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerisation. Typical mesogenic groups are, for example, rigid rod- or disc-shaped units. An overview of the terms and definitions used in connection with mesogenic or LC compounds is given in Pure Appl. Chem. 73(5), 888 (2001) and C. Tschierske, G. Pelzl, S. Diele, Angew. Chem. 2004, 116, 6340-6368.

The term "spacer group" or "spacer", also referred to as "Sp" above and below, is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. Unless indicated otherwise, the term "spacer group" or "spacer" above and below denotes a flexible group which connects the mesogenic group and the polymerisable group(s) to one another in a polymerisable mesogenic compound.

The term "reactive mesogen" or "RM" denotes a compound containing one mesogenic group and one or more functional groups which are suitable for polymerisation (also referred to as polymerisable group or group P).

The terms "low-molecular-weight compound" and "unpolymerisable compound" denote compounds, usually monomeric, which contain no functional group which is suitable for polymerisation under the usual conditions known to the person skilled in the art, in particular under the conditions used for the polymerisation of RMs.

"Halogen" denotes F, Cl, Br or I.

Definitions such as "alkyl, alkoxy, alkylcarbonyl, alkoxycarbonyl, alkylcarbonyloxy or alkoxycarbonyloxy having 1 to 12 C atoms", etc., mean that the radicals containing a carbonyl group (CO) and the unsaturated radicals, such as alkenyl and alkynyl, have at least two C atoms, and the branched radicals have at least three C atoms.

The polymerisable group $P^{a,b}$ is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups $P^{a,b}$ are selected from the group consisting of

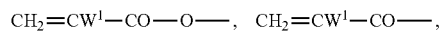

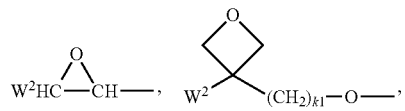

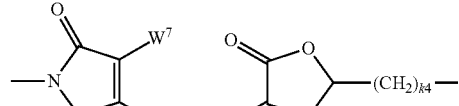

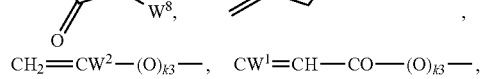

$CW^1$=CH—CO—NH—, $CH_2$=$CW^1$—CO—NH—, $CH_3$—CH=CH—O—, $(CH_2$=CH$)_2$CH—OCO—, $(CH_2$=CH—$CH_2)_2$CH—OCO—, $(CH_2$=CH$)_2$CH—O—, $(CH_2$=CH—$CH_2)_2$N—, $(CH_2$=CH—$CH_2)_2$N—CO—, HO—$CW^2W^3$—, HS—$CW^2W^3$—, $HW^2$N—, HO—$CW^2W^3$—NH—, $CH_2$=$CW^1$—CO—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH—, HOOC—, OCN— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Particularly preferred groups $P^{a,b}$ are selected from the group consisting of

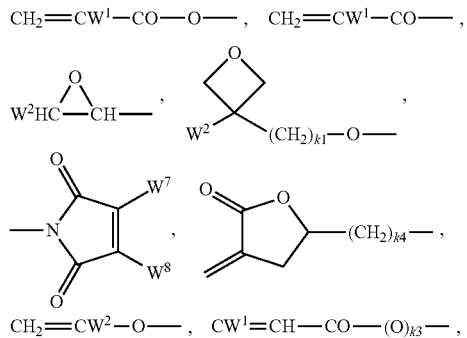

$CW^1$=CH—CO—NH—, $CH_2$=$CW^1$—CO—NH—, ($CH_2$=CH$)_2$CH—OCO—, ($CH_2$=CH—$CH_2)_2$CH—OCO—, ($CH_2$=CH$)_2$CH—O—, ($CH_2$=CH—$CH_2)_2$N—, ($CH_2$=CH—$CH_2)_2$N—CO—, $CH_2$=$CW^1$—CO—NH—, $CH_2$=CH—(COO$)_{k1}$-Phe-(O$)_{k2}$—, $CH_2$=CH—(CO$)_{k1}$-Phe-(O$)_{k2}$—, Phe-CH=CH— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups $P^{a,b}$ are selected from the group consisting of $CH_2$=$CW^1$—CO—O—, in particular $CH_2$=CH—CO—O—, $CH_2$=C($CH_3$)—CO—O— and $CH_2$=CF—CO—O—, furthermore $CH_2$=CH—O—, ($CH_2$=CH$)_2$CH—O—CO—,

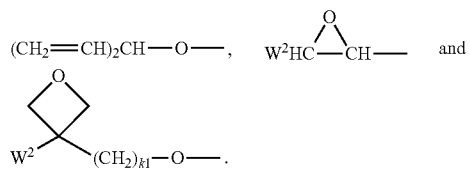

Further very particularly preferred groups $P^{a,b}$ are selected from the group consisting of vinyloxy, acrylate, methacrylate, fluoroacrylate, chloroacrylate, oxetane and epoxide groups, and particularly preferably denote an acrylate or methacrylate group.

Preferred spacer groups $Sp^{a,b}$ are selected from the formula Sp"-X", so that the radical $P^{a/b}$-$Sp^{a/b}$— conforms to the formula $P^{a/b}$-Sp"-X"—, where Sp" denotes alkylene having 1 to 20, preferably 1 to 12, C atoms, which is optionally mono- or polysubstituted by F, Cl, Br, I or CN, and in which, in addition, one or more non-adjacent $CH_2$ groups may each be replaced, independently of one another, by —O—, —S—, —NH—, —N($R^0$)—, —Si($R^{00}R^{000}$)—, —CO—, —CO—O—, —O—CO—, —O—CO—O—, —S—CO—, —CO—S—, —N($R^{00}$)—CO—O—, —O—CO—N($R^{00}$)—, —N($R^{00}$)—CO—N($R^{00}$)—, —CH=CH— or —C≡C— in such a way that O and/or S atoms are not linked directly to one another, X" denotes —O—, —S—, —CO—, —CO—O—, —O—CO—, —O—CO—O—, —CO—N($R^{00}$)—, —N($R^{00}$)—CO—, —N($R^{00}$)—CO—N($R^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=$CR^0$—, —$CY^2$=$CY^3$—, —C≡C—, —CH=CH—CO—O—, —O—CO—CH=CH— or a single bond, $R^{00}$ and $R^{000}$ each, independently of one another, denote H or alkyl having 1 to 12 C atoms, and $Y^2$ and $Y^3$ each, independently of one another, denote H, F, Cl or CN.

X' is preferably —O—, —S—, —CO—, —COO—, —OCO—, —O—COO—, —CO—$NR^0$—, —$NR^0$—CO—, —$NR^0$—CO—$NR^0$— or a single bond.

Typical spacer groups Sp" are, for example, —(CH$_2)_{p1}$—, —(CH$_2$CH$_2$O$)_{q1}$—CH$_2$CH$_2$—, —CH$_2$CH$_2$—S—CH$_2$CH$_2$—, —CH$_2$CH$_2$—NH—CH$_2$CH$_2$— or —(SiR$^{00}$R$^{000}$—O$)_{p1}$—, in which p1 is an integer from 1 to 12, q1 is an integer from 1 to 3, and $R^{00}$ and $R^{000}$ have the meanings indicated above.

Particularly preferred groups -Sp"-X"— are —(CH$_2)_{p1}$—, —(CH$_2)_{p1}$—O—, —(CH$_2)_{p1}$—O—CO—, —(CH$_2)_{p1}$O—CO—O—, in which p1 and q1 have the meanings indicated above.

Particularly preferred groups Sp" are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

In a further preferred embodiment of the invention, $P^a$ and/or $P^b$ in formula I denote a radical containing two or more polymerisable groups (multifunctional polymerisable radicals). Suitable radicals of this type and polymerisable compounds containing them and the preparation thereof are described, for example, in U.S. Pat. No. 7,060,200 B1 or US 2006/0172090 A1. Particular preference is given to multifunctional polymerisable radicals selected from the following formulae:

—X-alkyl-CHP$^1$—CH$_2$—CH$_2$P$^2$    I*a

—X-alkyl-C(CH$_2$P$^1$)(CH$_2$P$^2$)—CH$_2$P$^3$    I*b

—X-alkyl-CHP$^1$CHP$^2$—CH$_2$P$^3$    I*c

—X-alkyl-C(CH$_2$P$^1$)(CH$_2$P$^2$)—C$_{aa}$H$_{2aa+1}$    I*d

—X-alkyl-CHP$^1$—CH$_2$P$^2$    I*e

—X-alkyl-CHP$^1$P$^2$    I*f

—X-alkyl-CP$^1$P$^2$—C$_{aa}$H$_{2aa+1}$    I*g

—X-alkyl-C(CH$_2$P$^1$)(CH$_2$P$^2$)—CH$_2$OCH$_2$—C(CH$_2$P$^3$)(CH$_2$P$^4$)CH$_2$P$^5$    I*h —X-alkyl-CH((CH$_2)_{aa}$P$^1$)((CH$_2)_{bb}$P$^2$)    I*i —X-alkyl-CHP$^1$CHP$^2$—C$_{aa}$H$_{2aa+1}$    I*k —X'-alkyl-C(CH$_3$)(CH$_2$P$^1$)(CH$_2$P$^2$)    I*m in which
alkyl denotes a single bond or straight-chain or branched alkylene having 1 to 12 C atoms, in which one or more non-adjacent CH$_2$ groups may each be replaced, independently of one another, by —C(R$^{00}$)=C(R$^{000}$)—, —C≡C—, —N(R$^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl or CN, where R$^{00}$ and R$^{000}$ have the meanings indicated above, aa and bb each, independently of one another, denote 0, 1, 2, 3, 4, 5 or 6, X has one of the meanings indicated for X', and P$^{1-5}$ each, independently of one another, have one of the meanings indicated for P$^a$.

A$^1$, A$^2$, A$^3$ and A$^4$ in formula I preferably each, independently of one another, denote a radical of definition a), particularly preferably selected from the group consisting of the following formulae:

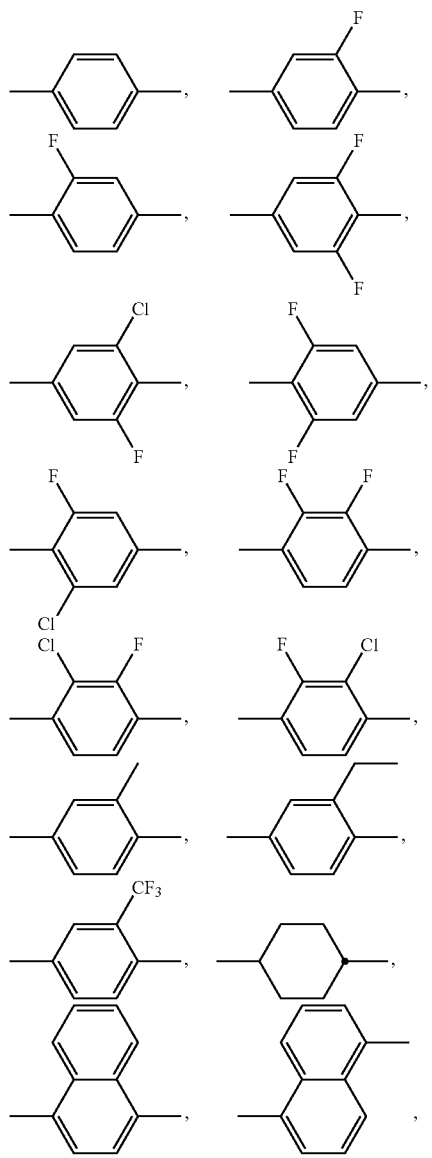

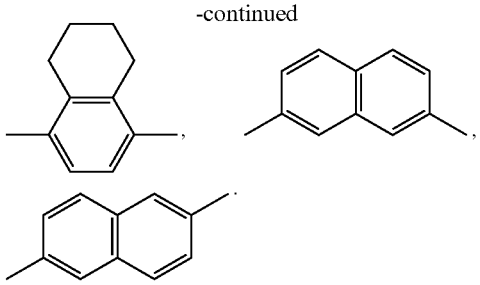

in which the individual rings may also additionally be mono- or polysubstituted by L as described above and below.

A$^1$, A$^2$, A$^3$ and A$^4$ in formula I particularly preferably each, independently of one another, denote a radical selected from the group consisting of the following formulae:

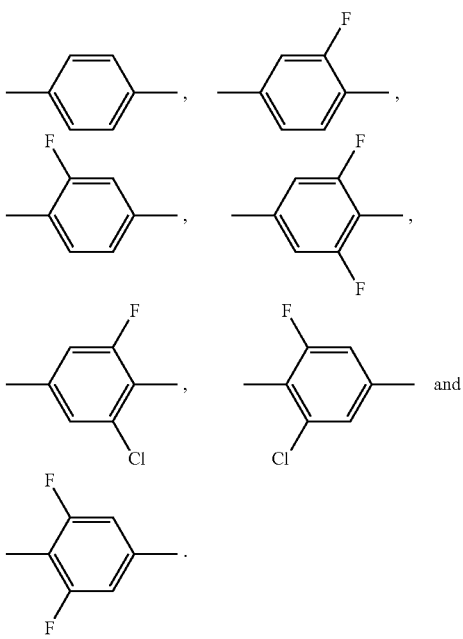

A$^1$, A$^2$, A$^3$ and A$^4$ in formula I furthermore preferably each, independently of one another, denote a radical selected from the group consisting of the following formulae:

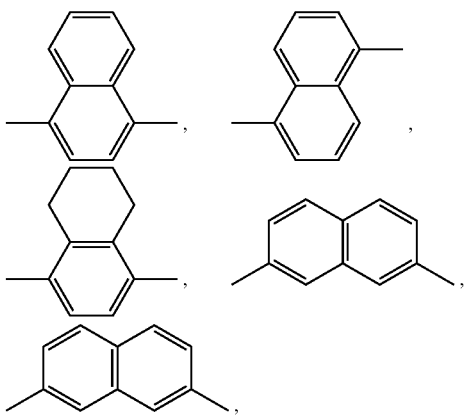

Further particularly preferred compounds of the formula I and sub-formulae thereof indicated above and below are those in which
$Q^1$ denotes a group —$CF_2O$—,
$Q^1$ denotes a group —$OCF_2$—,
s1 and s2 each denote 1,
n1 and n2 each denote 0,
n1 denotes 1 and n2 denotes 0 or n1 denotes 0 and n2 denotes 1,
$A^3$ denotes a group of the formula

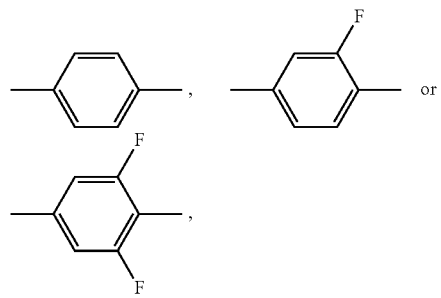

$A^2$ denotes a group of the formula particularly preferably $A^2$ and $Q^1$ together denote a group of the formula

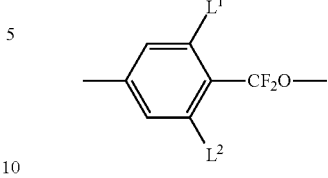

in which $L^1$ and $L^2$ independently denote H, Cl or F, preferably $L^1$=F and $L^2$ denotes H or F, and particularly preferably $L^1$ and $L^2$ denote F.

The compounds of the formula I are therefore particularly preferably compounds of the formula

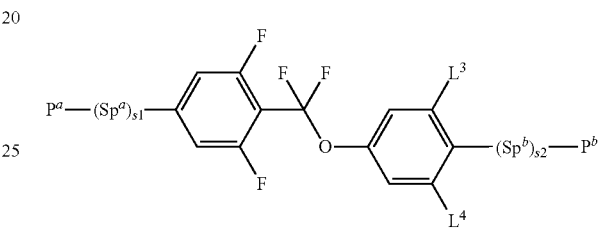

in which $P^a$, $P^b$, $Sp^a$, $Sp^b$, s1, s2 are as defined for formula I, and $L^3$ and $L^4$, independently of one another, denote H or F.

A high degree of fluorination in the rings $A^2$ and $A^3$ makes the polymerisable compounds very readily combinable with mixtures of compounds containing polyfluorinated aromatic rings.

The compounds according to the invention are preferably represented by the formula I*:

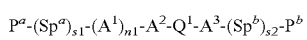

in which the variable groups are as defined for formula I and preferably adopt the meanings preferred therein.

Particularly preferred compounds of the formula I are selected from the group consisting of the following formulae:

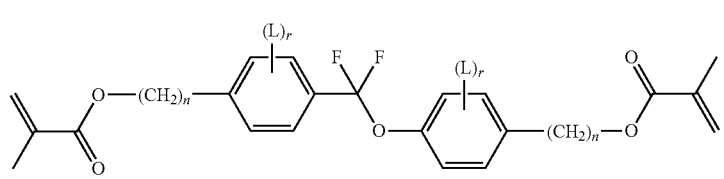

I1

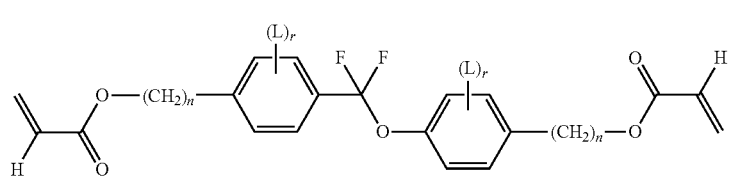

I2

-continued
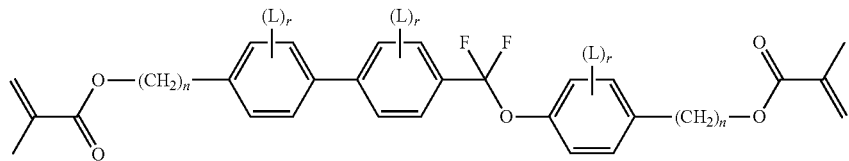
I3
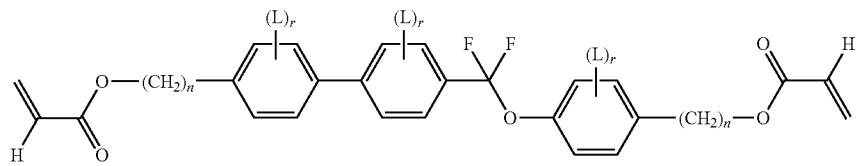
I4
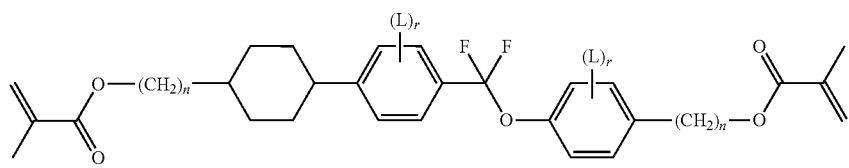
I5
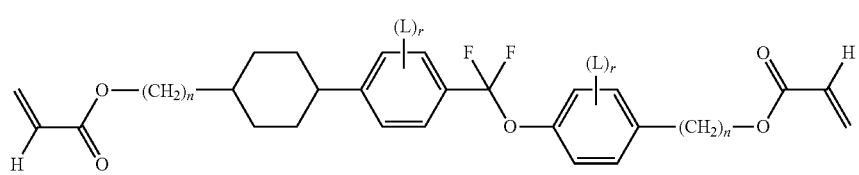
I6
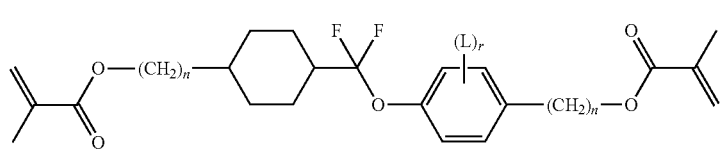
I7
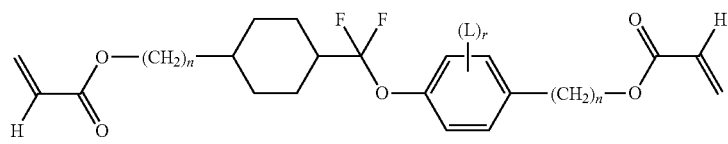
I8
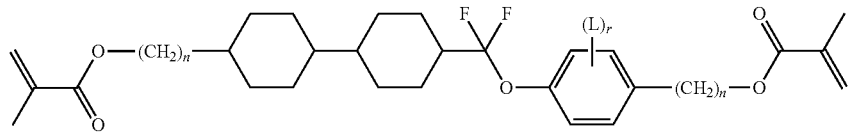
I9
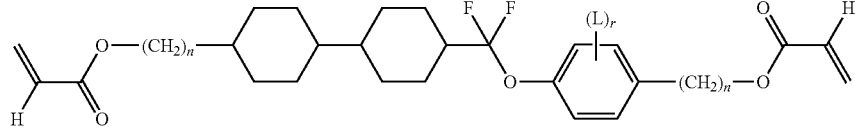
I10
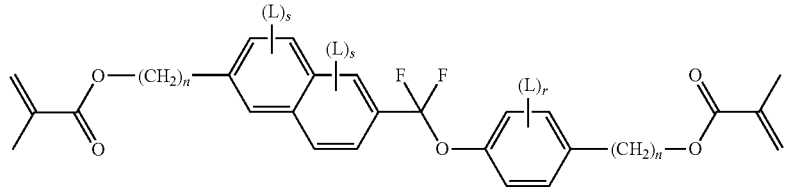
I11

-continued
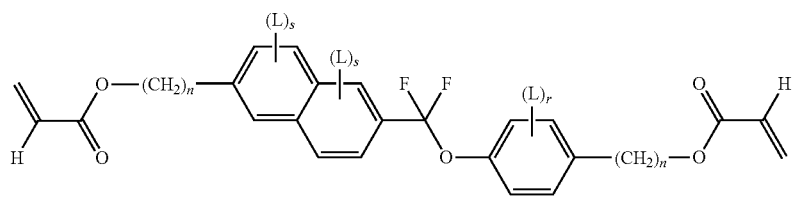
I12
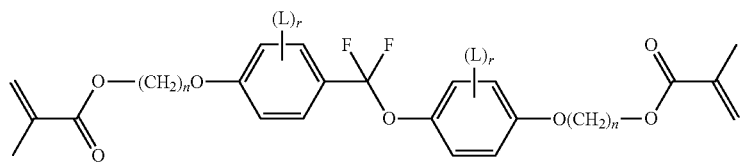
I13
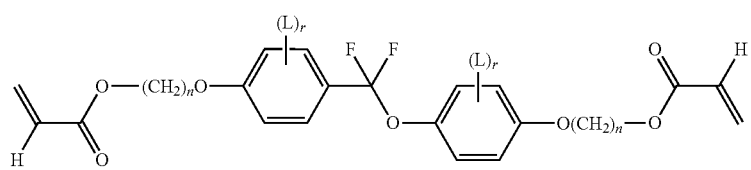
I14
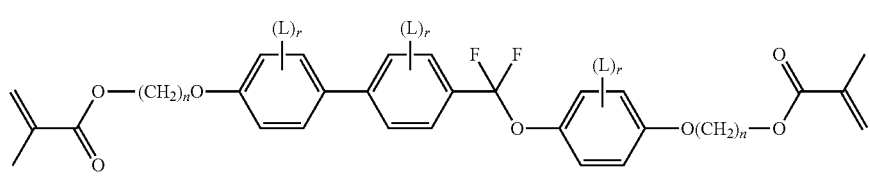
I15
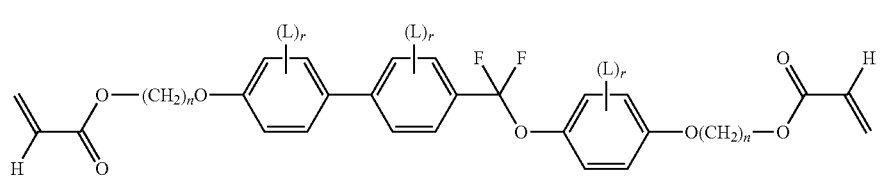
I16
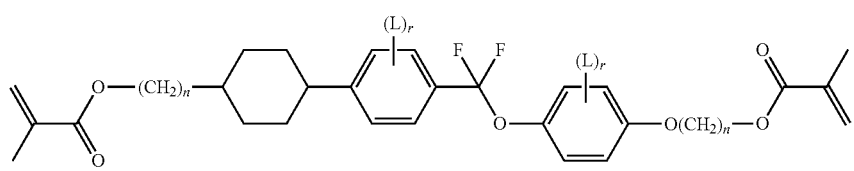
I17
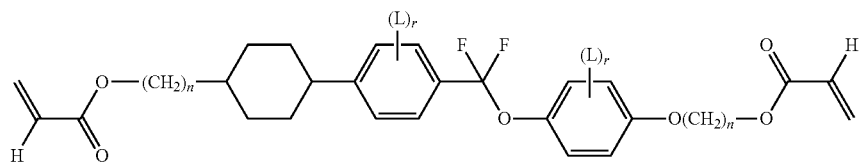
I18
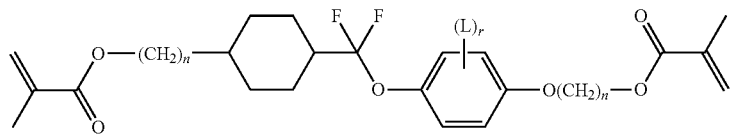
I19
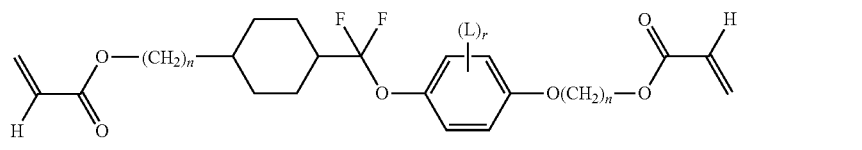
I20
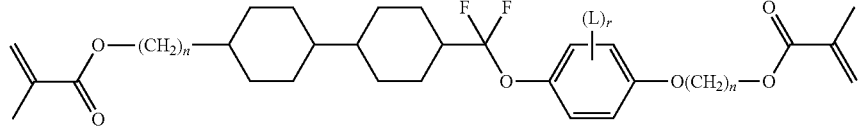
I21

-continued

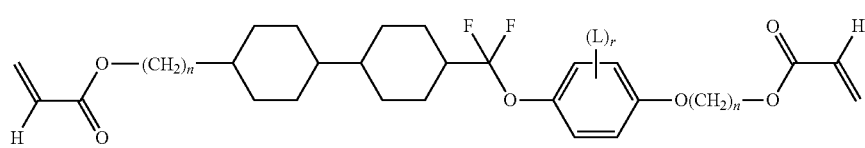

I22

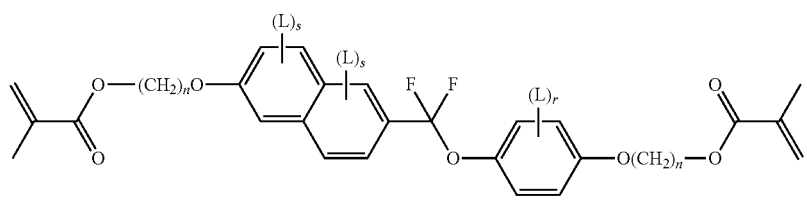

I23

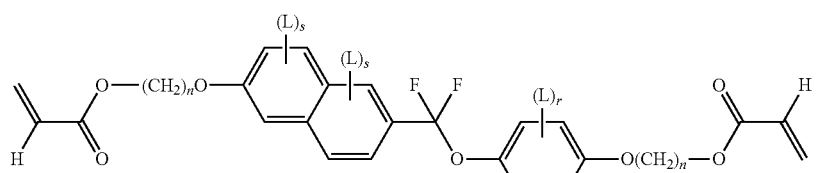

I24

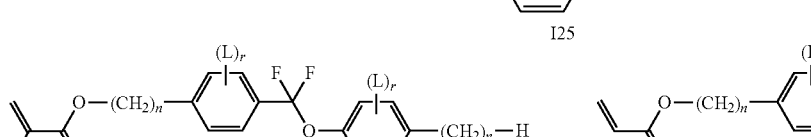

I25   I26

I27   I28

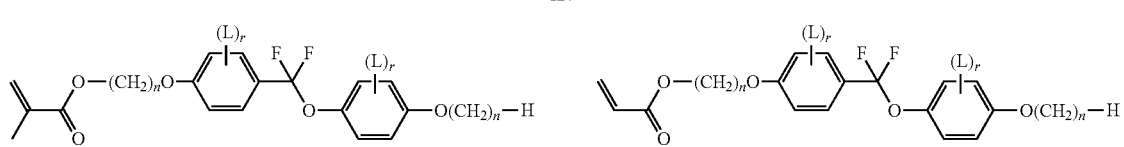

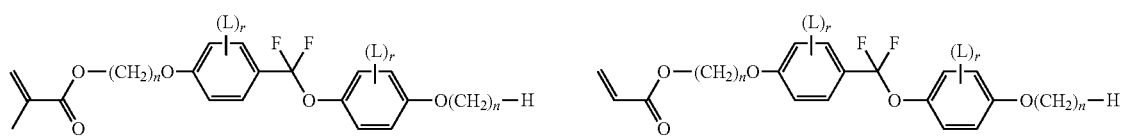

in which L on each occurrence, identically or differently, has one of the meanings indicated above and below, r denotes 0, 1, 2, 3 or 4, s denotes 0, 1, 2 or 3, and n denotes an integer between 1 and 24, preferably between 1 and 12, very particularly preferably between 2 and 8, and in which, if a radical at the end of a single or double bond is not named, it is a terminal $CH_3$ or $CH_2$ group. r is preferably 0, 1 or 2, and particularly preferably 1 or 2. Of these, very particular preference is given to the compounds of the formulae I1, I2, I3 and I4 and very particularly the compounds of the formulae I1 and I2.

In the formulae I1-I24,

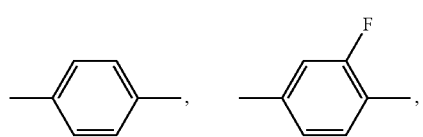

preferably denotes a group selected from the group consisting of the following formulae:

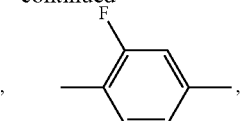

-continued

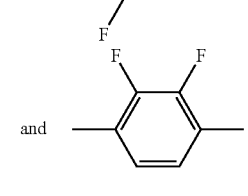

and particularly preferably

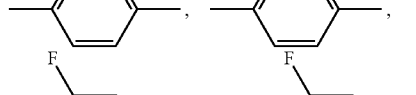

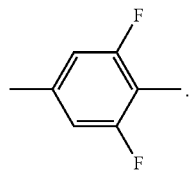
Of the compounds of the formula I, preference is given to those containing two ring systems (n1, n2=0), in particular compounds selected from the compounds of the formulae Ia to Ir:
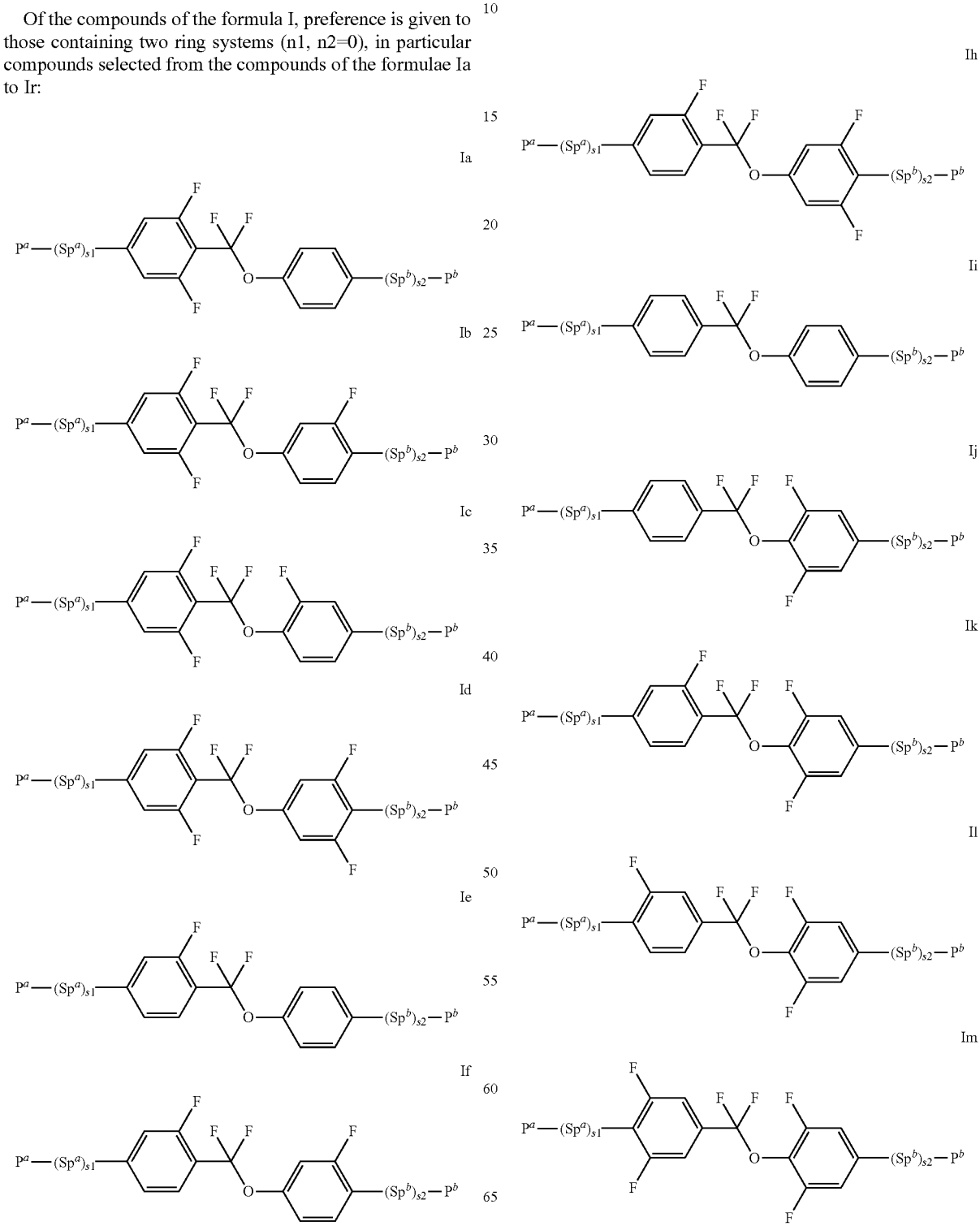

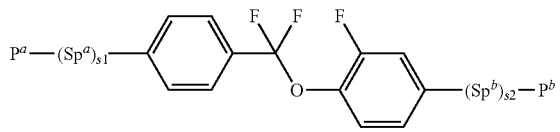
In

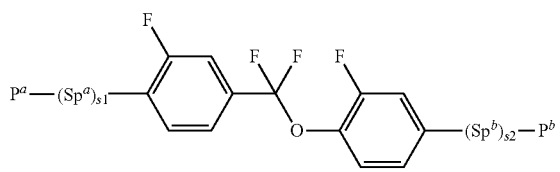
Io

Ip

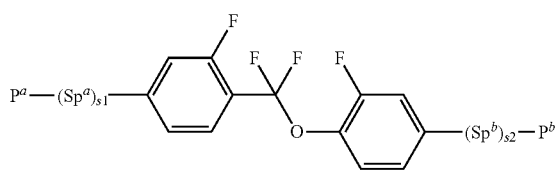
Iq

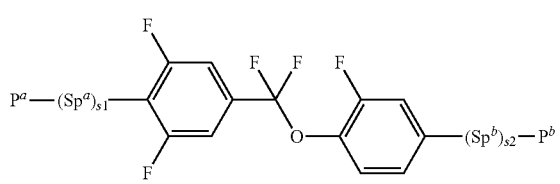

in which $P^a$, $P^b$, $Sp^a$, $Sp^b$, s1 and s2 are as defined for formula I. $Sp^{a/b}$ here preferably denote an alkylene group —$(CH_2)_n$—, where n=3, 4, 5, 6 or 7, and $P^{a/b}$ denote a methacrylate or acrylate group or H, in particular a methacrylate or acrylate group. Of these, particular preference is given to the compounds of the formulae Ia, Ib, Ic, Id, Ie, If, Ig and Ih and very particularly of the formulae Ia, Ib, Id and Ih.

The group $A^2$-$Q^1$-$A^3$ preferably denotes a group of the formula

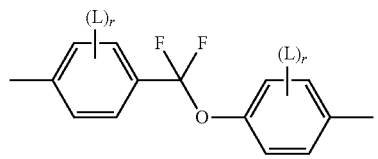

in which at least one of the rings is substituted by at least one group L=F or Cl, particularly preferably by L=F. r here is in each case independently preferably 0, 1 or 2.

$P^a$ and $P^b$ in the compounds of the formula I and sub-formulae thereof preferably denote acrylate or methacrylate, furthermore fluoroacrylate. $Sp^a$ and $Sp^b$ in the compounds of the formula I and sub-formulae thereof preferably denote a radical selected from the group consisting of —$(CH_2)_{p1}$—, —$(CH_2)_{p1}$—O—, —$(CH_2)_{p1}$—O—CO— and —$(CH_2)_{p1}$—O—CO—O— and mirror images thereof, in which p1 denotes an integer from 1 to 12, preferably from 1 to 6, particularly preferably 1, 2 or 3, where these groups are linked to $P^a$ or $P^b$ in such a way that O atoms are not directly adjacent.

Of the compounds of the formula I, particular preference is given to those in which
the radicals $P^a$ and $P^b$ are selected from the group consisting of vinyloxy, acrylate, methacrylate, fluoroacrylate, chloroacrylate, oxetane and epoxide groups, particularly preferably acrylate or methacrylate groups, the radicals $Sp^a$ and $Sp^b$ are selected from the group consisting of —$(CH_2)_{p1}$—, —$(CH_2)_{p1}$—O—, —$(CH_2)_{p1}$—O—CO— and —$(CH_2)_{p1}$—O—CO—O— and mirror images thereof, in which p1 denotes an integer from 1 to 12, preferably from 1 to 6, particularly preferably 1, 2 or 3, where these radicals are linked to $P^a$ or $P^b$ in such a way that O atoms are not directly adjacent.

The compounds of the formula I and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

Particularly suitable and preferred processes for the preparation of compounds of the formula I and sub-formulae thereof are depicted by way of example in the following schemes and preferably contain one or more of the steps described below.

The person skilled in the art will be able to modify the synthesis in a suitable manner and thus obtain further compounds according to the invention. The particularly preferred compounds containing an alkoxy spacer or acrylates bonded directly to the ring are obtained, for example, by reaction of phenol derivatives, such as, for example, compound 2, with the dithianylium salts 3. The compounds 4 initially formed here are converted into the compounds 5. The hydroxyl group can subsequently be suitably functionalised, for example by esterification using methacrylic acid (cf. Scheme 1).

Scheme 1: Example of the synthesis of compounds according to the invention containing directly bonded acrylates

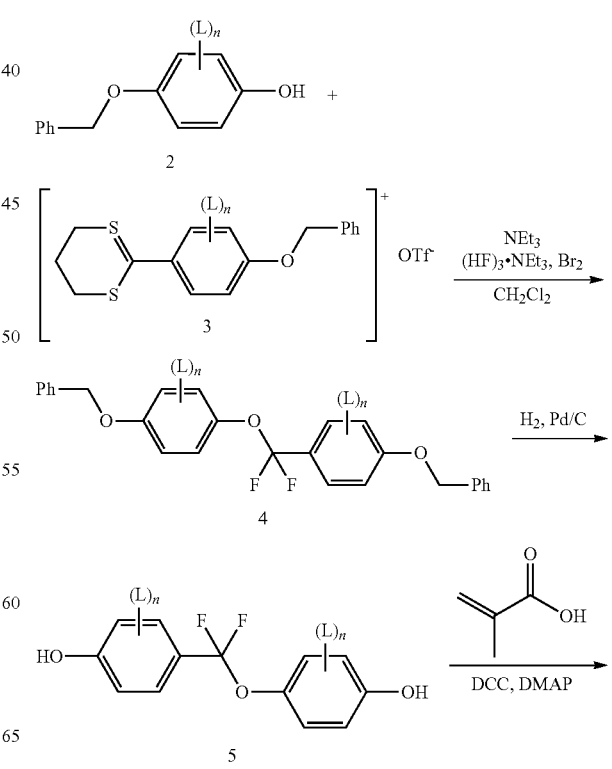

-continued

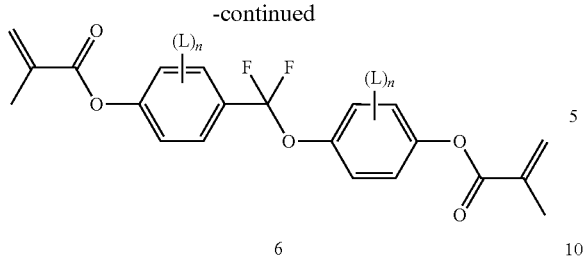

If compounds according to the invention containing alkoxy spacers are to be obtained (for example compound 8 in Scheme 2), the compounds 5 are then reacted with bromoalkanols 7 in the presence of a suitable base. The product can subsequently be esterified again using acrylic acids.

Scheme 2: Example of the synthesis of compounds according to the invention containing alkoxy spacers

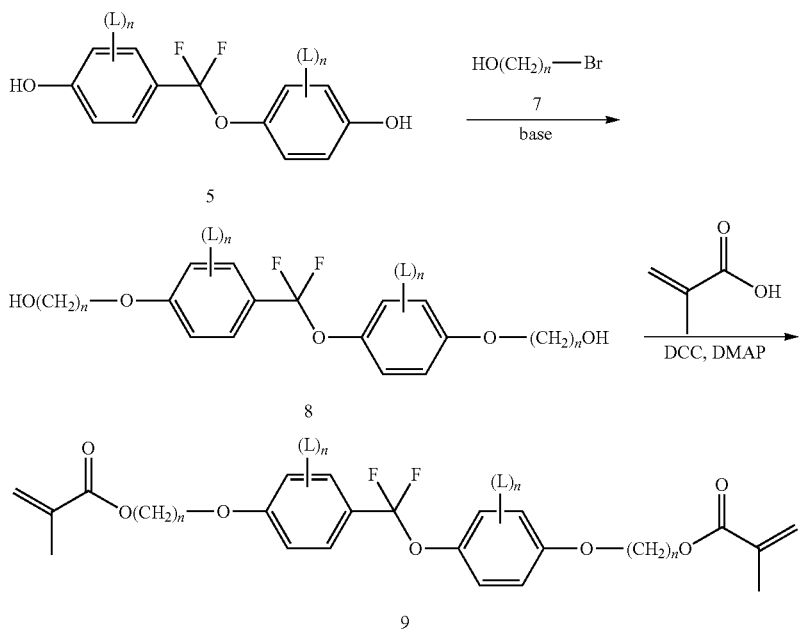

Alternatively, the spacer can also be introduced by a Mitsunobu reaction (cf. Scheme 3).

Scheme 3: Example of the synthesis of compounds according to the invention containing alkoxy spacers by a Mitsunobu reaction

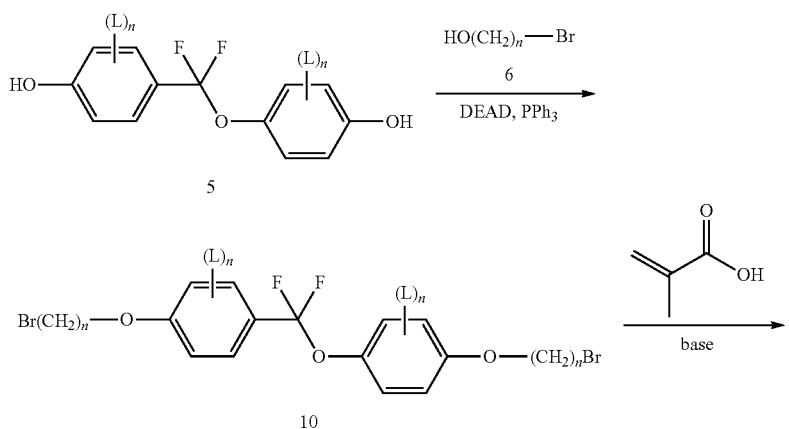

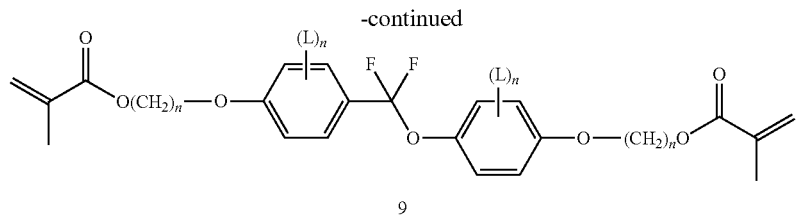

9

C—C-linked spacers can be obtained from the aryl halides 11, which are accessible correspondingly to the compounds 4, for example by a Sonogashira reaction with terminal alkynols (Scheme 4). Subsequent hydrogenation of the compounds 12 results in the saturated compounds 13, from which the acrylates 14 according to the invention are prepared.

The polymerisable compounds of the formula I containing only one polymerisable group $P^a$ are prepared starting from compounds which carry one of the desired unpolymerisable groups, such as alkyl or F, at the corresponding position.

pretilt angle, and subsequently, in a second polymerisation step without an applied voltage, to polymerise or crosslink the compounds which have not reacted in the first step ("end curing").

Suitable and preferred polymerisation methods are, for example, thermal or photopolymerisation, preferably photopolymerisation, in particular UV photopolymerisation. One or more initiators can optionally also be added here. Suitable conditions for the polymerisation and suitable types and amounts of initiators are known to the person skilled in the art Scheme 4: Example of the synthesis of compounds according to the invention containing C-C-linked spacers

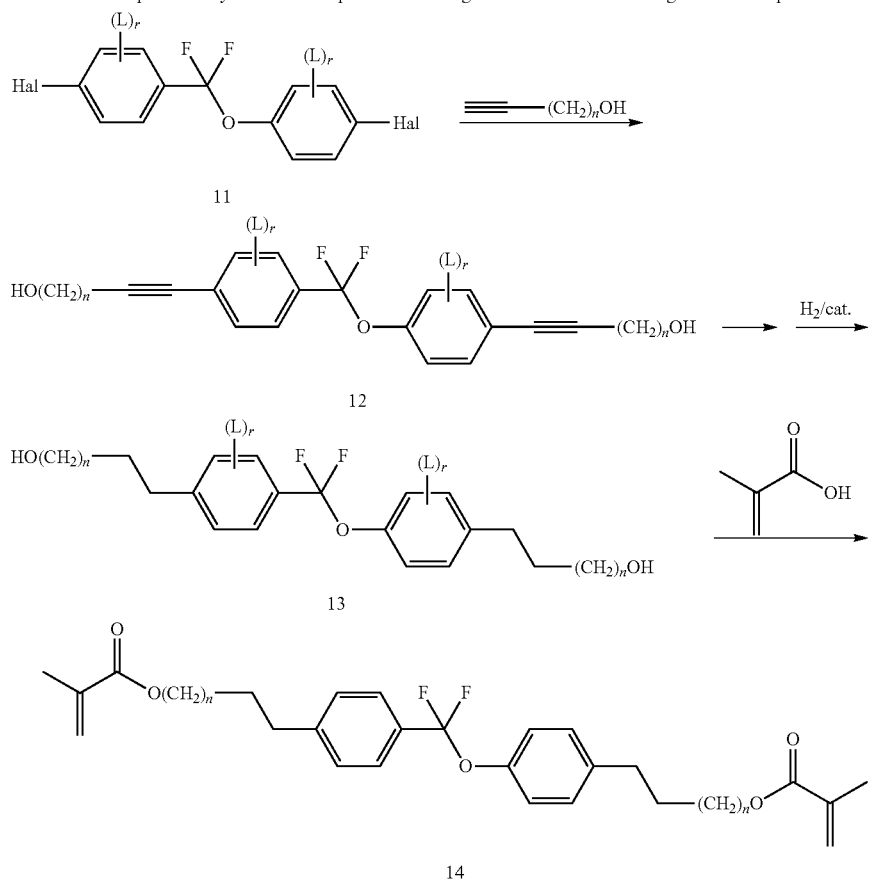

For the production of PSA displays according to the invention, the polymerisable compounds are polymerised or crosslinked (if one compound contains two or more polymerisable groups) by in-situ polymerisation in the LC medium between the substrates of the LC display with application of a voltage. The polymerisation can be carried out in one step. It is also possible firstly to carry out the polymerisation with application of a voltage in a first step in order to generate a and are described in the literature. Suitable for free-radical polymerisation are, for example, the commercially available photoinitiators Irgacure651®, Irgacure184®, Irgacure907®, Irgacure369® or Darocure1173® (Ciba AG). If an initiator is employed, its proportion is preferably 0.001 to 5% by weight, particularly preferably 0.001 to 1% by weight.

The polymerisable compounds according to the invention are also suitable for polymerisation without an initiator, which is accompanied by considerable advantages, such as, for example, lower material costs and in particular less contamination of the LC medium by possible residual amounts of the initiator or degradation products thereof. The polymerisation can thus also be carried out without the addition of an initiator. In a preferred embodiment, the LC medium thus comprises no polymerisation initiator.

The polymerisable component or the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of RMs or the polymerisable component, is preferably 10-10,000 ppm, particularly preferably 50-500 ppm.

The polymerisable compounds according to the invention can be polymerised individually, but it is also possible to polymerise mixtures which comprise two or more polymerisable compounds according to the invention, or mixtures comprising one or more polymerisable compounds according to the invention and one or more further polymerisable compounds (comonomers), which are preferably mesogenic or liquid-crystalline. In the case of polymerisation of such mixtures, copolymers form. Preference is given to the use of a mixture comprising two or more compounds according to the invention or a mixture comprising one or more compounds according to the invention with one or more further polymerisable compounds. The invention furthermore relates to the polymerisable mixtures mentioned above and below. The polymerisable compounds and comonomers are mesogenic or non-mesogenic, preferably mesogenic or liquid-crystalline.

Suitable and preferred comonomers for use in displays according to the invention are selected, for example, from the following formulae:

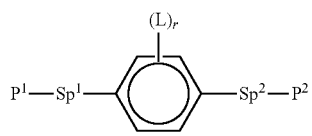

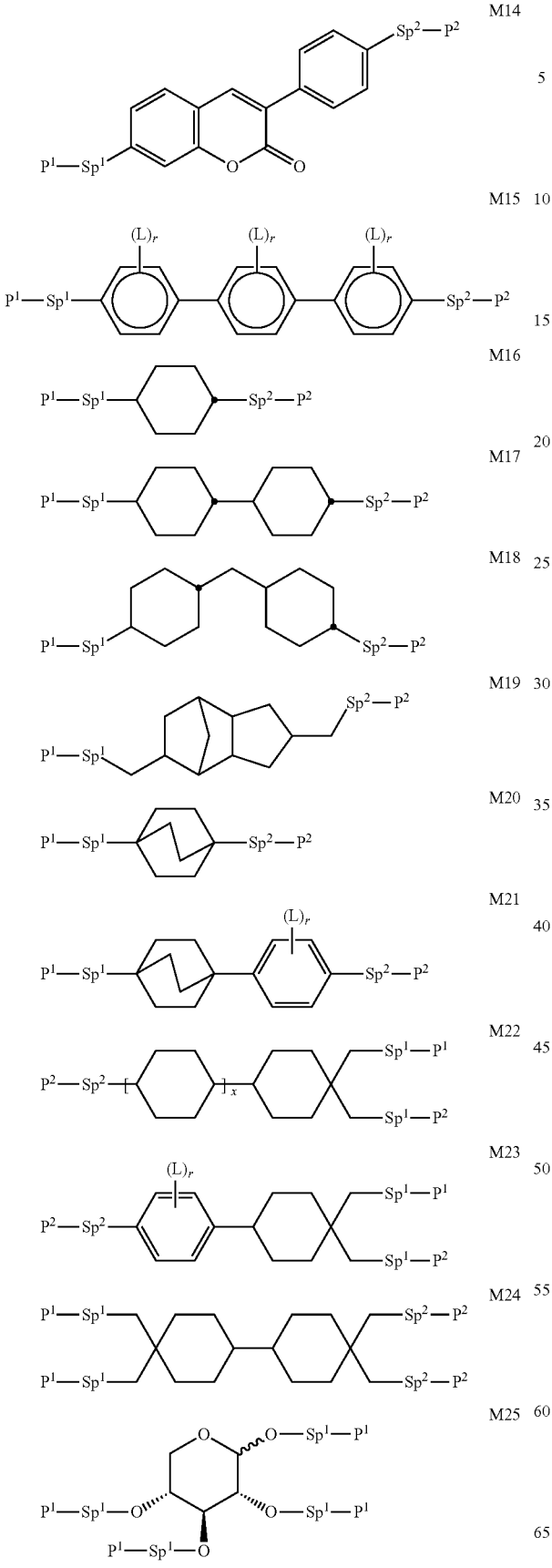
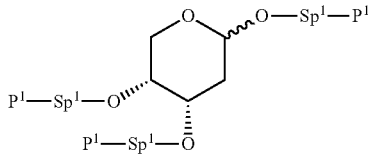
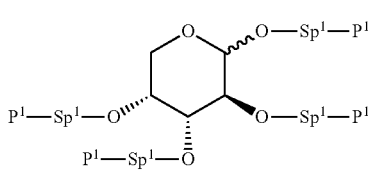
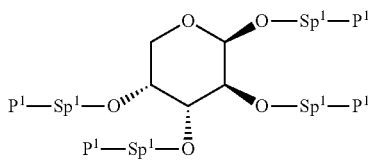
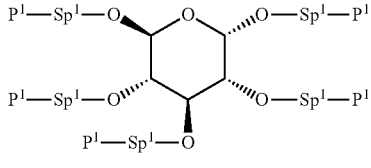

in which the individual radicals have the following meanings:

$P^1$ and $P^2$ each, independently of one another, denote a polymerisable group, preferably having one of the meanings indicated above and below for $P^a$, particularly preferably an acrylate, methacrylate, fluoroacrylate, oxetane, vinyloxy or epoxide group, $Sp^1$ and $Sp^2$ each, independently of one another, denote a single bond or a spacer group, preferably having one of the meanings indicated above and below for $Sp^a$, particularly preferably —$(CH_2)_{p1}$—, —$(CH_2)_{p1}$—O—, —$(CH_2)_{p1}$—CO—O— or —$(CH_2)_{p1}$—O—CO—O—, in which p1 is an integer from 1 to 12, where the linking to the adjacent ring in the last-mentioned groups takes place via the O atom, where, in addition, one or more of the radicals $P^1$-$Sp^1$- and $P^2$-$Sp^2$- may denote a radical $R^{aa}$, with the proviso that at least one of the radicals $P^1$-$Sp^1$- and $P^2$-$Sp^2$- present does not denote $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^o)=C(R^{oo})$—, —C≡C—, —N($R^o$)—, —O—, —S—, —CO—, —CO—O—, —O—CO—, —O—CO—O— in such a way that O and/or S atoms are not linked directly to one another, and in which, in addition, one or more H atoms may be replaced by F, Cl, CN or $P^1$-$Sp^1$-, particularly preferably straight-chain or branched, optionally mono- or polyfluorinated alkyl, alkoxy, alkenyl, alkynyl, alkylcarbonyl, alkoxycarbonyl or alkylcarbonyloxy having 1 to 12 C atoms (where the alkenyl and alkynyl radicals have at least two C atoms and the branched radicals have at least three C atoms), $R^o$, $R^{oo}$ each, independently of one another and on each occurrence identically or differently, denote H or alkyl having 1 to 12 C atoms, $R^y$ and $R^z$ each, independently of one another, denote H, F, $CH_3$ or $CF_3$, $Z^1$ denotes —O—, —CO—, —C(R$^y$R$^z$)— or —CF$_2$CF$_2$—,
$Z^2$ and $Z^3$ each, independently of one another, denote —CO—O—, —O—CO—, —CH$_2$O—, —OCH$_2$—, —CF$_2$O—, —OCF$_2$— or —(CH$_2$)$_n$—, where n is 2, 3 or 4,
L on each occurrence, identically or differently, denotes F, Cl, CN, SCN, SF$_5$ or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F,
L' and L'' each, independently of one another, denote H, F or Cl,
r denotes 0, 1, 2, 3 or 4,
s denotes 0, 1, 2 or 3,
t denotes 0, 1 or 2,
x denotes 0 or 1.

Suitable and preferred comonomers for use in displays according to the invention in the blue phase are selected, for example, from monoreactive compounds, preferably in an amount of 1 to 9%, particularly preferably 4 to 7%. Preferred monoreactive compounds are those of the formulae M1 to M29 in which one or more of the radicals P$^1$-Sp$^1$- and P$^2$-Sp$^2$- denote a radical R$^{aa}$, meaning that only one reactive group is present.

Preferred monoreactive compounds are compounds of the formulae

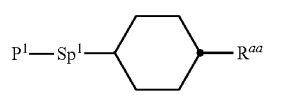

M16-A

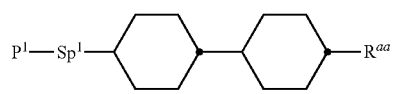

M17-A in which P$^1$, Sp$^1$ and R$^{aa}$ are as defined above.

In addition to the compounds of the formula I, the LC medium or the polymerisable component for a PS or PSA display preferably comprises one or more compounds selected from the group consisting of the formulae M16-M29, particularly preferably consisting of the formulae M16-M21, very particularly preferably consisting of the formulae M16, M17 and M18. For these displays, the polymerisable component preferably consists predominantly of direactive compounds.

Besides the polymerisable compounds described above, the LC media for use in the LC displays according to the invention comprise an LC mixture ("host mixture") comprising one or more, preferably two or more, low-molecular-weight (i.e. monomeric or unpolymerised) compounds. The latter are stable or unreactive to a polymerisation reaction under the conditions used for the polymerisation of the polymerisable compounds. In principle, any LC mixture which is suitable for use in conventional VA and OCB displays is suitable as host mixture.

Suitable LC mixtures are known to the person skilled in the art and are described in the literature. LC media for VA displays are described in EP 1 378 557 A1. LC media for OCB displays are described in EP 1 306 418 A1 and DE 102 24 046 A1. LC media for LC displays having a blue phase are described in WO 2006/063662 A1 and the documents cited therein.

Particularly preferred LC media for use in LC displays having a blue phase are described below:

An LC medium according to the invention having a blue phase preferably comprises
  a polymerisable component A, preferably in a concentration of 1 to 25%, particularly preferably 2 to 20%, very particularly preferably 3 to 10%, comprising, preferably consisting principally of, very particularly preferably consisting exclusively of, one or more compounds of the formula I and optionally one or more additional polymerisable compounds, and
  a liquid-crystalline component B comprising one or more, preferably two or more, low-molecular-weight (i.e. monomeric and unpolymerisable) compounds, preferably in a concentration of 5-100%, preferably having positive dielectric anisotropy, preferably consisting principally of, very particularly preferably consisting exclusively of, one or more compounds of the formula II

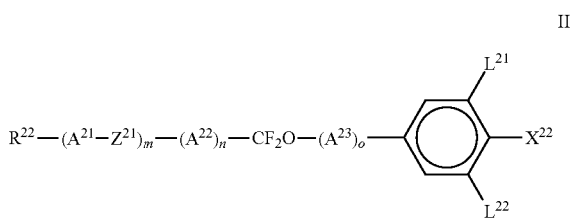

II in which the individual radicals have the following meanings:
R$^{22}$ denotes H, F, Cl or straight-chain or branched alkyl having 1 to 20 C atoms, which is unsubstituted or mono- or polysubstituted by F, Cl or CN, and in which, in addition, one or more non-adjacent CH$_2$ groups may also each be replaced, independently of one another, by —O—, —S—, —SiR$^{01}$R$^{02}$—, —CO—, —COO—, —OCO—, —OCO—O—, —CY$^{01}$=CY$^{02}$— or —C≡C— in such a way that O and/or S atoms are not linked directly to one another,
Y$^{01}$, Y$^{02}$ each, independently of one another, denote F, Cl or CN, one of the radicals Y$^{01}$ and Y$^{02}$ also denotes H,
R$^{01}$, R$^{02}$ each, independently of one another, denote H or alkyl having 1 to 12 C atoms,
A$^{21}$, A$^{22}$, A$^{23}$ each, independently of one another and on each occurrence identically or differently, denote

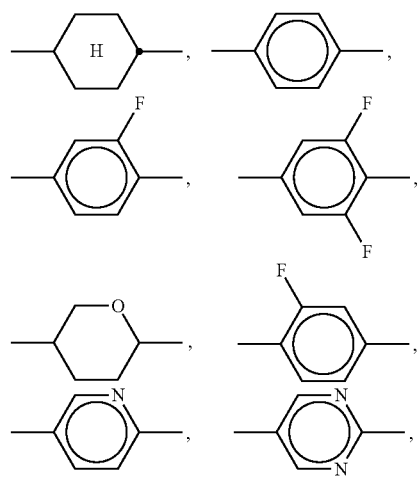

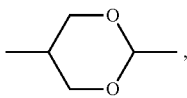,

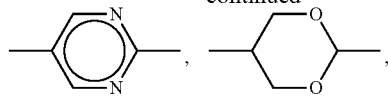

$Z^{21}$ in each case, independently of one another and on each occurrence identically or differently, denotes a single bond, $-(CH_2)_4-$, $-CH_2CH_2-$, $-CF_2-CF_2-$, $-CF_2-CH_2-$, $-CH_2-CF_2-$, $-CH=CH-$, $-CF=CF-$, $-CF=CH-$, $-(CH_2)_3O-$, $-O(CH_2)_3-$, $-CH=CF-$, $-C\equiv C-$, $-CH_2O-$, $-OCH_2-$, $-CF_2O-$, $-OCF_2-$, $-CO-O-$ or $-O-CO-$, $X^{22}$ denotes F, Cl, $-CN$, $-NCS$, $-SF_5$, $-SO_2CF_3$, or alkyl, alkenyl, alkenyloxy, alkylalkoxy or alkoxy having 1 to 3 C atoms, which is mono- or polysubstituted by F, Cl or CN, $L^{21}$, $L^{22}$ each, independently of one another, denote H or F, m denotes 0, 1 or 2, n denotes 1, 2 or 3, o denotes 0, 1 or 2, where m+n+o denotes 1, 2, 3 or 4, preferably 2, 3 or 4, optionally a liquid-crystalline component C comprising one or more, preferably two or more, low-molecular-weight (i.e. monomeric and unpolymerisable) compounds, preferably in a concentration of 1 to 25%, preferably consisting principally of, very particularly preferably consisting exclusively of, one or more compounds of the formula III

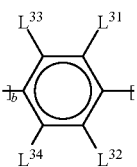    III in which a, b, c, d each, independently of one another, denote 0, 1 or 2, where a+b+c+d is 0, 1, 2, 3 or 4, $A^{31}$, $A^{32}$, $A^{33}$, $A^{34}$ each, independently of one another and on each occurrence identically or differently, denote

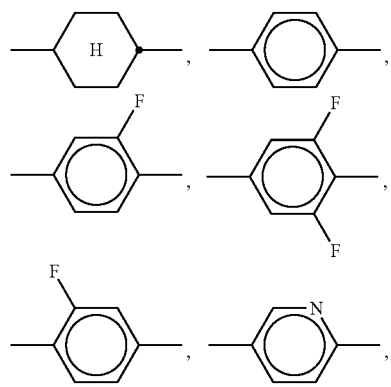

$Z^{31}$, $Z^{32}$, $Z^{33}$, $Z^{34}$ each, independently of one another and on each occurrence identically or differently, denote a single bond, $-(CH_2)_4-$, $-CH_2CH_2-$, $-CF_2-CF_2-$, $-CF_2-CH_2-$, $-CH_2-CF_2-$, $-CH=CH-$, $-CF=CF-$, $-CF=CH-$, $-(CH_2)_3O-$, $-O(CH_2)_3-$, $-CH=CF-$, $-C\equiv C-$, $-CH_2O-$, $-OCH_2-$, $-CF_2O-$, $-OCF_2-$, $-CO-O-$ or $-O-CO-$, $R^{33}$ denotes alkyl or alkoxy having 1 to 15 C atoms, which is unsubstituted or mono- or polysubstituted by F, Cl or CN, and in which, in addition, one or more non-adjacent $CH_2$ groups may also each be replaced, independently of one another, by $-O-$, $-S-$, $-SiR^xR^y-$, $-CH=CH-$, $-C\equiv C-$, $-CO-O-$ and/or $-O-CO-$ in such a way that O and/or S atoms are not linked directly to one another, preferably a straight-chain alkyl, alkoxy, alkenyl, alkenyloxy or $-O$-alkylene-$O-$ radical having up to 10 C atoms, which is unsubstituted or mono- or polysubstituted by F or Cl, $L^{31}$, $L^{32}$, $L^{33}$, $L^{34}$ each, independently of one another, denote H, F, Cl, CN, or alkyl or alkoxy having 1 to 15 C atoms, which is unsubstituted or mono- or polysubstituted by F, Cl or CN, and in which, in addition, one or more non-adjacent $CH_2$ groups may also each be replaced, independently of one another, by $-O-$, $-S-$, $-SiR^xR^y-$, $-CH=CH-$, $-C\equiv C-$, $-CO-O-$ and/or $-O-CO-$ in such a way that O and/or S atoms are not linked directly to one another, with the proviso that at least one of the radicals $L^{31}$, $L^{32}$, $L^{33}$ and $L^{34}$ is other than H, $X^{33}$ denotes F, Cl, $CF_3$, $OCF_3$, CN, NCS, $-SF_5$ or $-SO_2-R^z$, $R^x$ and $R^y$ each, independently of one another, denote H, alkyl or alkoxy having 1 to 7 C atoms, preferably methyl, ethyl, propyl or butyl, and $R^z$ denotes alkyl having 1 to 7 C atoms, which is unsubstituted or mono- or polysubstituted by F or Cl, preferably $CF_3$, $C_2F_5$ or $n-C_4F_9$, a component D, preferably in a concentration of 1-20%, comprising one or more optically active and/or chiral compounds, preferably having an HTP≥20 μm$^{-1}$, preferably ≥40 μm$^{-1}$, very particularly preferably ≥60 μm$^{-1}$.

The chiral component D preferably comprises one or more chiral compounds having a mesogenic structure and preferably has one or more mesophases, particularly preferably at least one cholesteric phase. Preferred chiral compounds of component D are, for example, chiral dopants which are known from the prior art and/or are commercially available, such as cholesteryl nonanoate (CN), R/S-811, R/S-1011, R/S-2011, R/S-3011, R/S-4011, R/S-5011 or CB-15 (Merck KGaA, Darmstadt). Particular preference is given to chiral dopants containing one or more chiral groups and one or more mesogenic groups, as disclosed, for example, in DE 34 25 503, DE 35 34 777, DE 35 34 778, DE 35 34 779, DE 35 34 780, DE 43 42 280, EP 01 038 941 and DE 195 41 820. Preference is furthermore given to sorbitols, as described, for example, in WO 98/00428 A1, hydrobenzoins, as described, for example, in GB 2 328 207 A, chiral binaphthols, as described, for example, in WO 02/94805 A1, chiral binaphthol acetals, as described, for example, in WO 02/34739 A1, chiral TADDOLs, as described, for example, in WO 02/06265 A1, or chiral compounds containing fluorinated bridging groups, as described, for example, in WO 02/06196 A1 or WO 02/06195 A1.

The clearing point of the LC medium according to the invention having a blue phase before polymerisation is preferably in the range from 10° C. to 100° C., particularly preferably in the range from 10° C. to 60° C. and very particularly preferably in the range from 20° C. to 40° C.

The LC medium preferably comprises one, two, three, four or more than four chiral compounds. The LC medium preferably comprises chiral compounds in a total concentration of 0.01 to 25%, preferably 0.1-20%, particularly preferably 0.5 to 20%, very particularly 3-15%.

The proportion of the compounds of the formula I in the total content of all polymerisable compounds in the LC medium, or the proportion of the compounds of the formula I in the polymerisable component A), is preferably 20 to 80%, particularly preferably 40 to 60%.

In a further preferred embodiment, the proportion of the compounds of the formula I in the total content of all polymerisable compounds in the LC medium, or the proportion of the compounds of the formula I in the polymerisable component A), is at least 50% and particularly preferably 60% to 100%.

Further particularly preferred embodiments are described below:
the LC medium comprises one, two or three compounds of the formula I;
component B comprises, in addition to the compounds of the formula II, one or more ester compounds of the formula Z:

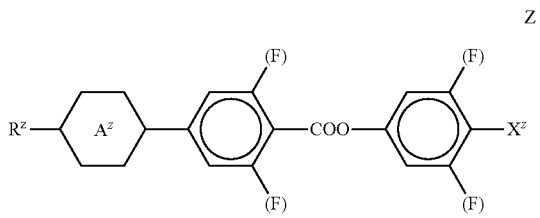

in which $R^z$ has one of the meanings indicated for $R^{22}$ in formula II,

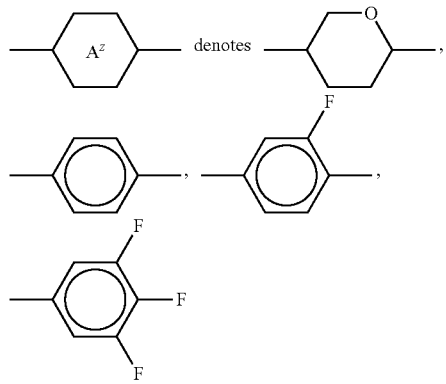

$X^z$ denotes F, Cl, CN, NCS, $OCF_3$, $CF_3$ or $SF_5$, and (F) denotes F or H,
preferably in a concentration of 5 to 35%, particularly preferably 10 to 30%, very particularly preferably 10 to 20%.

Particular preference is given to LC media which, besides one or more compounds of the formula I, comprise one or more compounds of the formula II, in particular in which $X^{22}$ denotes F, Cl, CN, NCS, $CF_3$ or $OCF_3$. The compounds of the formulae I, II, III and Z are colourless, stable and readily miscible with one another or with other liquid-crystalline substances.

The individual components and compounds of the formulae I, II, III and Z of the LC media according to the invention are either known or methods for the preparation thereof can readily be derived from the prior art by the person skilled in the relevant art, since they are based on standard methods described in the literature.

The LC media according to the invention are prepared in a manner conventional per se, for example by mixing one or more of the above-mentioned compounds with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

The LC media according to the invention for LC displays having a blue phase may also comprise further additives known to the person skilled in the art and described in the literature, such as, for example, polymerisation initiators, inhibitors, stabilisers or surface-active substances. These may be polymerisable or unpolymerisable. Polymerisable additives are accordingly ascribed to the polymerisable component. Unpolymerisable additives are accordingly ascribed to the liquid-crystalline component.

The structure of the LC displays according to the invention having a blue phase, with polarisers, electrode substrates and surface-treated electrode layers, corresponds to the conventional structure for displays of this type which is known to the person skilled in the art, as described in the prior art, for example in DE 102 17 273 A1, DE 102 41 301, DE 102 17 273 A1, DE 102 41 301, DE 102 536 06, DE 103 13 979.

An LC display according to the invention preferably comprises the following components:
one or two substrates,
an electrode arrangement having two electrodes on only one of the two substrates or having one electrode on each of the two substrates,
one or two polarisers, and
a layer of an LC medium according to the invention located between the two substrates,
where the display is operated at a temperature at which the LC medium in the unswitched state has an optically isotropic phase, preferably a blue phase.

The phase transition of the LC medium into the blue phase usually takes place starting from a cholesteric phase which exists at lower temperatures than the blue phase. The operating temperature of the LC display according to the invention (i.e. after polymer stabilisation) is preferably above the temperature of the phase transition of the LC medium into the blue phase (i.e. usually the cholesteric phase—blue phase transition), particularly preferably 0.1 to 50°, very particularly preferably 0.5 to 40°, above this phase-transition temperature. Furthermore, the operating temperature of the LC display is preferably below the temperature of the phase transition of the LC medium from the blue phase into the isotropic phase (also known as the clearing point). However, the display can also be operated in the isotropic phase, i.e. above the clearing point.

The LC media according to the invention having a blue phase may, in addition to the above-mentioned compounds of the formulae II and III, and in addition or alternatively to the above-mentioned compounds of the formula Z, also comprise further liquid-crystalline compounds in order, for example, to adapt the physical properties. Such compounds are known to the person skilled in the art. Their concentration in the LC media is preferably 0 to 30%, particularly preferably 0 to 20%, very particularly preferably 5 to 15%.

The liquid-crystalline component of an LC medium according to the invention (i.e. before polymer stabilisation) preferably has a temperature range of the blue phase, or, if a plurality of sequential blue phases occur, a combined temperature range of all blue phases, whose total width is 2° C. or more, preferably 5° C. or more, particularly preferably 10° C. or more, very particularly preferably 20° C. or more.

The liquid-crystalline component of an LC medium according to the invention (i.e. before polymer stabilisation) preferably exhibits a temperature range of the blue phase(s) at least in the range from 30° C. to 60° C., particularly preferably from 30° C. to 70° C., very particularly preferably from 40° C. to 90° C.

"At least" above and below means that the blue phase(s) may also extend below the lower limit value indicated in each case and/or above the upper limit value indicated in each case.

An LC medium according to the invention comprising the polymerised component (i.e. after polymer stabilisation) preferably exhibits a temperature range of the blue phase(s) at least in the range from 30° C. to 70° C., preferably from 20° C. to 70° C., particularly preferably from 0° C. to 80° C., very particularly preferably from −20° C. to 90° C.

The phase-transition temperatures of an LC medium according to the invention comprising the polymerisable component, in particular the clearing point and/or the temperature of the transition from the cholesteric phase into the blue phase (T(Ch,BP), also known as T(N*,BP)), and/or the temperature of the transition from the blue phase into the isotropic phase (T(BP,I)), are preferably not reduced by the polymerisation of the polymerisable component. This means that the polymer stabilisation of the blue phase(s) is preferably carried out in such a way that one or more of the phase-transition temperatures (T(Ch,BP), T(BP,I)) indicated above are not shifted to lower temperatures, i.e. the blue phase(s) is (are) preferably broadened at least to lower temperatures and particularly preferably both to lower and to higher temperatures.

Particularly preferred LC media for use in PSA displays, in particular in PSA-VA, PSA-OCB, PSA-IPS, PSA-FFS or PSA-TN displays, are described below.

An LC medium according to the invention for use in PSA-VA, PSA-OCB, PSA-IPS, PSA-FFS or PSA-TN displays according to the invention preferably comprises:
- <5%, particularly preferably <1%, very particularly preferably <0.5%, of the polymerisable component,
- >95%, particularly preferably >99%, of the liquid-crystalline component,
- <5% by weight, particularly preferably <1% by weight, very particularly preferably <0.5% by weight, of polymerisable compounds, in particular polymerisable compounds of the formula I mentioned above or sub-formulae thereof,
- one, two or three polymerisable compounds of the formula I or sub-formulae thereof according to the invention,
- a polymerisable component which comprises exclusively polymerisable compounds of the formula I or sub-formulae thereof according to the invention,
- a liquid-crystalline component which is an LC compound or an LC mixture which has a nematic liquid-crystal phase,
- a polymerisable and/or liquid-crystalline component which comprises exclusively achiral compounds,
- a polymerisable component which comprises one or more polymerisable compounds containing one polymerisable group (monoreactive) and one or more polymerisable compounds according to the invention containing two or more, preferably two, polymerisable groups (di- or multireactive), preferably selected from compounds of the formula I or sub-formulae thereof, and optionally from the above-mentioned comonomers selected from the list comprising the formulae M1-M29,
- a polymerisable component which comprises exclusively polymerisable compounds according to the invention containing two polymerisable groups (direactive), preferably selected from compounds of the formula I or sub-formulae thereof, and optionally additionally from the above-mentioned comonomers from the list comprising the formulae M1-M29,
- apart from the polymerisable compounds according to the invention, in particular of the formula I or sub-formulae thereof, and the comonomers, no compounds which contain a terminal vinyloxy group (—O—CH=CH$_2$),
- 1 to 5, preferably 1, 2 or 3, polymerisable compounds, preferably selected from polymerisable compounds according to the invention, in particular of the formula I or sub-formulae thereof.

Particularly preferred LC media for use in PSA-VA displays are indicated below:

a) LC medium which comprises one or more compounds of the formulae CY and/or PY:

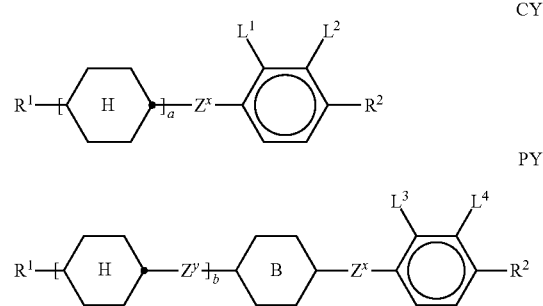

in which the individual radicals have the following meanings:
a denotes 1 or 2,
b denotes 0 or 1,

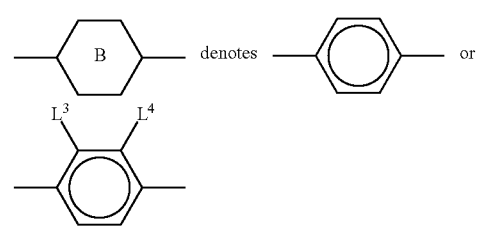

$R^1$ and $R^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, $Z^x$ and $Z^y$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, $L^{1-4}$ each, independently of one another, denote F, Cl, OCF$_3$, CF$_3$, CH$_3$, CH$_2$F, CHF$_2$.

Preferably, both radicals $L^1$ and $L^2$ denote F or one of the radicals $L^1$ and $L^2$ denotes F and the other denotes Cl, or both radicals $L^3$ and $L^4$ denote F or one of the radicals $L^3$ and $L^4$ denotes F and the other denotes Cl.

The compounds of the formula CY are preferably selected from the group consisting of the following sub-formulae:

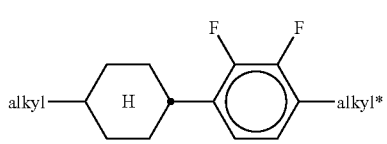
CY1

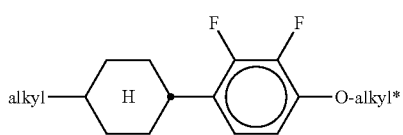
CY2

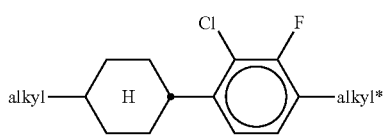
CY3

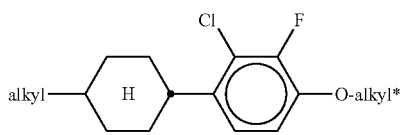
CY4

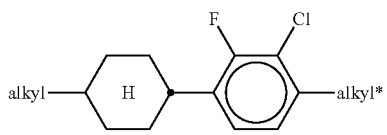
CY5

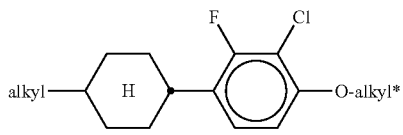
CY6

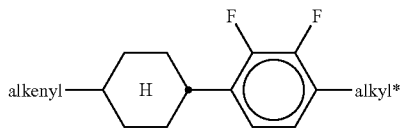
CY7

-continued

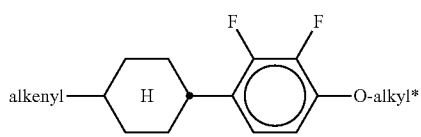
CY8

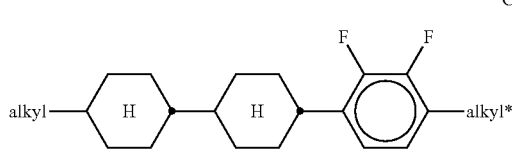
CY9

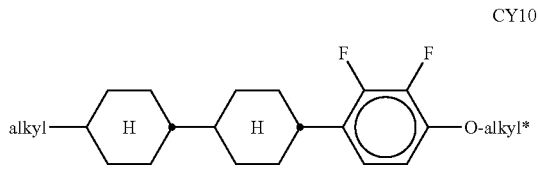
CY10

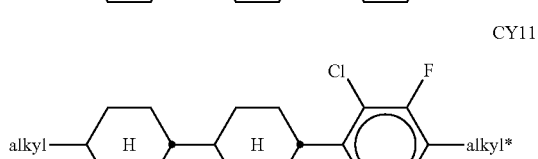
CY11

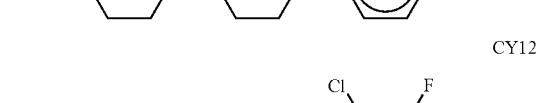
CY12

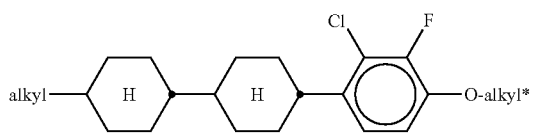
CY13

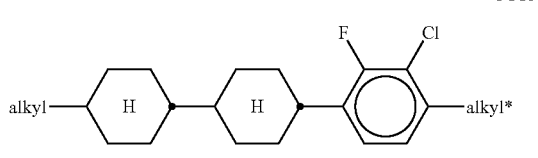
CY14

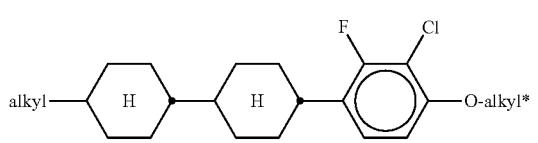
CY15

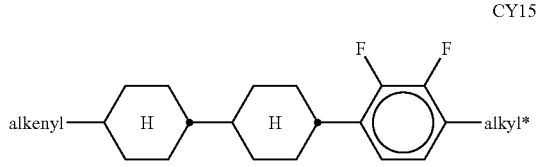
CY16

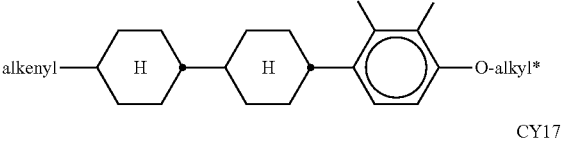
CY17

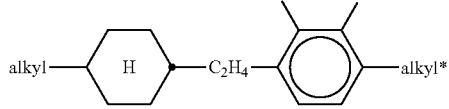

CY18
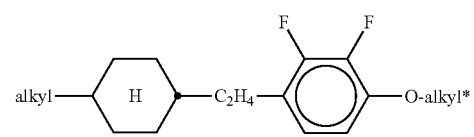

CY19
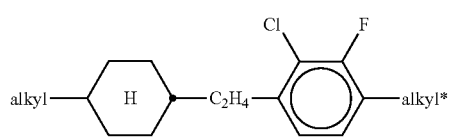

CY20
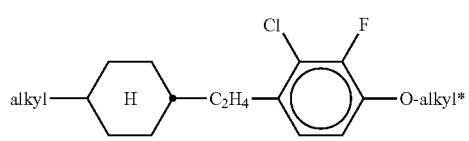

CY21
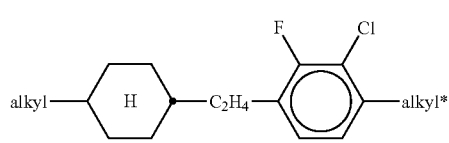

CY22
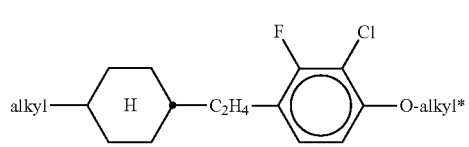

CY23
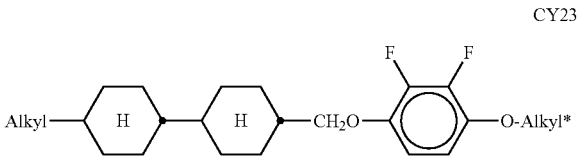

CY24
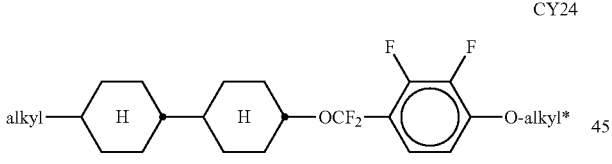

CY25
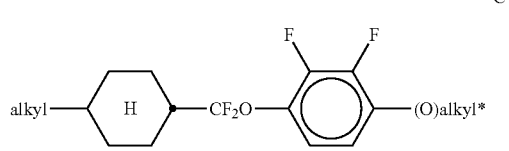

CY25
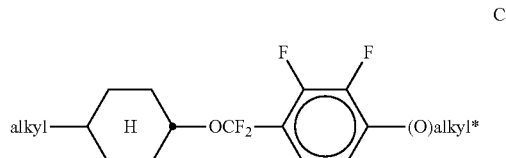

CY26
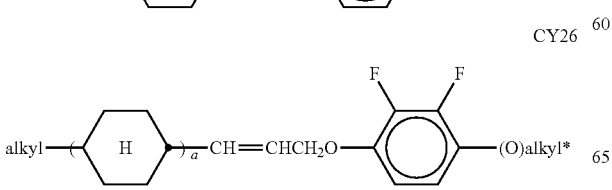

CY27
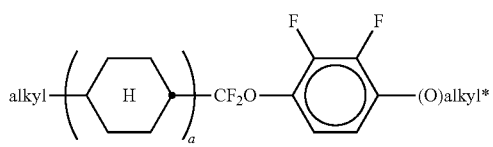

CY28
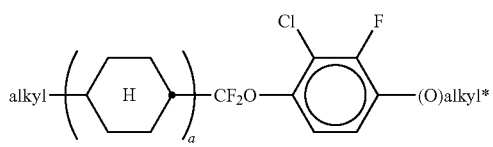

in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:

PY1
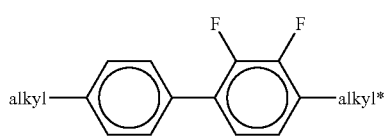

PY2
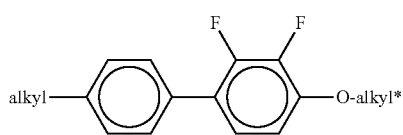

PY3
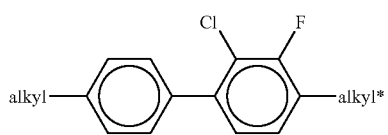

PY4
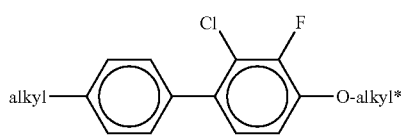

PY5
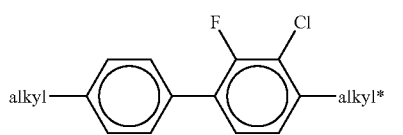

PY6
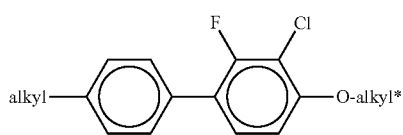

PY7
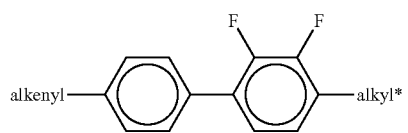

PY8
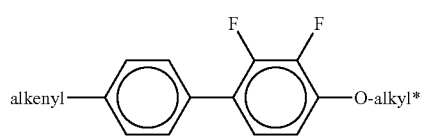

PY9
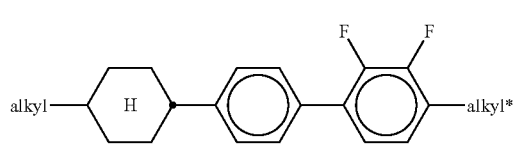

PY10
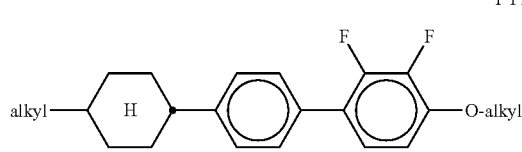

PY11
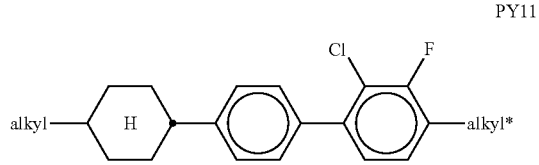

PY12
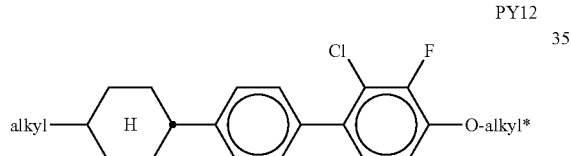

PY13
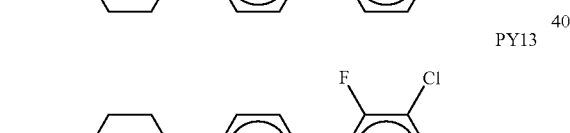

PY14
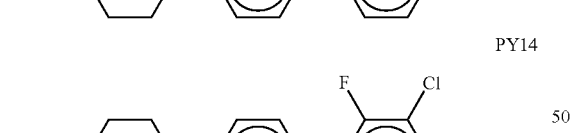

PY15
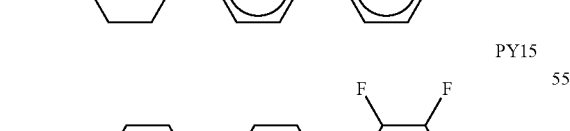

PY16
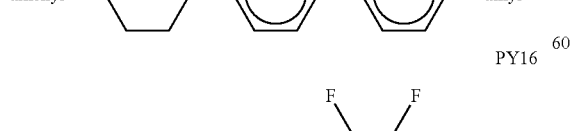

PY17
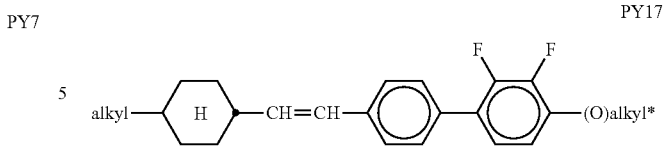

PY18
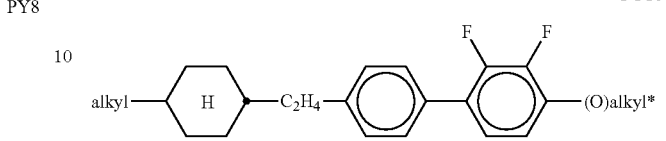

PY19
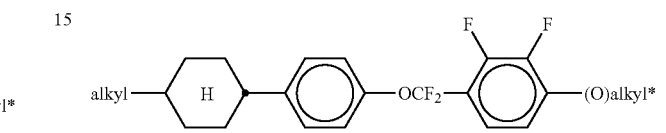

PY20
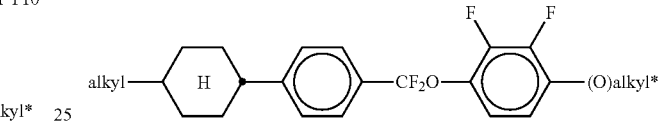

in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

b) LC medium which additionally comprises one or more compounds of the following formula:

ZK
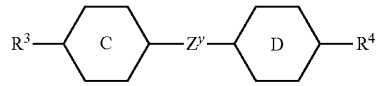

in which the individual radicals have the following meanings:

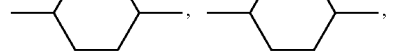

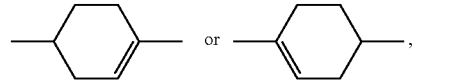

$R^3$ and $R^4$ each, independently of one another, denote alkyl having 1 to 12 C atoms, in which, in addition, one or two non-adjacent $CH_2$ groups may be replaced by —O—, —CH=CH—, —CO—, —O—CO— or —CO—O— in such a way that O atoms are not linked directly to one another, $Z^y$ denotes —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond.

The compounds of the formula ZK are preferably selected from the group consisting of the following sub-formulae:

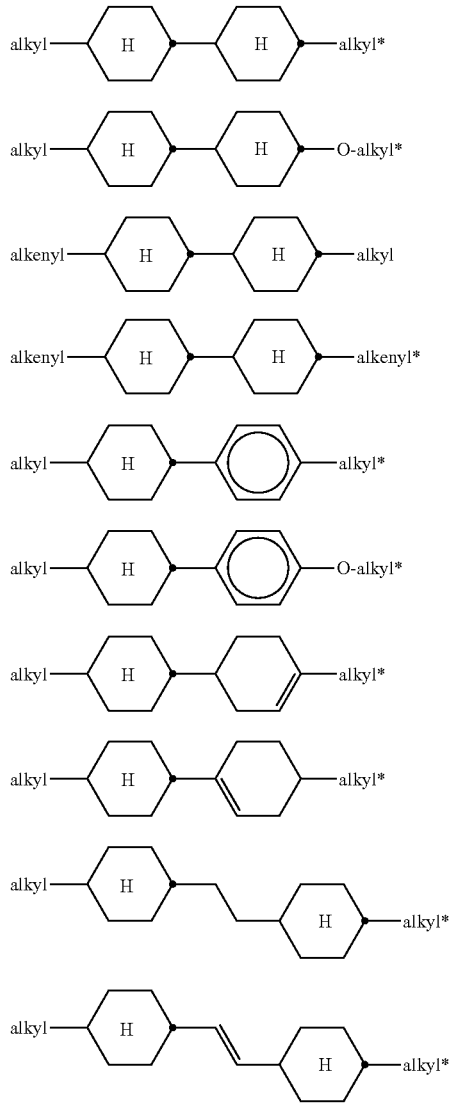

ZK1
ZK2
ZK3
ZK4
ZK5
ZK6
ZK7
ZK8
ZK9
ZK10 in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2$=CH—, $CH_2$=$CHCH_2CH_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

c) LC medium which additionally comprises one or more compounds of the following formula:

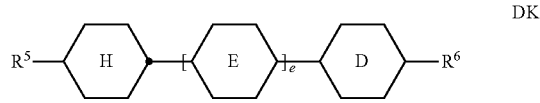

DK in which the individual radicals on each occurrence, identically or differently, have the following meanings:
$R^5$ and $R^6$ each, independently of one another, have one of the meanings indicated above for $R^1$,

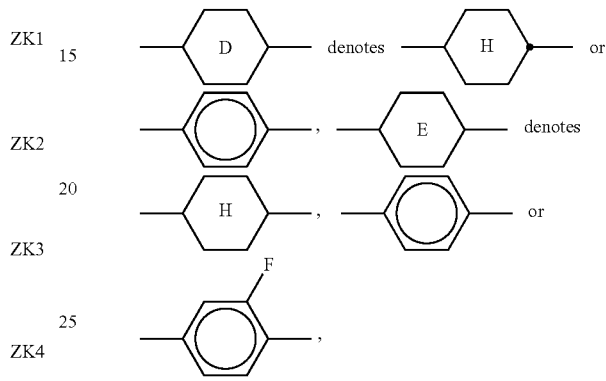

and
e denotes 1 or 2.

The combination of compounds of the preferred embodiments a)-c) mentioned above with the polymerised compounds described above causes low threshold voltages, low rotational viscosities and very good low-temperature stabilities in the LC media according to the invention at the same time as constantly high clearing points and high HR values, and allows the rapid establishment of a particularly low pretilt angle in PSA displays. In particular, the LC media exhibit significantly shortened response times, in particular also the grey-shade response times, in PSA displays compared with the media from the prior art.

LC media according to the invention for use in displays of the PSA-VA type have negative dielectric anisotropy $\Delta\epsilon$, preferably of about −0.5 to −10, in particular of about −2.5 to −7.5, at 20° C. and 1 kHz.

In VA-type displays according to the invention, the molecules in the layer of the LC medium in the switched-off state are aligned perpendicular to the electrode surfaces (homeotropically) or have a tilted homeotropic alignment. On application of an electrical voltage to the electrodes, a realignment of the LC molecules takes place with the longitudinal molecular axes parallel to the electrode surfaces.

The birefringence $\Delta n$ in LC media according to the invention for use in displays of the VA type is preferably less than 0.16, particularly preferably between 0.06 and 0.14, in particular between 0.07 and 0.12.

The LC media according to the invention may also comprise further additives known to the person skilled in the art and described in the literature, such as, for example, polymerisation initiators, inhibitors, stabilisers, surface-active substances or chiral dopants. These may be polymerisable or unpolymerisable. Polymerisable additives are accordingly ascribed to the polymerisable component. Unpolymerisable additives are accordingly ascribed to the liquid-crystalline component.

The LC media may, for example, comprise one or more chiral dopants, preferably those selected from the group consisting of compounds from Table B below.

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutylammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-c) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes.

The structure of the PSA displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PSA-VA displays are described, for example, in US 2006/0066793 A1.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

The following abbreviations are used:
(n, m, z: in each case, independently of one another, 1, 2, 3, 4, 5 or 6)

TABLE A

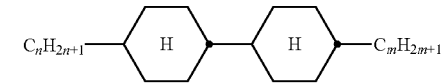

CCH-nm

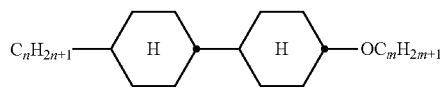

CCH-nOm

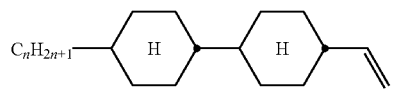

CC-n-V

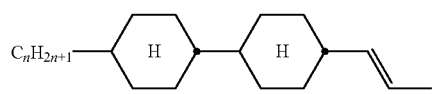

CC-n-V1

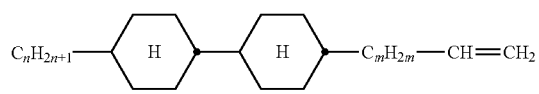

CC-n-mV

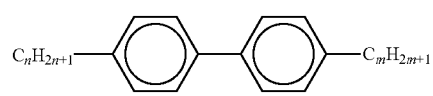

PP-n-m

TABLE A-continued
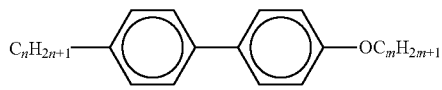
PP-n-Om
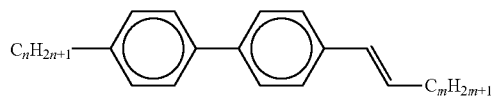
PP-n-Vm
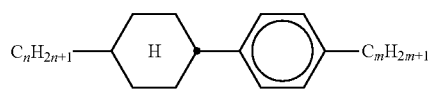
PCH-nm
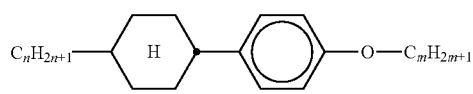
PCH-nOm
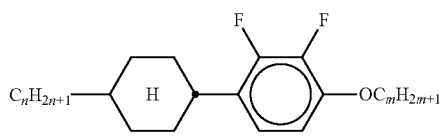
CY-n-Om
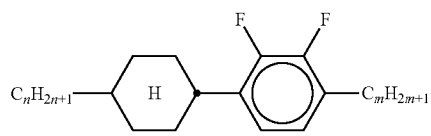
CY-n-m
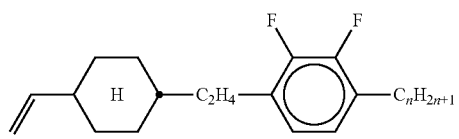
CEY-V-m
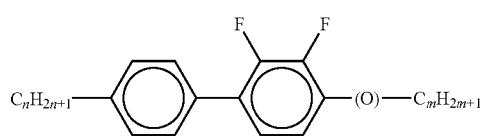
PY-n-(O)m
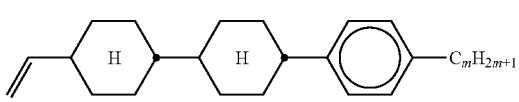
CCP-V-m
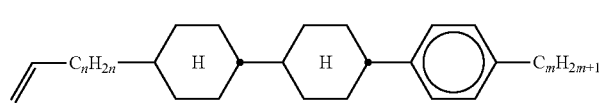
CCP-Vn-m TABLE A-continued
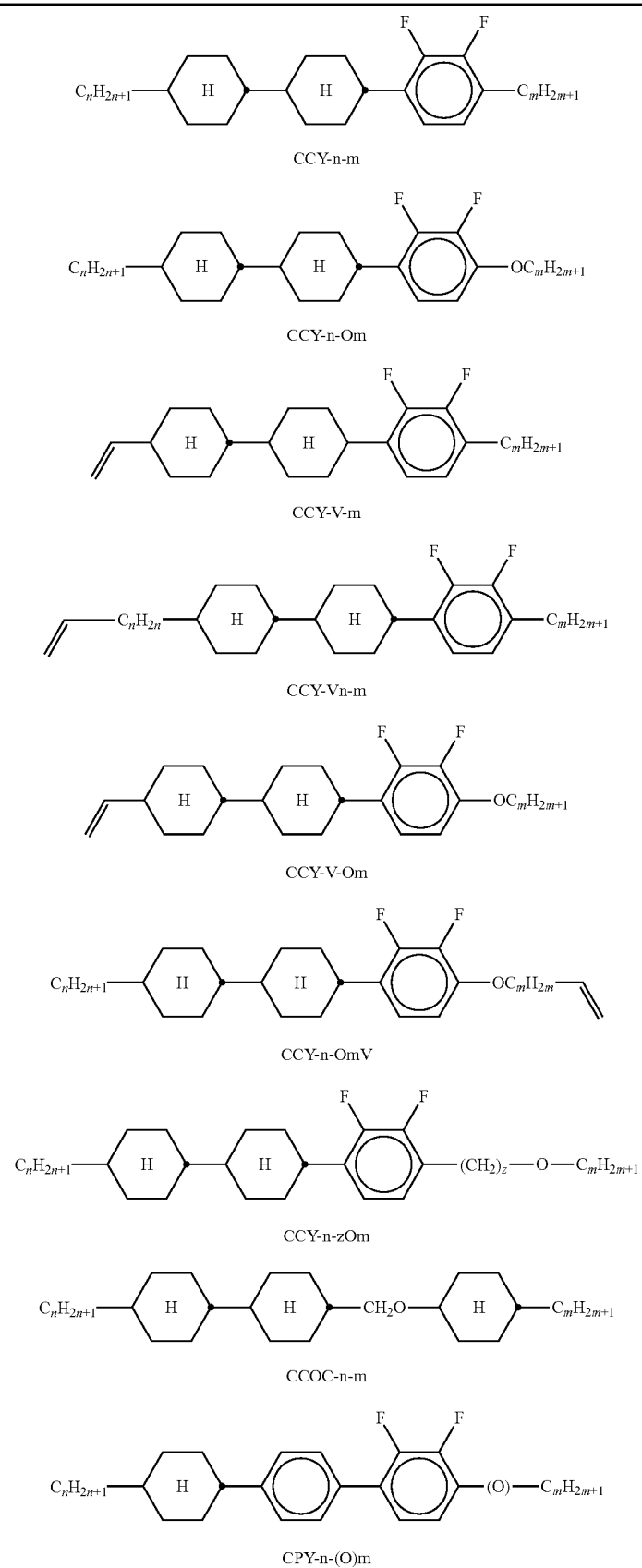

TABLE A-continued
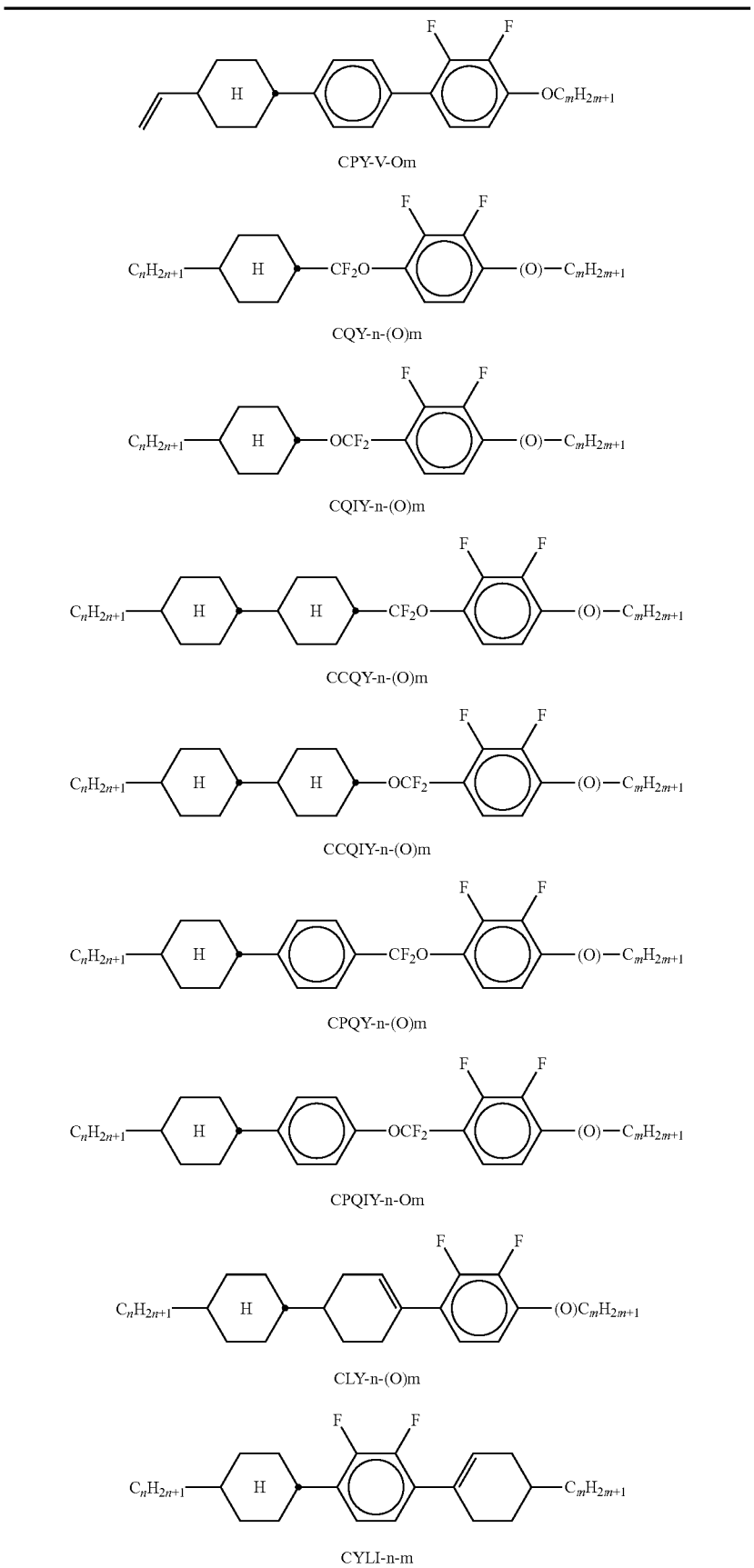

TABLE A-continued
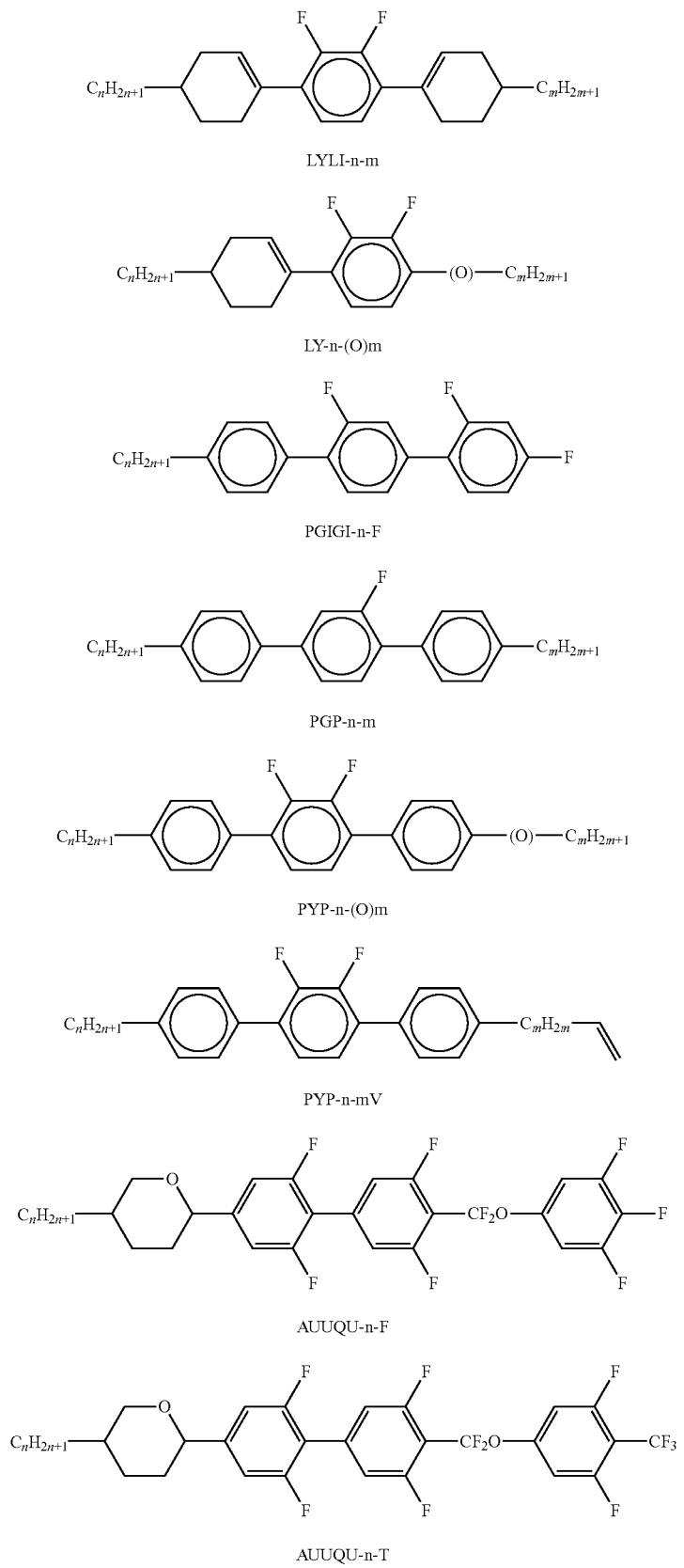

TABLE A-continued
AUUQU-n-OT
AUUQU-n-N
AUUQGU-n-F
AGUQU-n-F
PUQU-n-F
PUZU-n-F
In a preferred embodiment of the present invention, the LC media according to the invention comprise one or more compounds selected from the group consisting of compounds from Table A.
TABLE B
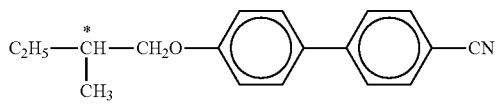

TABLE B-continued
C15
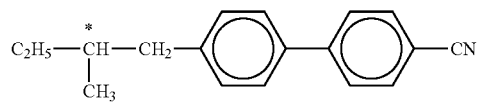
CB15
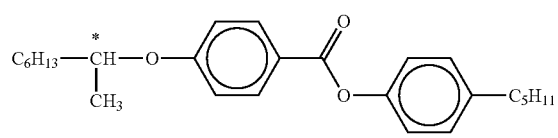
CM21
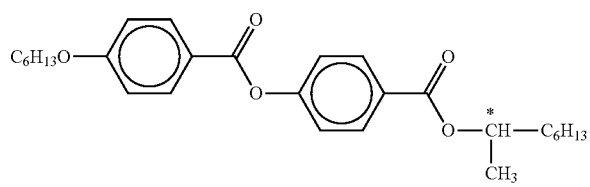
R/S-811
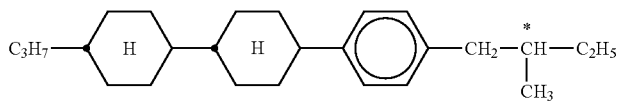
CM44
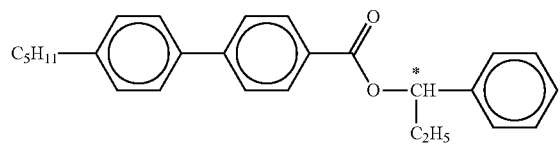
CM45
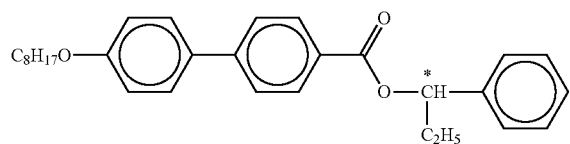
CM47
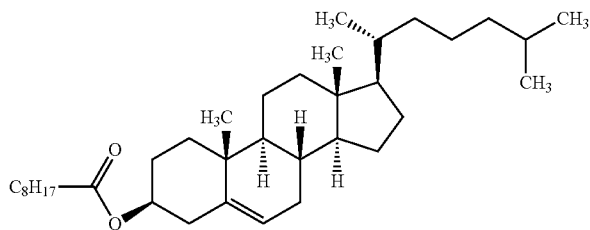
CN
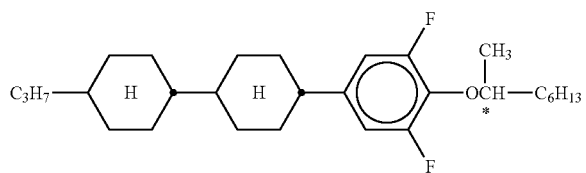

TABLE B-continued
R/S-2011
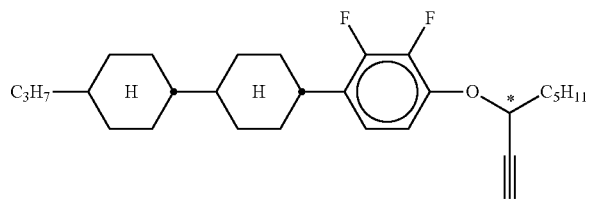
R/S-3011
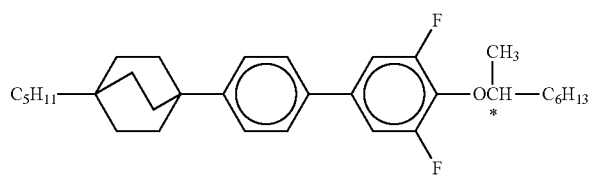
R/S-4011
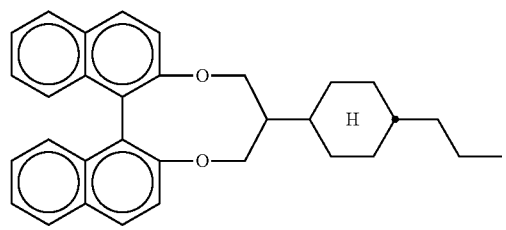
R/S-5011
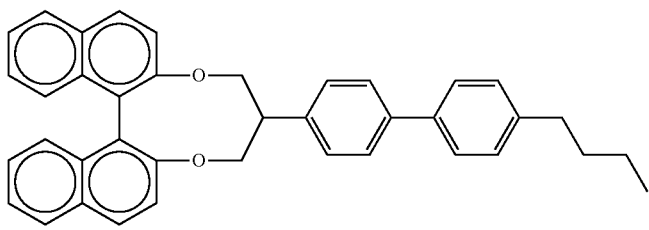
R/S
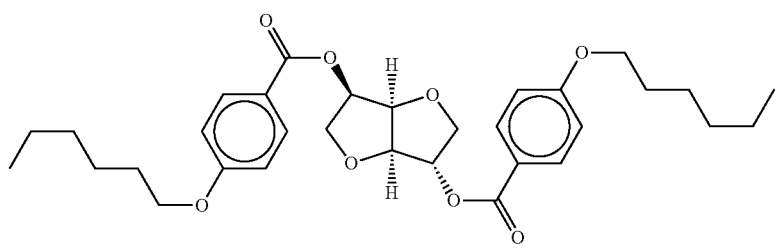
R/S
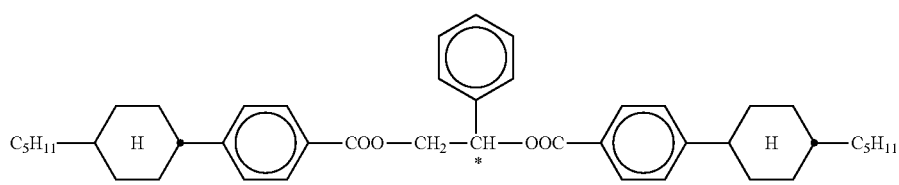
R/S-1011

Table B shows possible chiral dopants which can be added to the LC media according to the invention.
The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.
TABLE C
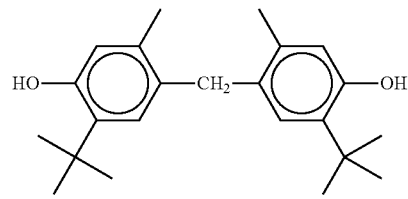
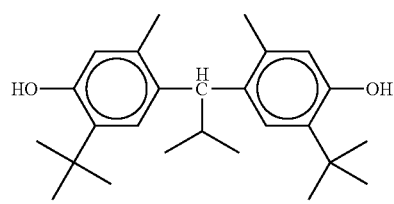
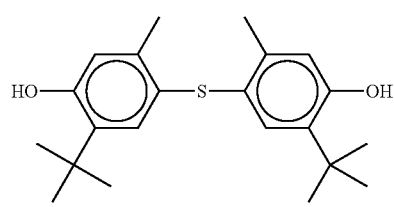
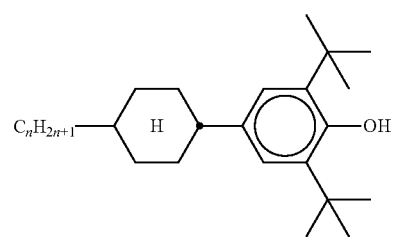
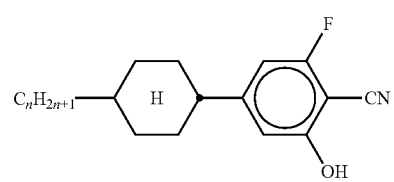
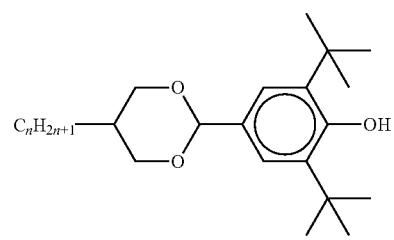

TABLE C-continued
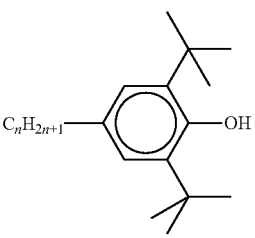
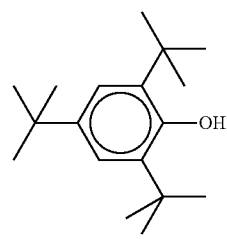
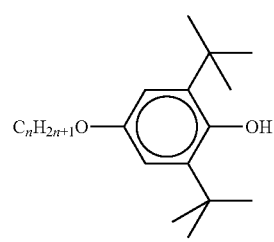
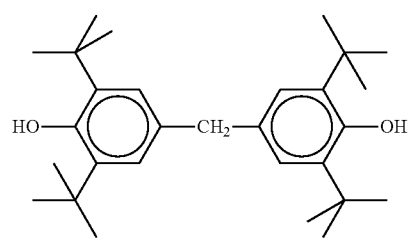
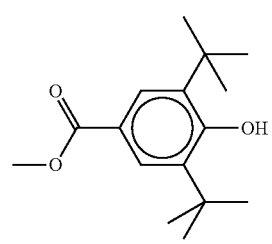
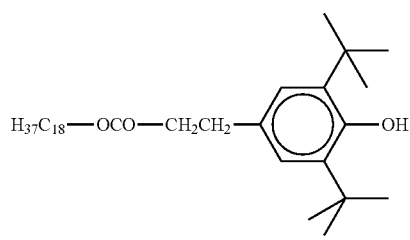

TABLE C-continued
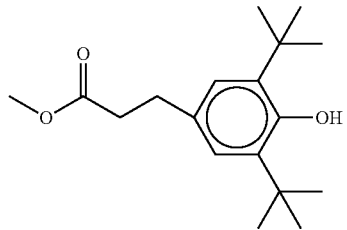
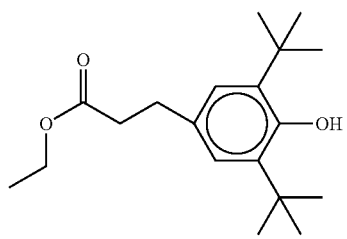
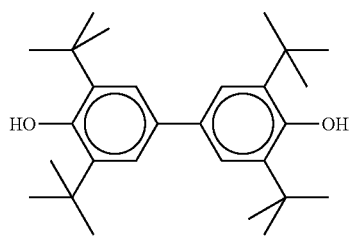
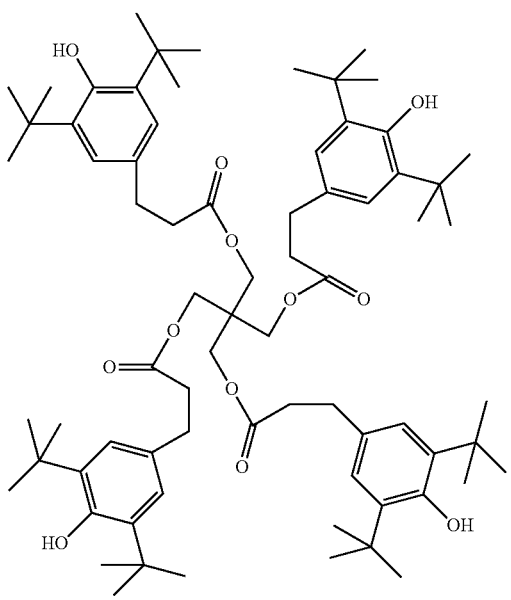 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
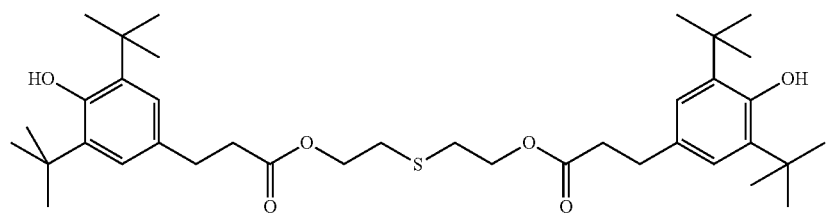 [SMILES: CC(C)(C)c1cc(CCC(=O)OCCSCCOC(=O)CCc2cc(C(C)(C)C)c(O)c(C(C)(C)C)c2)cc(C(C)(C)C)c1O]

TABLE C-continued
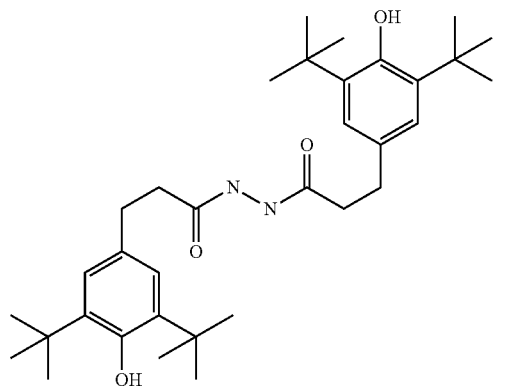 [SMILES: CC(C)(C)c1cc(CCC(=O)NNC(=O)CCc2cc(C(C)(C)C)c(O)c(C(C)(C)C)c2)cc(C(C)(C)C)c1O]
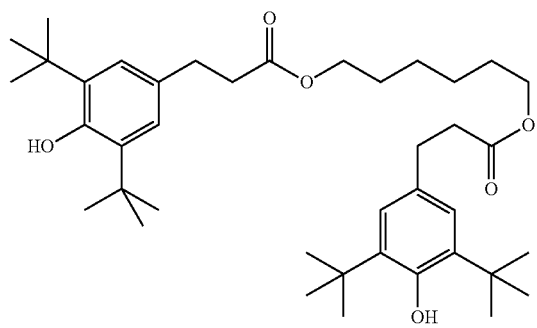 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
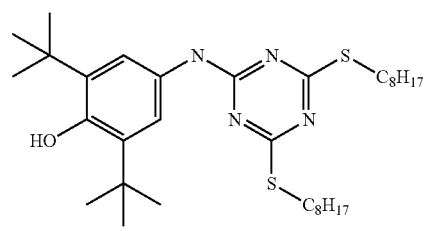
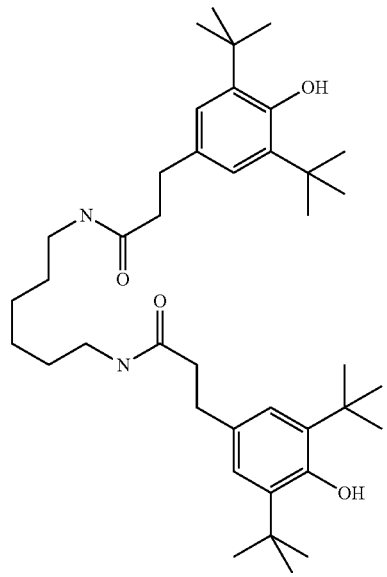 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]

TABLE C-continued
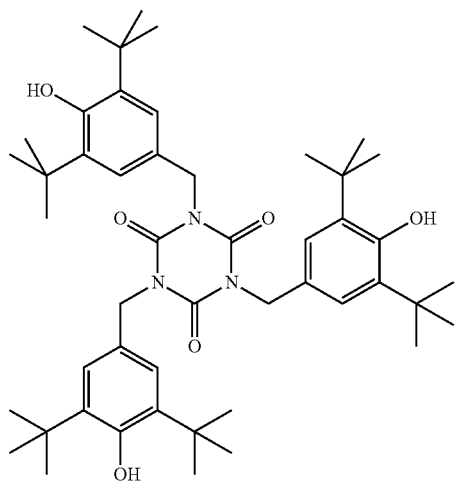 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
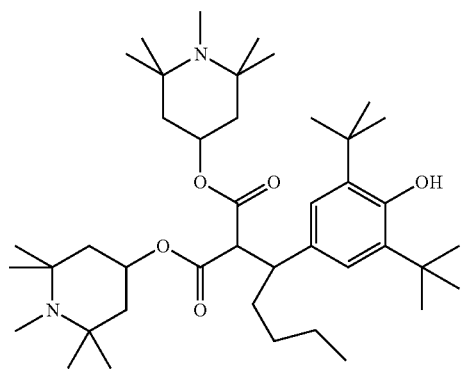 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]
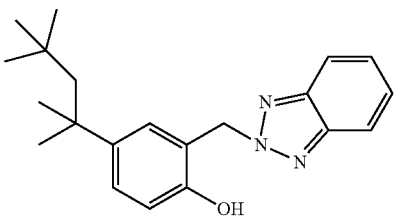 [SMILES: CC(C)(C)CC(C)(C)c1ccc(O)c(Cn2nc3ccccc3n2)c1]
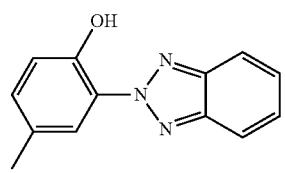 [SMILES: Cc1ccc(O)c(-n2nc3ccccc3n2)c1]
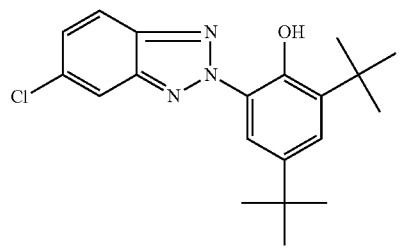 [SMILES: CC(C)(C)c1cc(-n2nc3ccc(Cl)cc3n2)c(O)c(C(C)(C)C)c1]

TABLE C-continued
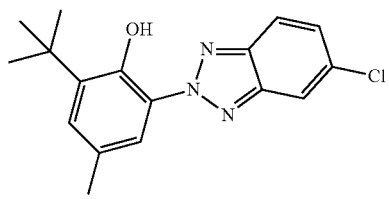 [SMILES: Cc1cc(-n2nc3ccc(Cl)cc3n2)c(O)c(C(C)(C)C)c1]
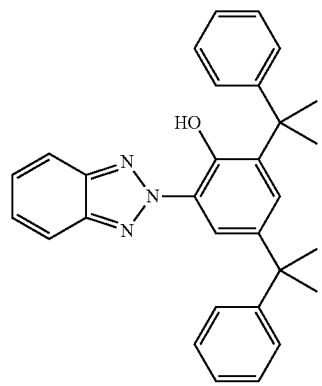 [SMILES: CC(C)(c1ccccc1)c1cc(-n2nc3ccccc3n2)c(O)c(C(C)(C)c2ccccc2)c1]
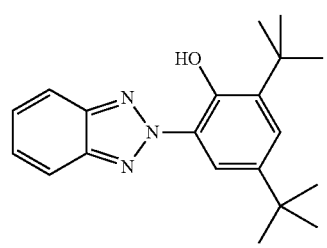 [SMILES: CC(C)(C)c1cc(-n2nc3ccccc3n2)c(O)c(C(C)(C)C)c1]
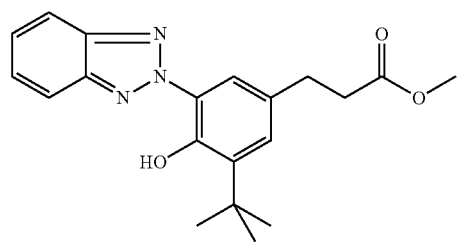 [SMILES: COC(=O)CCc1cc(-n2nc3ccccc3n2)c(O)c(C(C)(C)C)c1]
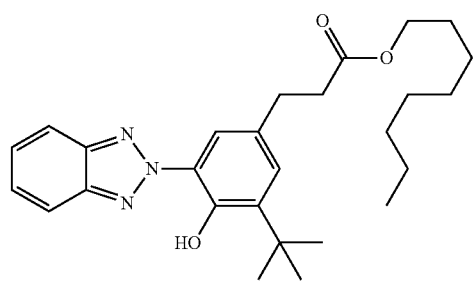 [SMILES: CCCCCCCCOC(=O)CCc1cc(-n2nc3ccccc3n2)c(O)c(C(C)(C)C)c1]

TABLE C-continued
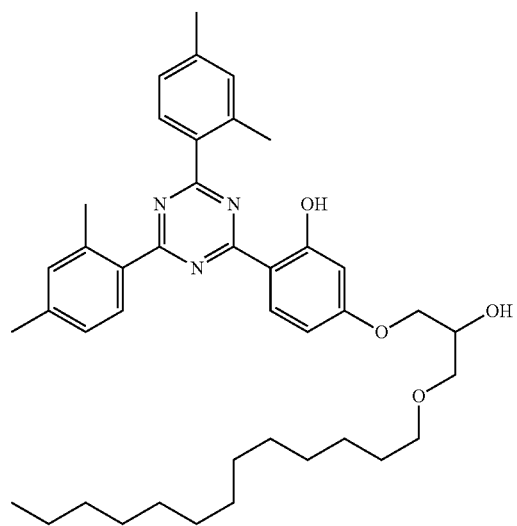 [SMILES: CCCCCCCCCCCCCOCC(O)COc1ccc(-c2nc(-c3ccc(C)cc3C)nc(-c3ccc(C)cc3C)n2)c(O)c1]
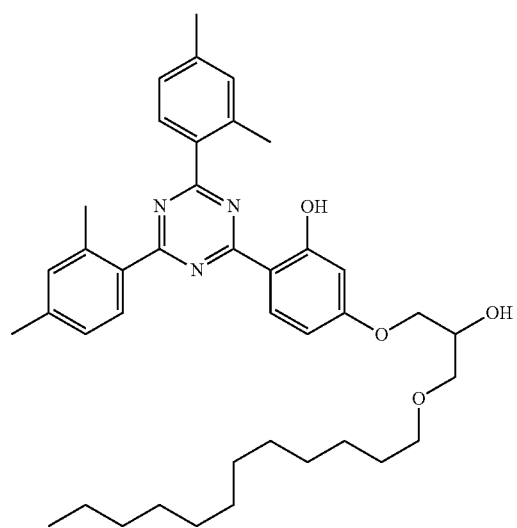 [SMILES: CCCCCCCCCCCCOCC(O)COc1ccc(-c2nc(-c3ccc(C)cc3C)nc(-c3ccc(C)cc3C)n2)c(O)c1]
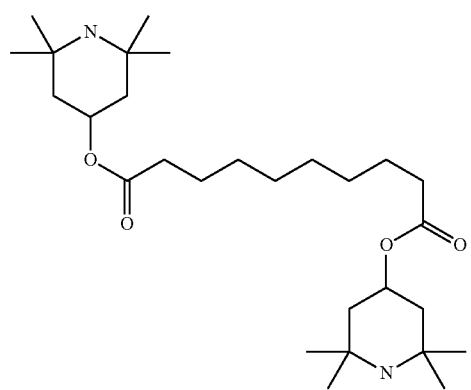

TABLE C-continued

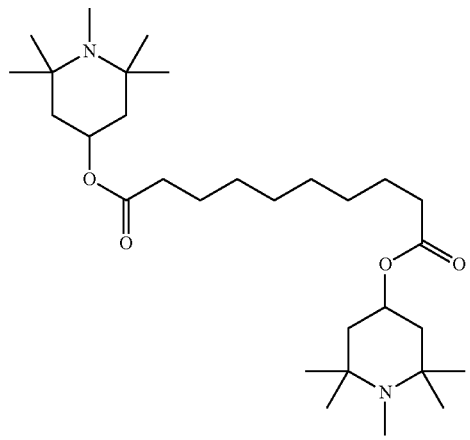

20

Table C shows possible stabilisers which can be added to the LC media according to the invention.

(n here denotes an integer from 1 to 12, preferably 1, 2, 3, 4, 5, 6, 7 or 8, terminal methyl groups are not shown).

The LC media preferably comprise 0 to 10% by weight, in particular 1 ppm to 5% by weight, particularly preferably 1 ppm to 1% by weight, of stabilisers. The LC media preferably comprise one or more stabilisers selected from the group consisting of compounds from Table C.

TABLE D

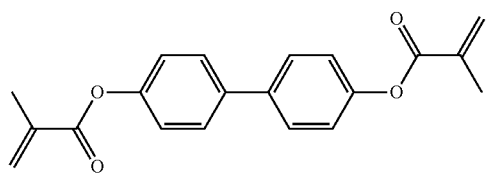 [SMILES: C=C(C)C(=O)Oc1ccc(-c2ccc(OC(=O)C(=C)C)cc2)cc1]

RM-1

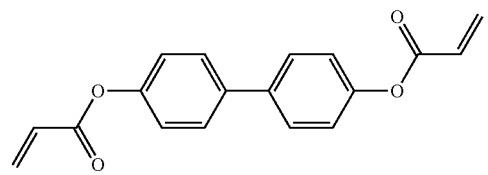 [SMILES: C=CC(=O)Oc1ccc(-c2ccc(OC(=O)C=C)cc2)cc1]

RM-2

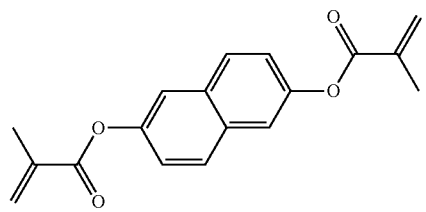 [SMILES: C=C(C)C(=O)Oc1ccc2cc(OC(=O)C(=C)C)ccc2c1]

RM-3

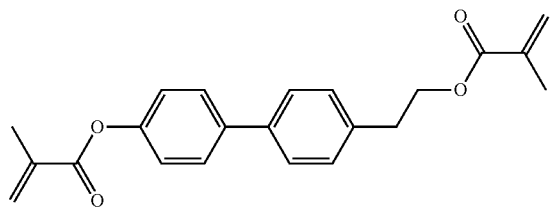 [SMILES: C=C(C)C(=O)OCCc1ccc(-c2ccc(OC(=O)C(=C)C)cc2)cc1]

RM-4

TABLE D-continued
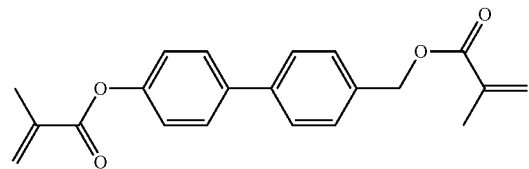 [SMILES: C=C(C)C(=O)OCc1ccc(-c2ccc(OC(=O)C(=C)C)cc2)cc1]
RM-5
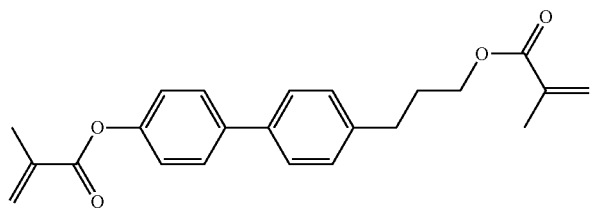 [SMILES: C=C(C)C(=O)OCCCc1ccc(-c2ccc(OC(=O)C(=C)C)cc2)cc1]
RM-6
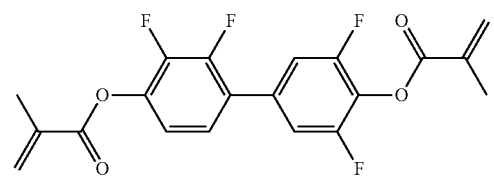 [SMILES: C=C(C)C(=O)Oc1ccc(-c2cc(F)c(OC(=O)C(=C)C)c(F)c2)c(F)c1F]
RM-7
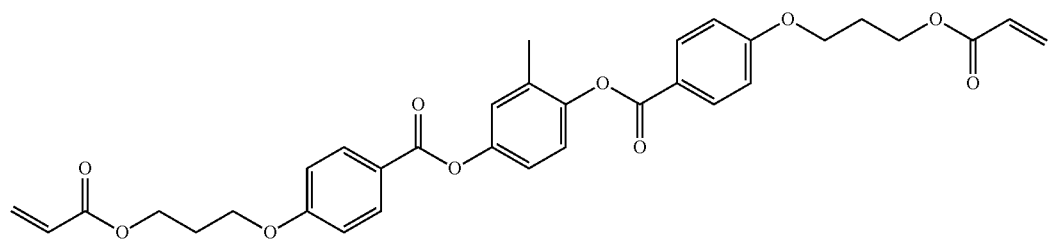 [SMILES: C=CC(=O)OCCCOc1ccc(C(=O)Oc2ccc(OC(=O)c3ccc(OCCCOC(=O)C=C)cc3)c(C)c2)cc1]
RM-8
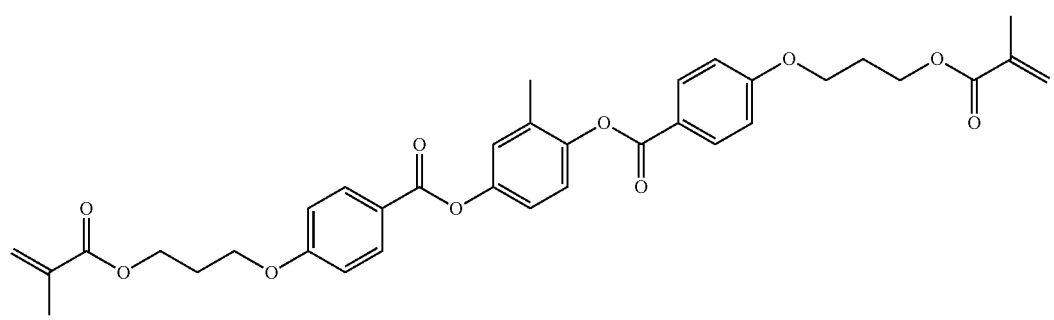 [SMILES: C=C(C)C(=O)OCCCOc1ccc(C(=O)Oc2ccc(OC(=O)c3ccc(OCCCOC(=O)C(=C)C)cc3)c(C)c2)cc1]
RM-9
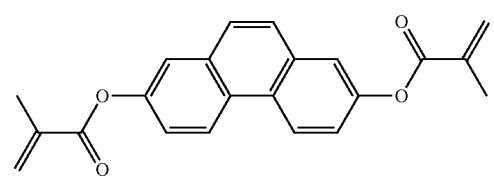 [SMILES: C=C(C)C(=O)Oc1ccc2c(ccc3cc(OC(=O)C(=C)C)ccc32)c1]
RM-10

TABLE D-continued
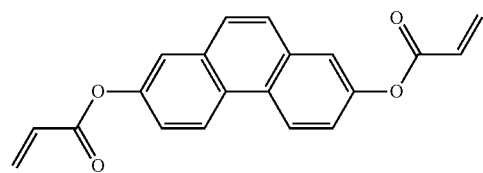
RM-11
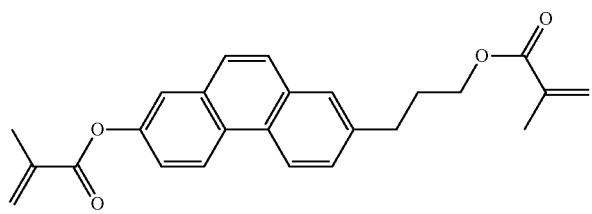 [SMILES: C=C(C)C(=O)OCCCc1ccc2c(ccc3cc(OC(=O)C(=C)C)ccc32)c1]
RM-12
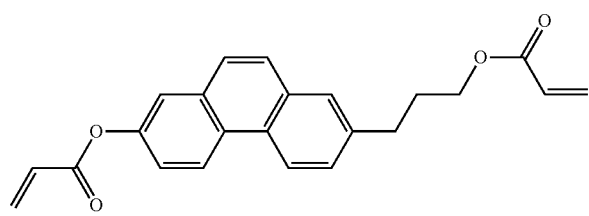 [SMILES: C=CC(=O)OCCCc1ccc2c(ccc3cc(OC(=O)C=C)ccc32)c1]
RM-13
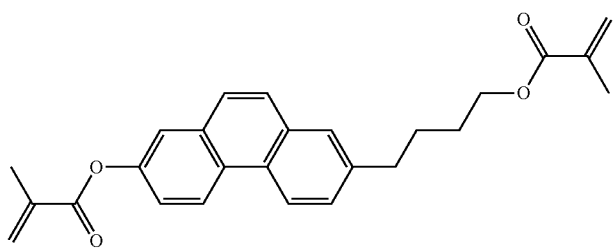 [SMILES: C=C(C)C(=O)OCCCCc1ccc2c(ccc3cc(OC(=O)C(=C)C)ccc32)c1]
RM-14
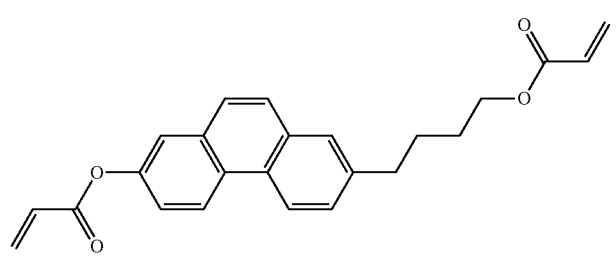 [SMILES: C=CC(=O)OCCCCc1ccc2c(ccc3cc(OC(=O)C=C)ccc32)c1]
RM-15
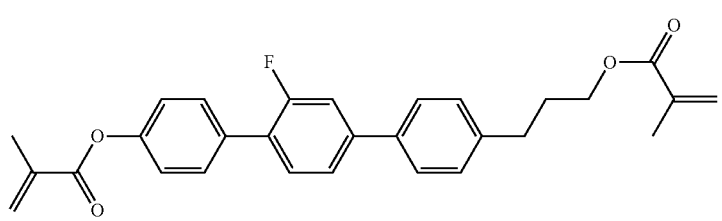 [SMILES: C=C(C)C(=O)OCCCc1ccc(-c2ccc(-c3ccc(OC(=O)C(=C)C)cc3)c(F)c2)cc1]
RM-16

TABLE D-continued
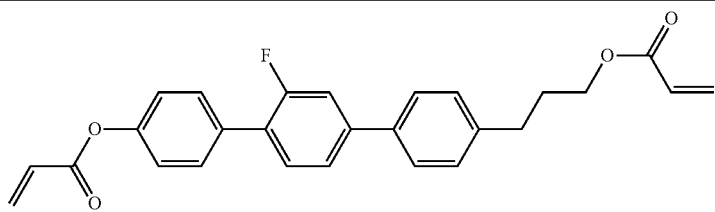
RM-17
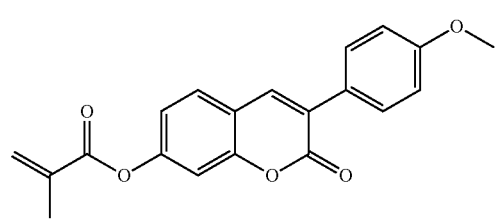 [SMILES: C=C(C)C(=O)Oc1ccc2cc(-c3ccc(OC)cc3)c(=O)oc2c1]
RM-18
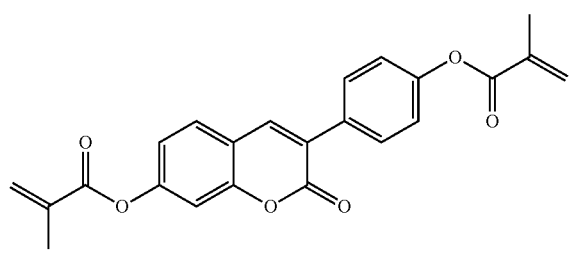 [SMILES: C=C(C)C(=O)Oc1ccc(-c2cc3ccc(OC(=O)C(=C)C)cc3oc2=O)cc1]
RM-19
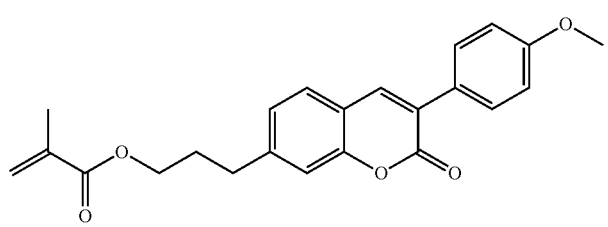 [SMILES: C=C(C)C(=O)OCCCc1ccc2cc(-c3ccc(OC)cc3)c(=O)oc2c1]
RM-20
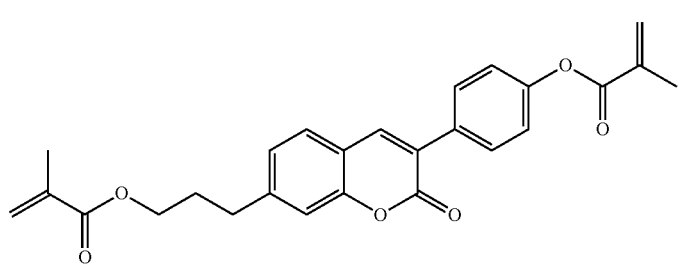 [SMILES: C=C(C)C(=O)OCCCc1ccc2cc(-c3ccc(OC(=O)C(=C)C)cc3)c(=O)oc2c1]
RM-21
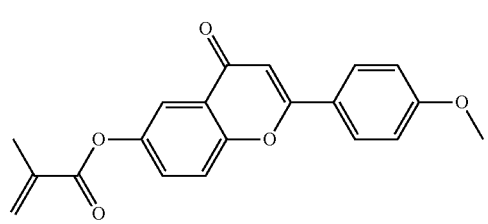 [SMILES: C=C(C)C(=O)Oc1ccc2oc(-c3ccc(OC)cc3)cc(=O)c2c1]
RM-22

TABLE D-continued
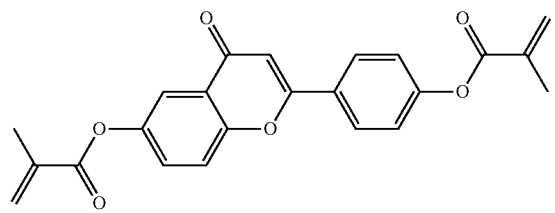 [SMILES: C=C(C)C(=O)Oc1ccc(-c2cc(=O)c3cc(OC(=O)C(=C)C)ccc3o2)cc1]
RM-23
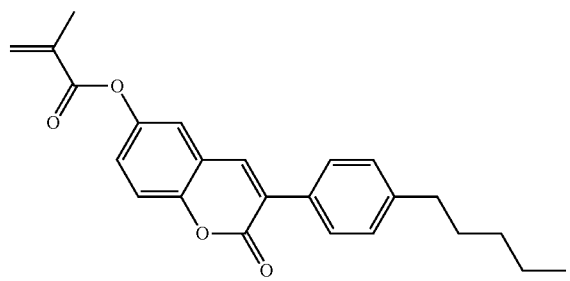 [SMILES: C=C(C)C(=O)Oc1ccc2oc(=O)c(-c3ccc(CCCCC)cc3)cc2c1]
RM-24
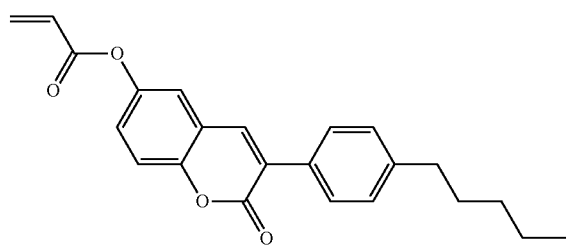 [SMILES: C=CC(=O)Oc1ccc2oc(=O)c(-c3ccc(CCCCC)cc3)cc2c1]
RM-25
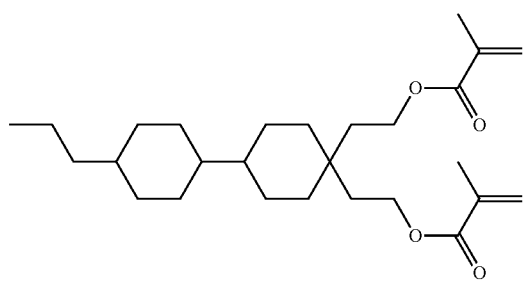 [SMILES: C=C(C)C(=O)OCCC1(CCOC(=O)C(=C)C)CCC(C2CCC(CCC)CC2)CC1]
RM-26
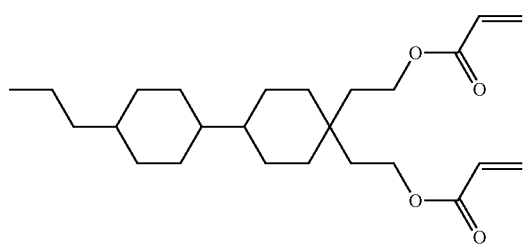 [SMILES: C=CC(=O)OCCC1(CCOC(=O)C=C)CCC(C2CCC(CCC)CC2)CC1]
RM-27

TABLE D-continued
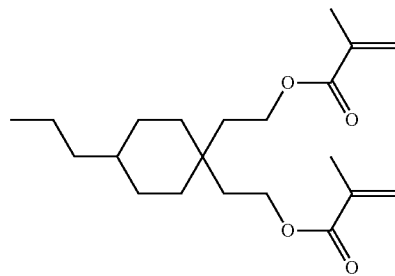 [SMILES: C=C(C)C(=O)OCCC1(CCOC(=O)C(=C)C)CCC(CCC)CC1]
RM-28
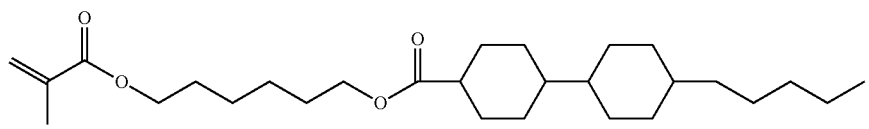
RM-29
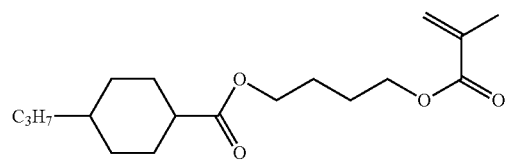
RM-30
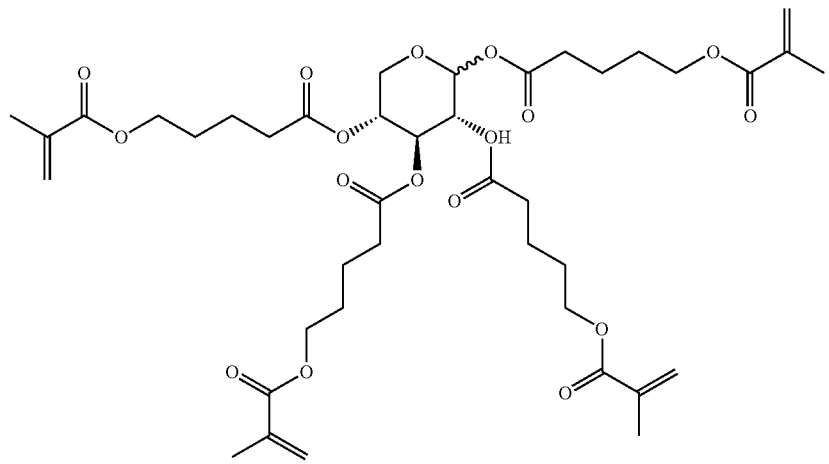 [SMILES: C=C(C)C(=O)OCCCCC(=O)OC1OC[C@@H](OC(=O)CCCCOC(=O)C(=C)C)[C@H](OC(=O)CCCCOC(=O)C(=C)C)[C@H]1OC(=O)CCCCOC(=O)C(=C)C]
RM-31

TABLE D-continued

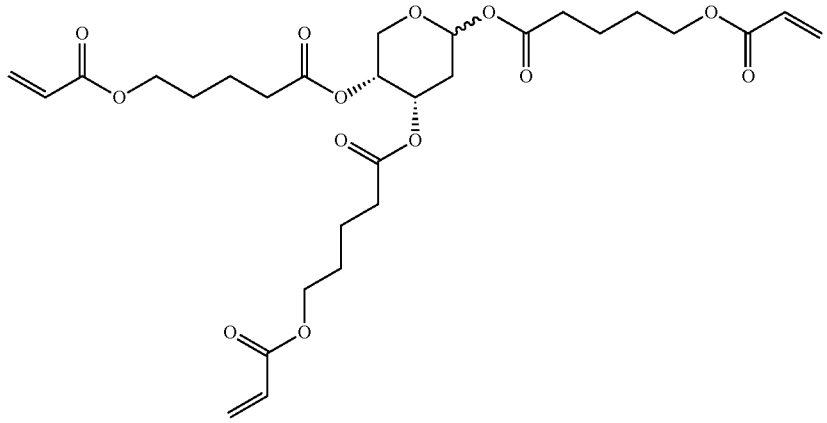 [SMILES: C=CC(=O)OCCCCC(=O)OC1C[C@H](OC(=O)CCCCOC(=O)C=C)[C@H](OC(=O)CCCCOC(=O)C=C)CO1]

RM-32

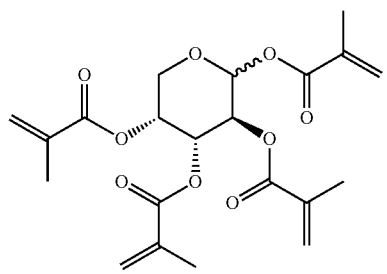 [SMILES: C=C(C)C(=O)OC1OC[C@@H](OC(=O)C(=C)C)[C@@H](OC(=O)C(=C)C)[C@@H]1OC(=O)C(=C)C]

RM-33

Table D shows illustrative compounds which can be used in the LC media in accordance with the present invention, preferably as reactive mesogenic compounds.

In a preferred embodiment of the present invention, the mesogenic media comprise one or more compounds selected from the group of the compounds from Table D.

In addition, the following abbreviations and symbols are used:
$V_0$ threshold voltage, capacitive [V] at 20° C.,
$n_e$ extraordinary refractive index at 20° C. and 589 nm,
$n_o$ ordinary refractive index at 20° C. and 589 nm,
$\Delta n$ optical anisotropy at 20° C. and 589 nm,
$\epsilon_\perp$ dielectric permittivity perpendicular to the director at 20° C. and 1 kHz,
$\epsilon_\parallel$ dielectric permittivity parallel to the director at 20° C. and 1 kHz,
$\Delta\epsilon$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application are quoted in per cent by weight and relate to the corresponding mixture as a whole, comprising all solid or liquid-crystalline components, without solvents.

Unless explicitly noted otherwise, all temperature values indicated in the present application, such as, for example, the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, Tg=glass state, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and $\Delta n$ is determined at 589 nm and $\Delta\epsilon$ at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

The display used for measurement of the capacitive threshold voltage consists of two plane-parallel glass outer plates at a separation of 20 μm, each of which has on the inside an electrode layer and an unrubbed polyimide alignment layer on top, which effect a homeotropic edge alignment of the liquid-crystal molecules.

The display or test cell used for measurement of the tilt angles consists of two plane-parallel glass outer plates at a separation of 4 μm, each of which has on the inside an electrode layer and a polyimide alignment layer on top, where the two polyimide layers are rubbed antiparallel to one another and effect a homeotropic edge alignment of the liquid-crystal molecules.

The polymerisable compounds are polymerised in the display or test cell by irradiation with UVA light (usually 365 nm) of defined intensity for a prespecified time, with a voltage simultaneously being applied to the display (usually 10 V to 30 V alternating current, 1 kHz). In the examples, unless indicated otherwise, a 50 mW/cm² mercury vapour lamp is used, and the intensity is measured using a standard UV meter (model Ushio UNI meter) fitted with a 365 nm band-pass filter.

The tilt angle is determined by a crystal rotation experiment (Autronic-Melchers TBA-105). A low value (i.e. a large deviation from the 90° angle) corresponds to a large tilt here.

The VHR value is measured as follows: 0.3% of a polymerisable monomeric compound is added to the LC host mixture, and the resultant mixture is introduced into TN-VHR test cells (rubbed at 90°, TN-polyimide alignment layer, layer thickness d≈6 μm). The HR value is determined after 5 min at 100° C. before and after UV exposure for 2 h (sun test) at 1 V, 60 Hz, 64 μs pulse (measuring instrument: Autronic-Melchers VHRM-105).

In order to investigate the low-temperature stability, also referred to as "LTS", i.e. the stability of the LC mixture to individual components spontaneously crystallising out at low temperatures, bottles containing 1 g of LC/RM mixture are placed in storage at −10° C., and it is regularly checked whether the mixtures have crystallised out.

The so-called "HTP" ("helical twisting power") denotes the helical twisting power of an optically active or chiral substance in an LC medium (in μm). Unless indicated otherwise, the HTP is measured in the commercially available nematic LC host mixture MLD-6260 (Merck KGaA) at a temperature of 20° C.

EXAMPLES

Example 1

6-(4-{[4-(6-Acryloyloxyhexyl)phenoxy]difluoromethyl}-3,5-difluorophenyl)hexyl acrylate 1.1 5-Bromo-2-[(4-bromophenoxy)difluoromethyl]-1,3-difluorobenzene

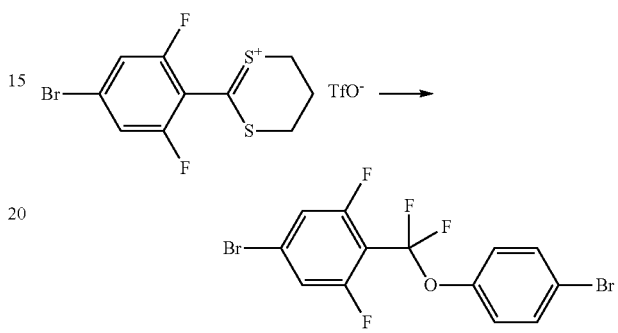

92.0 g (0.200 mol) of 2-(4-bromo-2,6-difluorophenyl)-5,6-dihydro-4H-1,3-dithiyn-1-ylium triflate are initially introduced in 600 ml of dichloromethane, and a solution of 52.0 g (0.300 mol) of 4-bromophenol in 200 ml of dichloromethane and 45 ml of triethylamine is added at −70° C. When the addition is complete, the mixture is stirred at −70° C. for a further 1 h, 160 ml (1.00 mol) of triethylamine trishydrofluoride are added, and a solution of 51.0 ml (0.996 mol) of bromine in 200 ml of dichloromethane is subsequently added dropwise. After 1 h, the cooling is removed, and the batch is warmed to −10° C. and added to a solution of 310 ml of 32 pc sodium hydroxide solution in 2 l of ice-water. The org. phase is separated off and washed with water. The aqueous phase is extracted with dichloromethane, and the combined org. phases are dried over sodium sulfate. The solvent is removed in vacuo, and the residue is filtered through silica gel with heptane, giving 5-bromo-2-[(4-bromophenoxy)difluoromethyl]-1,3-difluorobenzene as a yellow oil.

$^{19}$F-NMR (CDCl$_3$, 235 MHz)

δ=−63.1 ppm (t, J=26.7 Hz, 2 F, —CF$_2$O—), −112 (dt, J=9.7 Hz, J=26.7 Hz, 2 F, Ar—F).

1.2 6-(4-{Difluoro-[4-(6-hydroxyhex-1-ynyl)phenoxy]methyl}-3,5-difluorophenyl)hex-5-yn-1-ol

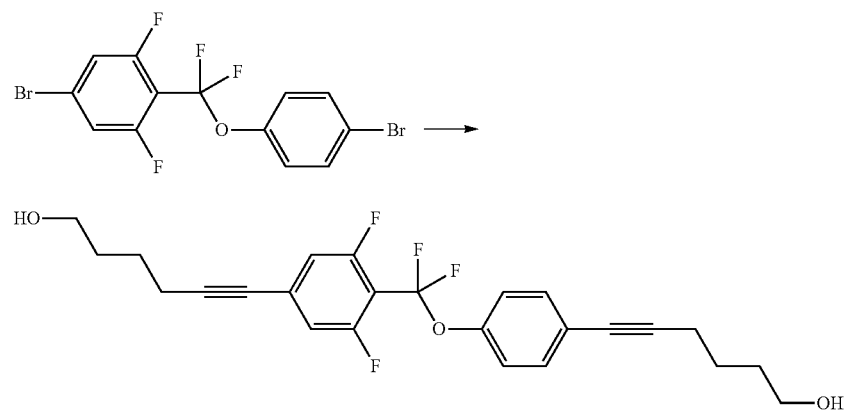

10.7 g (25.8 mmol) of 5-bromo-2-[(4-bromophenoxy)difluoromethyl]-1,3-difluorobenzene and 8.00 g (81.5 mmol) of hex-5-yn-1-ol are initially introduced in 11.3 ml of triethylamine and 500 ml of toluene, 1.50 g (2 mmol) of bis(triphenylphosphine)palladium(II) chloride and 0.700 g (3.68 mmol) of copper(I) iodide are added, and the mixture is heated under reflux overnight. The batch is subsequently added to water, neutralised using 2 N hydrochloric acid and extracted three times with toluene. The combined org. phases are dried over sodium sulfate, the solvent is removed in vacuo, and the residue is chromatographed in silica gel, firstly with toluene and then with toluene/ethyl acetate (4:1), giving 6-(4-{difluoro-[4-(6-hydroxyhex-1-ynyl)phenoxy]methyl}-3,5-difluorophenyl)hex-5-yn-1-ol as a colourless solid.

1.3 6-(4-{Difluoro-[4-(6-hydroxyhexyl)phenoxy]methyl}-3,5-difluorophenyl)hexan-1-ol

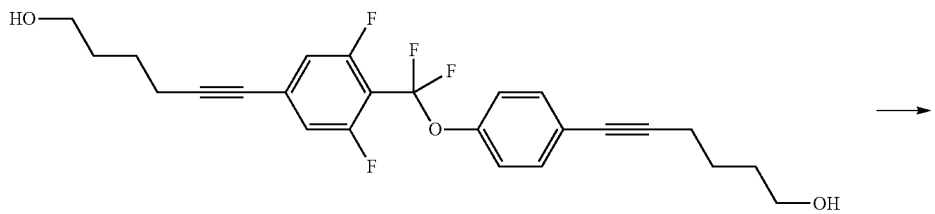

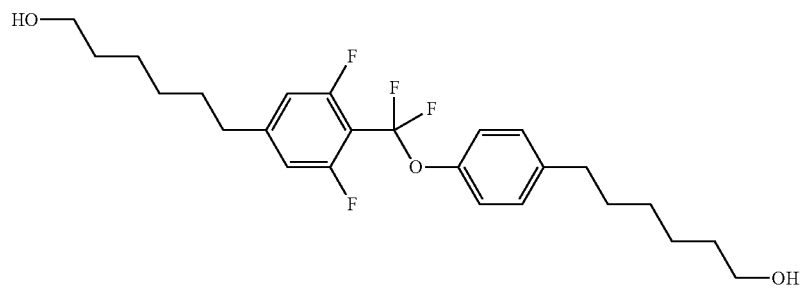

6-(4-{Difluoro-[4-(6-hydroxyhex-1-ynyl)phenoxy]methyl}-3,5-difluorophenyl)hex-5-yn-1-ol is hydrogenated to completion on palladium/active carbon catalystin THF. The catalyst is filtered off, the solvent is removed in vacuo, and the crude product is chromatographed on silica gel with toluene/ethyl acetate (1:2), giving 6-(4-{difluoro-[4-(6-hydroxyhexyl)phenoxy]methyl}-3,5-difluorophenyl)hexan-1-ol as a colourless solid.

$^{19}$F-NMR (CDCl$_3$, 235 MHz):
δ=−60.8 ppm (t, J=26.3 Hz, 2 F, —CF$_2$O—), −112 (dt, J=10.0 Hz, J=26.3 Hz, 2 F, Ar—F).

1.4 6-(4-{[4-(6-Acryloyloxyhexyl)phenoxy]difluoromethyl}-3,5-difluorophenyl)hexyl acrylate

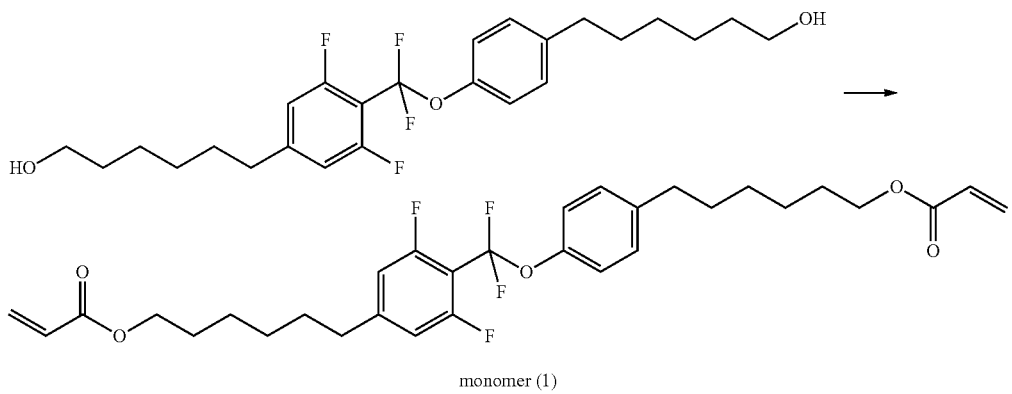

monomer (1)

17.0 g (37.2 mmol) of 6-(4-{difluoro-[4-(6-hydroxyhexyl)phenoxy]methyl}-3,5-difluorophenyl)hexan-1-ol, 8.05 g (112 mmol) of acrylic acid and 0.5 g of DMAP are initially introduced in 300 ml of dichloromethane, and a solution of 17.3 g (112 mmol) of EDC in 75 ml of dichloromethane is added dropwise with ice-cooling. After 1 h, the cooling is removed, and the batch is left to stir overnight at room temp. The solvent is substantially removed in vacuo, and the residue is chromatographed on silica gel with dichloromethane, giving 6-(4-{[4-(6-acryloyloxyhexyl)phenoxy]difluoromethyl}-3,5-difluorophenyl)hexyl acrylate as a colourless oil.

Phase behaviour Tg -71 C 13 I $^1$H-NMR(CDCl$_3$, 250 MHz):

δ=1.25-1.48 ppm (m, 8 H, CH$_2$), 1.50-1.74 ppm (m, 8 H, CH$_2$), 2.60 (m, 4 H, 2-Ar—CH$_2$—), 4.13 (t, J=6.7 Hz, 2 H, —CH$_2$O—), 4.15 (t, J=6.7 Hz, 2 H, —CH$_2$O—), 5.81 (dt, J=10.4 Hz, J=1.8 Hz, 2 H, 2 CHH=CH—COO—), 6.11 (m$_c$, 2 H, 2 CH$_2$=CH—COO—), 6.39 (2 CHH=CH—COO—), 6.78 (d, J=10.0 Hz, 2 H, Ar—H), 7.15 (m$_c$, 4 H, Ar—H).

$^{19}$F-NMR(CDCl$_3$, 235 MHz)

δ=-60.9 ppm (t, J=26.4 Hz, 2 F, —CF$_2$O—), —112.0 (dt, J=26.4, J=10.0 Hz, 2 F, Ar—F).

Example 2

6-[4'-(Difluoro-{4-[6-(2-methylacryloyloxy)hexyl]phenoxy}-methyl)-2,3',5'-trifluorobiphenyl-4-yl]hexyl 2-methylacrylate 2.1 2-(4'-Bromo-3,5,2'-trifluorobiphenyl-4-yl)-5,6-dihydro-4H-1,3-dithiyn-1-ylium triflate

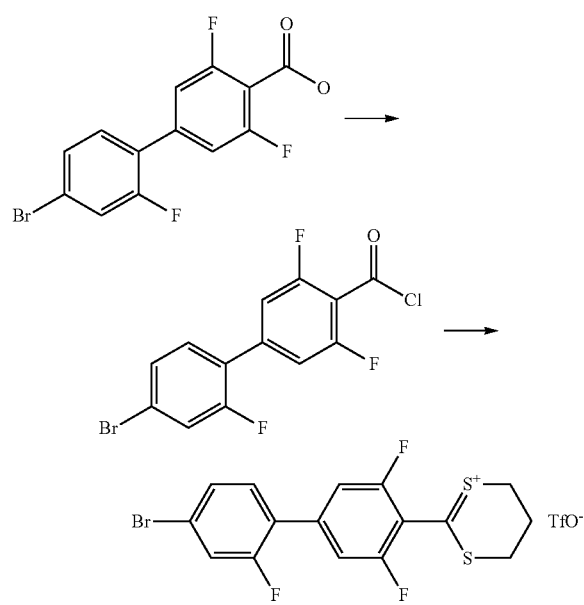

10.4 g (30.1 mmol) of 4'-bromo-3,5,2'-trifluorobiphenyl-4-carboxylic acid (CAS No. 1196677-06-1) are heated at 90° C. for 2 h with 4.4 ml (61 mmol) of thionyl chloride. After cooling, excess thionyl chloride is removed in vacuo, 3.2 ml (30 mmol) of 1,3-propanedithiol in a little dichloromethane are added with ice-cooling, and, after 1 h, 8.1 ml (92.3 mmol) of trifluoromethanesulfonic acid are added dropwise. When the addition is complete, 20 ml of acetic anhydride are carefully added, and 200 ml of ether are added. After 30 min, the batch is cooled to -60° C., the precipitated product is filtered off with suction, washed with ether and dried in vacuo, giving 2-(4'-bromo-3,5,2'-trifluorobiphenyl-4-yl)-5,6-dihydro-4H-1,3-dithiyn-1-ylium triflate as a yellow solid, which is employed in the next step without further purification.

2.2 4'-Bromo-4-[difluoro-(4-iodophenoxy)methyl]-3,5,2'-trifluorobiphenyl

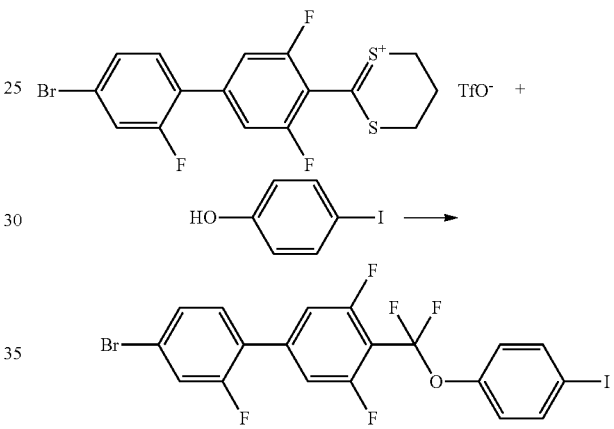

25.8 g (46.6 mmol) of 2-(4'-bromo-3,5,2'-trifluorobiphenyl-4-yl)-5,6-dihydro-4H-1,3-dithiyn-1-ylium triflate are initially introduced in 200 ml of dichloromethane, and a solution of 15.0 g (68.2 mmol) of 4-iodophenol in 50 ml of dichloromethane and 12 ml of triethylamine is added at -70° C. When the addition is complete, the mixture is stirred at -70° C. for a further 1 h, 38.0 ml (0.236 mol) of triethylamine trishydrofluoride are added, and a solution of 12.0 ml (0.234 mol) of bromine in 100 ml of dichloromethane is subsequently added dropwise. After 1 h, the cooling is removed, and the batch is warmed to -10° C. and added to a solution of 75 ml of 32 pc sodium hydroxide solution in 500 ml of ice-water. The org. phase is separated off and washed with water. The aqueous phase is extracted with dichloromethane, and the combined org. phases are dried over sodium sulfate. The solvent is removed in vacuo, the residue is filtered through silica gel with heptane and recrystallised from ethanol, giving 4'-bromo-4-[difluoro-(4-iodophenoxy)methyl]-3,5,2'-trifluorobiphenyl as a yellow oil.

$^{19}$F-NMR (CDCl$_3$, 235 MHz)

δ=-59.2 ppm (t, J=26.4 Hz, 2 F, -CF$_2$O—), -108 (dt, J=9.8 Hz, J=26.4 Hz, 2 F, Ar—F), -113 (dt, J=9.1 Hz, J=10.2 Hz, 1 F, Ar—F).

2.3 6-(4'-{Difluoro-[4-(6-hydroxyhex-1-ynyl)phenoxy]methyl}-2,3',5'-trifluorobiphenyl-4-yl)hex-5-yn-1-ol

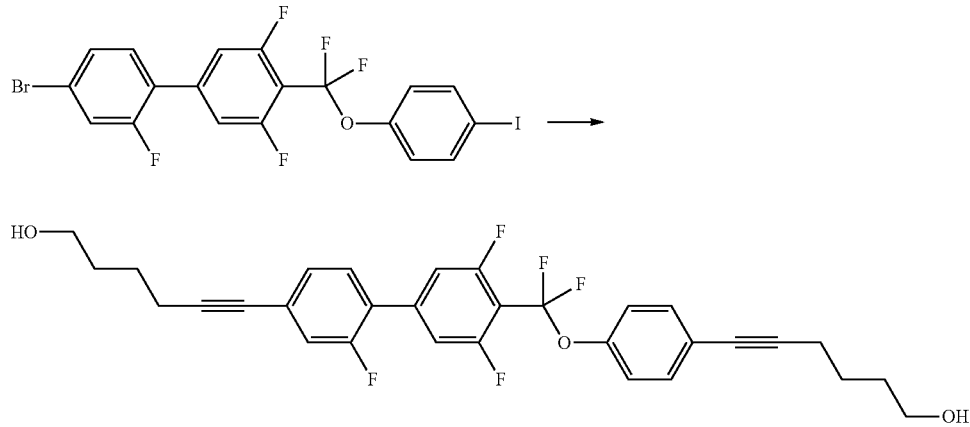

6.00 g (10.8 mmol) of 4'-bromo-4-[difluoro-(4-iodophenoxy)methyl]-3,5,2'-trifluorobiphenyl and 4.00 g (40.8 mmol) of hex-5-yn-1-ol are initially introduced in 6 ml of triethylamine and 300 ml of toluene, 0.700 g (1.00 mmol) of bis(triphenylphosphine)palladium(II) chloride and 0.100 g (0.525 mmol) of copper(I) iodide are added, and the mixture is heated under reflux overnight. The batch is subsequently added to water, neutralised using 2 N hydrochloric acid and extracted three times with toluene. The combined org. phases are dried over sodium sulfate, the solvent is removed in vacuo, and the residue is chromatographed on silica gel firstly with toluene and then with toluene/ethyl acetate (4:1), giving 6-(4-{difluoro-[4-(6-hydroxyhex-1-ynyl)phenoxy]methyl}-3,5-difluorophenyl)hex-5-yn-1-ol as a colourless solid.

2.4 6-(4'-{Difluoro-[4-(6-hydroxyhexyl)phenoxy]methyl}-2,3',5'-trifluorobiphenyl-4-yl)hexan-1-ol

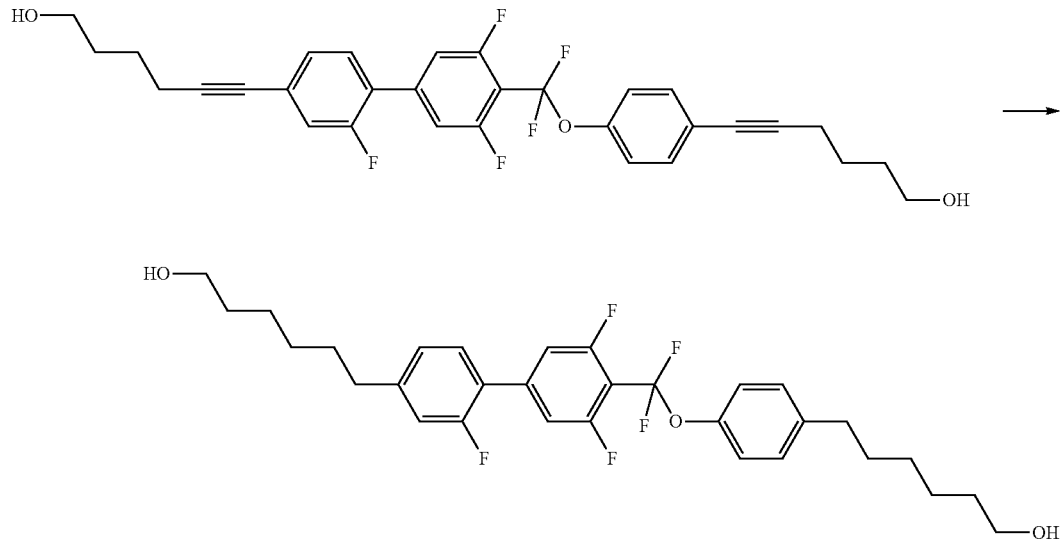

6-(4-{Difluoro-[4-(6-hydroxyhex-1-ynyl)phenoxy]methyl}-3,5-difluorophenyl)hex-5-yn-1-ol is hydrogenated to completion on palladium/active carbon catalyst in THF. The catalyst is filtered off, the solvent is removed in vacuo, and the crude product is employed in the next step without further purification.

2.5 6-[4'-(Difluoro-{4-[6-(2-methylacryloyloxy)hexyl]phenoxy}methyl)2,3',5'-trifluorobiphenyl-4-yl]hexyl 2-methylacrylate

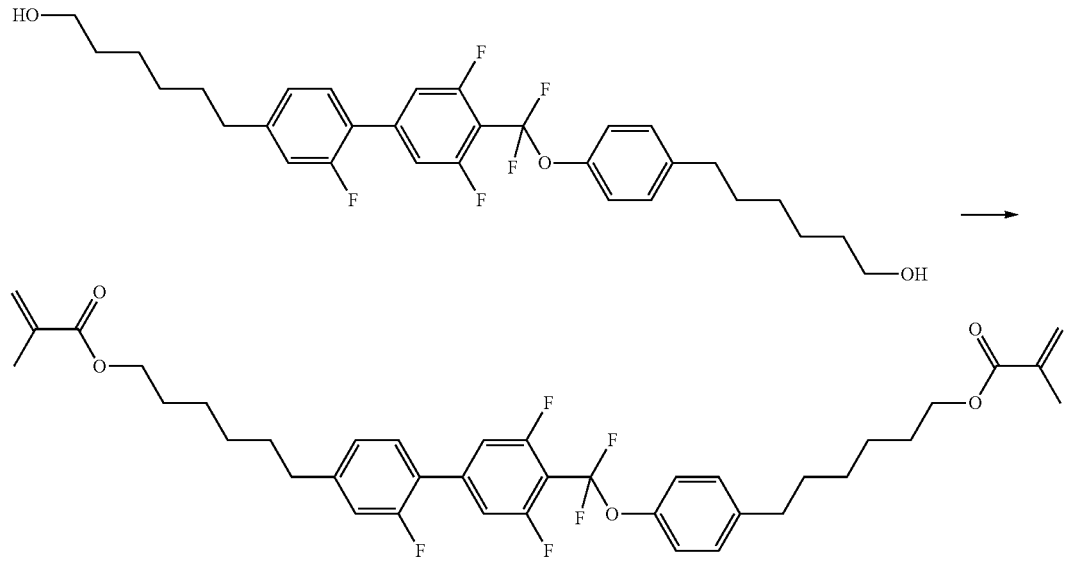

1.00 g (1.82 mmol) of 6-(4'-{difluoro-[4-(6-hydroxyhexyl)phenoxy]methyl}-2,3',5'-trifluorobiphenyl-4-yl)hexan-1-ol is initially introduced in 15 ml of dichloromethane with ice-cooling, 1 ml (7.21 mmol) of triethylamine is added, and a solution of 0.700 g (6.73 mmol) of methacryloyl chloride in 5 ml of dichloromethane is added dropwise. The batch is left to stir overnight, the solvent is removed in vacuo, and the residue is purified by chromatography on silica gel with toluene/dichloromethane (1:1), giving 6-[4'-(difluoro-{4-[6-(2-methylacryloyloxy)hexyl]phenoxy}methyl)-2,3',5'-trifluorobiphenyl-4-yl]hexyl 2-methylacrylate as a colourless oil. Phase behaviour Tg −59 N −28.5 I.

$^1$H-NMR (CDCl$_3$, 250 MHz):

δ=1.24-1.48 ppm (m, 8 H, CH$_2$), 1.55-1.79 ppm (m, 8 H, CH$_2$), 1.94 (m$_c$, 6 H, 2 CH$_3$) 2.63 (m, 4 H, 2-Ar—CH$_2$—), 4.13 (t, J=6.6 Hz, 2 H, —CH$_2$O—), 4.15 (t, J=6.6 Hz, 2 H, —CH$_2$O—), 5.54 (m$_c$, 2 H, 2 CHH=CH—COO—), 6.09 (m$_c$, 2 CH$_2$=CH—COO—), 6.95-7.09 (m, 2 H, Ar—H), 7.09-7.24 (m, 6 H, Ar—H), 7.32 (t, J=7.9 Hz, 1 H, Ar—H).

$^{19}$F-NMR(CDCl$_3$, 235 MHz)

δ=−60.9 ppm (t, J=26.5 Hz, 2 F, —CF$_2$O—), −111 (dt, J=10.0, J=26.4 Hz, 2 F, Ar—F), −118 (dd, J=8.2 Hz, J=12.0 Hz, 1 F, Ar—F).

Example 3

4-[4'-(Difluoro-{4-[4-(2-methylacryloyloxy)butyl]phenoxy}-methyl)-2,3',5'-trifluorobiphenyl-4-yl] butyl 2-methylacrylate

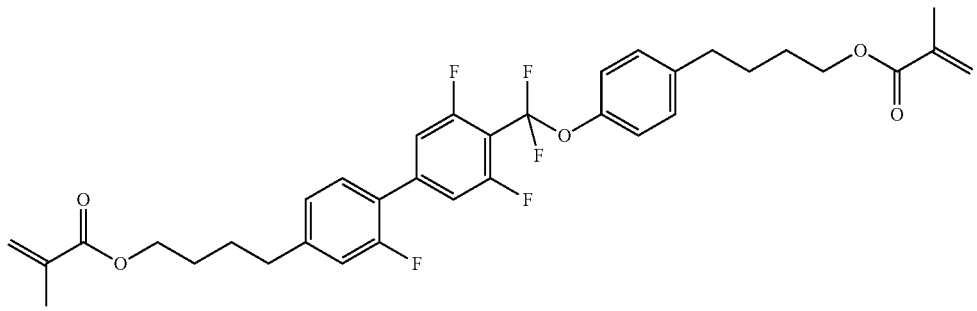 [SMILES: C=C(C)C(=O)OCCCCc1ccc(OC(F)(F)c2c(F)cc(-c3ccc(CCCCOC(=O)C(=C)C)cc3F)cc2F)cc1]

Analogously to Example 2, 4-[4'-(difluoro-{4-[4-(2-methylacryloyloxy)-butyl]phenoxy}methyl)-2,3',5'-trifluorobiphenyl-4-yl]butyl 2-methylacrylate is obtained as colourless crystals of m.p. 128° C.

Example 4

6-(4-{[4-(6-Acryloyloxybutyl)phenoxy]difluoromethyl}-3,5-difluorophenyl)butyl acrylate

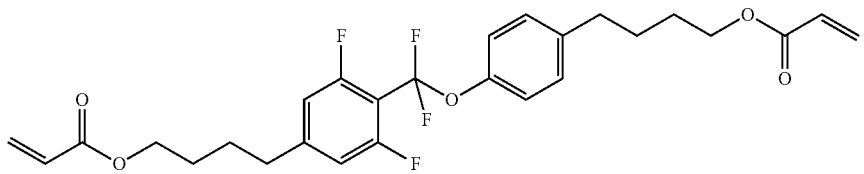 [SMILES: C=CC(=O)OCCCCc1ccc(OC(F)(F)c2c(F)cc(CCCCOC(=O)C=C)cc2F)cc1]

The compound is prepared analogously to Example 1.
M.p. 128° C.

Example 5

6-{4'-[(3,4,5-Trifluorophenoxy)difluoromethyl]-3',5'-difluorobiphenyl-4-yl}hexyl methylacrylate

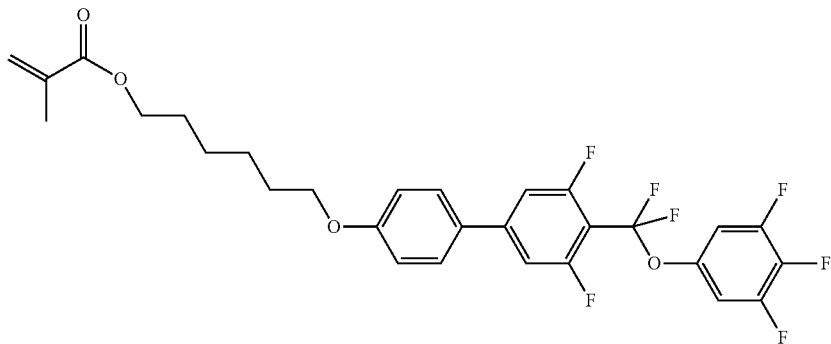 [SMILES: C=C(C)C(=O)OCCCCCCOc1ccc(-c2cc(F)c(C(F)(F)Oc3cc(F)c(F)c(F)c3)c(F)c2)cc1]

The compound is prepared analogously to Example 2.
M.p. 58° C.

Example 6

6-(4-{[4-(6-Acryloyloxyhexyl)-3,5-difluorophenoxy]difluoromethyl}-3,5-difluorophenyl)hexyl acrylate

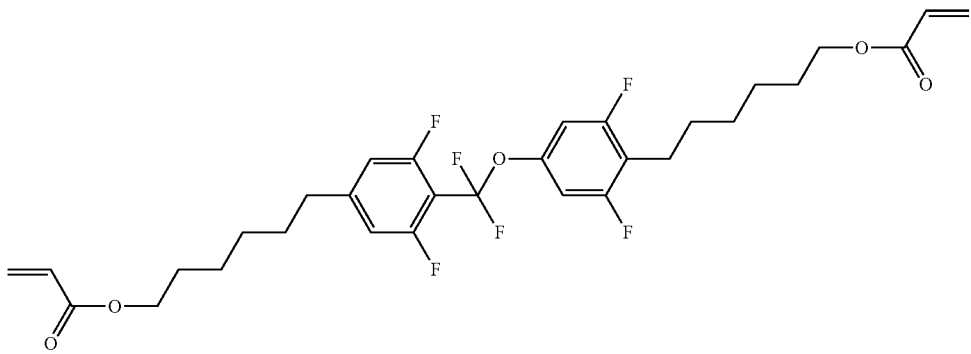 [SMILES: C=CC(=O)OCCCCCCc1cc(F)c(C(F)(F)Oc2cc(F)c(CCCCCCOC(=O)C=C)c(F)c2)c(F)c1]

The compound is prepared analogously to Example 1.

Use Example 1

The following monomers are used:

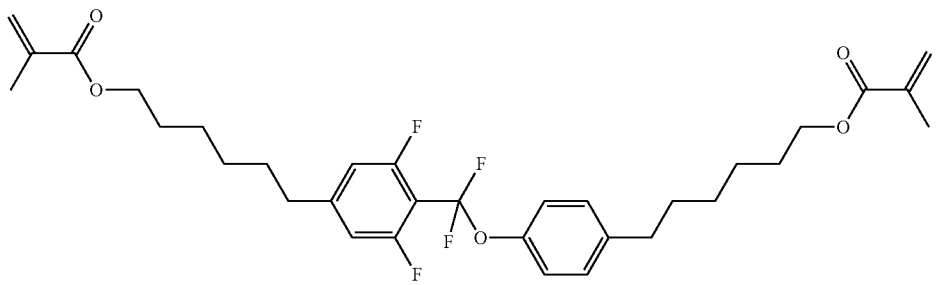 [SMILES: C=C(C)C(=O)OCCCCCCc1ccc(OC(F)(F)c2c(F)cc(CCCCCCOC(=O)C(=C)C)cc2F)cc1]

Monomer (1) from Example 1

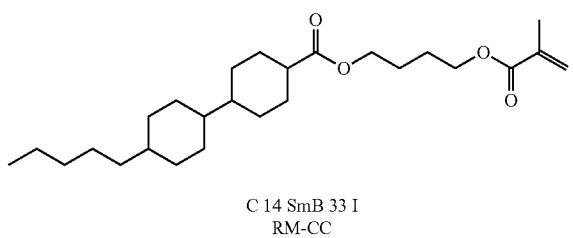 [SMILES: C=C(C)C(=O)OCCCCOC(=O)C1CCC(C2CCC(CCCCC)CC2)CC1]

C 14 SmB 33 I
RM-CC

The following additives are used:

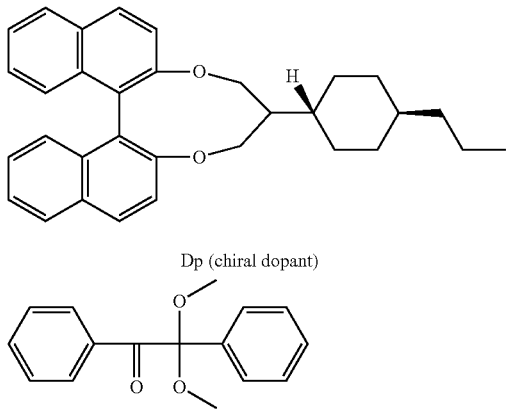

Dp (chiral dopant)

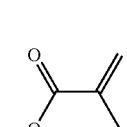

In (Ciba Irgacure ® 651, photoinitiator)

The following base mixture (host) H1 is used:

| Composition | |
|---|---|
| Component Acronym | Proportion % by wt. |
| AUUQU-2-F | 10 |
| AUUQU-3-F | 11 |
| AUUQU-4-F | 7 |
| AUUQU-5-F | 6 |
| AUUQU-7-F | 7 |
| AUUQU-3-T | 10 |
| AUUQU-3-OT | 11 |

-continued

| | |
|---|---|
| PUZU-2-F | 7 |
| PUZU-3-F | 11 |
| PUZU-5-F | 11 |
| AGUQU-3-F | 4 |
| AUUQU-3-N | 5 |
| Σ | 100.00 |

| Properties |
|---|
| T (N, I): 71° C. |
| Δn (20° C., 589 nm): 0.152 |

The polymerisable LC mixture M1 according to the invention, comprising monomer (1) according to the invention from Example 1, is prepared from base mixture H1 by admixing the monomers and additives mentioned above. The compositions of the mixtures are shown in Table 1.

TABLE 1

| | M1 |
|---|---|
| Component | Proportion [% by wt.] |
| H1 | 85 |
| Dp | 3.8 |
| In | 0.2 |
| (1) | 4.5 |
| RM-CC | 6.5 |

The mixtures are characterised as described below before the polymerisation. The reactive components are then polymerised in the blue phase by irradiation once (180 s), and the resultant media are re-characterised.

Description of the Polymerisation

Before the polymerisation of a sample, the phase properties of the medium are established in a test cell having a thickness of about 10 microns and an area of 2×2.5 cm. The filling is carried out by capillary action at a temperature of 75° C. The measurement is carried out under a polarising microscope with heating stage with a temperature change of 1° C./min.

The polymerisation of the media is carried out by irradiation with a UV lamp (Dymax, Bluewave 200, 365 nm interference filter) having an effective power of about 3.0 mW/cm² for 180 seconds. The polymerisation is carried out directly in the electro-optical test cell.

The polymerisation is carried out initially at a temperature at which the medium is in the blue phase I (BP-I). The polymerisation is carried out in a plurality of part-steps, which gradually result in complete polymerisation. The temperature range of the blue phase generally changes during the polymerisation. The temperature is therefore adapted between each part-step so that the medium is still in the blue phase. In practice, this can be carried out by observing the sample under the polarising microscope after each irradiation operation of about 5 s or longer. If the sample becomes darker, this indicates a transition into the isotropic phase. The temperature for the next part-step is reduced correspondingly.

The entire irradiation time which results in maximum stabilisation is typically 180 s at the irradiation power indicated. Further polymerisations can be carried out in accordance with an optimised irradiation/temperature programme.

Alternatively, the polymerisation can also be carried out in a single irradiation step, in particular if a broad blue phase is already present before the polymerisation.

Electro-optical Characterisation

After the above-described polymerisation and stabilisation of the blue phase, the phase width of the blue phase is determined. The electro-optical characterisation is carried out subsequently at various temperatures within and if desired also outside this range.

The test cells used are fitted on one side with interdigital electrodes on the cell surface. The cell gap, the electrode separation and the electrode width are typically each 10 microns. This uniform dimension is referred to below as the gap width. The area covered by electrodes is about 0.4 cm$^2$. The test cells do not have an alignment layer.

For the electro-optical characterisation, the cell is located between crossed polarising filters, where the longitudinal direction of the electrodes adopts an angle of 45° to the axes of the polarising filter. The measurement is carried out using a DMS301 (Autronic-Melchers) at a right angle to the cell plane, or by means of a highly sensitive camera on the polarising microscope. In the voltage-free state, the arrangement described gives an essentially dark image (definition 0% transmission).

Firstly, the characteristic operating voltages and then the response times are measured on the test cell. The operating voltage is applied to the cell electrodes in the form of rectangular voltage having an alternating sign (frequency 100 Hz) and variable amplitude, as described below.

The transmission is measured while the operating voltage is increased. The achievement of the maximum value of the transmission defines the characteristic quantity of the operating voltage $V_{100}$. Equally, the characteristic voltage $V_{10}$ is determined at 10% of the maximum transmission. These values are measured at various temperatures in the range of the blue phase.

Relatively high characteristic operating voltages $V_{100}$ are observed at the upper and lower end of the temperature range of the blue phase. In the region of the minimum operating voltage, $V_{100}$ generally only increases slowly with temperature. This temperature range, limited by $T_1$ and $T_2$, is referred to as the usable, flat temperature range (FR). The width of this "flat range" (FR) is $(T_2-T_1)$ and is known as the width of the flat range (WFR). The precise values of $T_1$ and $T_2$ are determined by the intersections of tangents on the flat curve section FR and the adjacent steep curve sections in the $V_{100}$/temperature diagram.

In the second part of the measurement, the response times during switching on and off ($\tau_{on}$, $\tau_{off}$) are determined. The response time $\tau_{on}$ is defined by the time to achievement of 90% intensity after application of a voltage at the level of $V_{100}$ at the selected temperature. The response time $\tau_{off}$ is defined by the time until the decrease by 90% starting from maximum intensity at $V_{100}$ after reduction of the voltage to 0 V. The response time is also determined at various temperatures in the range of the blue phase.

As further characterisation, the transmission at continuously increasing and falling operating voltage between 0 V and $V_{100}$ is measured at a temperature within the FR. The difference between the two curves is known as hysteresis. The difference in the transmissions at $0.5 \cdot V_{100}$ and the difference in the voltages at 50% transmission are, for example, characteristic hysteresis values and are known as $\Delta T_{50}$ and $\Delta V_{50}$ respectively.

As a further parameter, the ratio of the transmission in the voltage-free state before and after passing through a switching cycle can be measured. This transmission ratio is known as the "memory effect". In the ideal state, the value of the memory effect is 1.0. Values above 1 mean that a certain memory effect is present in the form of excessive residual transmission after the cell has been switched on and off. This value is likewise determined in the working range of the blue phase (FR).

The results are summarised in Table 2.

TABLE 2

| Measurement values (20° C.) | M1 |
|---|---|
| Transition point before the polymerisation | 34.4° C. |
| Polymerisation temperature | 34.9° C. |
| $V_{100}$ (20° C.) | 48 V |
| $\Delta V_{50}$ (20° C.) | 1.9 |
| Contrast, switching on | 206 |
| Contrast, switching off | 208 |
| Memory effect | 0.99 |

The polymerisable mixture is polymerised in a single irradiation step at a temperature of about 30-50° C. at the lower end of the temperature range of the blue phase (details cf. above).

The polymer-stabilised liquid-crystalline media exhibit a blue phase over a broad temperature range.

The polymer-stabilised medium M1, prepared using monomer (1) according to the invention, exhibits a reduction in hysteresis ($\Delta V_{50}$) and good contrast on switching on and on switching off compared with conventional media from the prior art. In particular, the contrast on switching on and the contrast on switching off in medium M1 according to the invention are close to one another, which means very good stabilisation of the blue phase.

It is evident from this that the monomers according to the invention are particularly suitable for the stabilisation of blue phases, in particular in the case of media having a high concentration of chiral dopant.

The invention claimed is:

1. A compounds of formula I

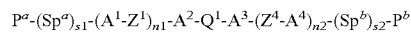

in which the individual radicals have the following meanings:

$P^a$ denotes a polymerisable group, $P^b$ denotes a polymerisable group, H or F, $Sp^a$, $Sp^b$ each, independently of one another, denote a spacer group, s1, s2 each, independently of one another, denote 0 or 1, n1 denotes 0 or 1, n2 denotes 0, $Q^1$ denotes —CF$_2$O—, $Z^1$, $Z^4$ each, independendently of one another, denote a single bond, —CF$_2$O—, —OCF$_2$—, —CH$_2$O—, —OCH$_2$—, —(CO)O—, —O(CO)—, —(CH$_2$)$_4$—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —(CH$_2$)$_3$O—, —O(CH$_2$)$_3$—, —CH=CF—, —C≡C—, —O—, —CH$_2$—, —(CH$_2$)$_3$—, or —CF$_2$—, where Z$^1$ and Q$^1$ or Z$^4$ and Q$^1$ do not simultaneously denote —CF$_2$O—, A$^2$ denotes

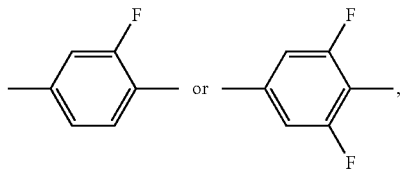

A$^3$ denotes

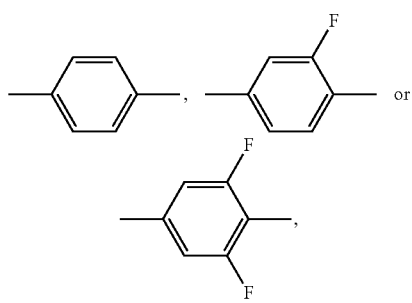

and
A$^1$, A$^4$
each, independently of one another, denotes a radical selected from the following groups:
a) the group consisting of 1,4-phenylene and 1,3-phenylene, in which, in addition, one or two CH groups may each be replaced by N and in which, in addition, one or more H atoms may each be replaced by L,
b) the group consisting of trans-1,4-cyclohexylene, 1,4-cyclohexenylene and 1,4'-bicyclohexylene, in which, in addition, one or more non-adjacent CH$_2$ groups may each be replaced by —O— or —S— and in which, in addition, one or more H atoms may each be replaced by F or Cl,
c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may, in addition, be mono- or polysubstituted by L, and
d) the group consisting of saturated, partially unsaturated or fully unsaturated, and optionally substituted, polycyclic radicals having 5 to 20 cyclic C atoms, one or more of which may also be replaced by heteroatoms,
where, in addition, one or more H atoms in these radicals may each be replaced by L, and/or one or more double bonds may each be replaced by single bonds, and/or one or more CH groups may each be replaced by N, L on each occurrence, identically or differently, denotes F, Cl, CN, SCN, SF$_5$ or straight-chain or branched, in each case optionally fluorinated alkyl, alkoxy, alkylcarbonyl, alkoxycarbonyl, alkylcarbonyloxy or alkoxycarbonyloxy having up to 12 C atoms.

2. A compound according to claim 1, wherein said compound is of formula I*

$$P^a\text{-}(Sp^a)_{s1}\text{-}(A^1)_{n1}\text{-}A^2\text{-}Q^1\text{-}A^3\text{-}(Sp^b)_{s2}\text{-}P^b \qquad I^*$$

in which P$^a$, P$^b$, Sp$^a$, Sp$^b$, A$^1$, A$^2$, A$^3$, Q$^1$, s1, s2 and n1 are as defined in claim 1.

3. A compound according to claim 1, wherein said compound is of the formula

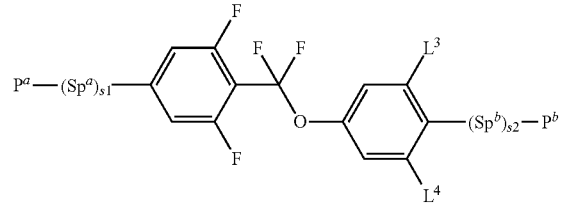

in which P$^a$, P$^b$, Sp$^a$, Sp$^b$, s1, s2 are as defined in claim 1, and L$^3$ and L$^4$, independently of one another, denote H or F.

4. A liquid crystal medium comprising one or more compounds of formula I $$P^a\text{-}(Sp^a)_{s1}\text{-}(A^1\text{-}Z^1)_{n1}\text{-}A^2\text{-}Q^1\text{-}A^3\text{-}(Z^4\text{-}A^4)_{n2}\text{-}(Sp^b)_{s2}\text{-}P^b \qquad I$$

in which the individual radicals have the following meanings:
P$^a$, P$^b$ each, independently of one another, denote a polymerizable group,
Sp$^a$, Sp$^b$ each, independently of one another, denote a spacer group,
s1, s2 each, independently of one another, denote 0 or 1,
n1 denotes 0 or 1,
n2 denotes 0,
Q$^1$ denotes —CF$_2$O—,
Z$^1$, Z$^4$ each independently of one another, denote a single bond, —CF$_2$O—, —OCF$_2$—, —CH$_2$O—, —OCH$_2$—, —(CO)O—, —O(CO)—, —(CH$_2$)$_4$—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —(CH$_2$)$_3$O—, —O(CH$_2$)$_3$—, —CH=CF—, —C≡C—, —O—, —CH$_2$—, —(CH$_2$)$_3$—, or —CF$_2$—, where Z$^1$ and Q$^1$ or Z$^4$ and Q$^1$ do not simultaneously denote —CF$_2$O—, A$^2$ denotes

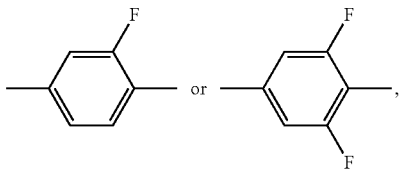

A$^3$ denotes

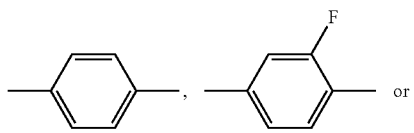

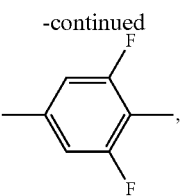

and $A^1, A^4$
each, independently of one another, denotes a radical selected from the following groups:
a) the group consisting of 1,4-phenylene and 1,3-phenylene, in which, in addition, one or two CH groups may each be replaced by N and in which, in addition, one or more H atoms may each be replaced by L,
b) the group consisting of trans-1,4-cyclohexylene, 1,4-cyclohexylene and 1,4'-bicyclohexenylene, in which, in addition, one or more non-adjacent $CH_2$ groups may each be replaced by —O— or —S— and in which, in addition, one or more H atoms may each be replaced by F or Cl,
c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may, in addition, be mono- or polysubstituted by L, and
d) the group consisting of saturated, partially unsaturated or fully unsaturated, and optionally substituted, polycyclic radicals having 5 to 20 cyclic C atoms, one or more of which may also be replaced by heteroatoms,
where, in addition, one or more H atoms in these radicals may each be replaced by L, and/or one or more double bonds may each be replaced by single bonds, and/or one or more CH groups may be replaced by N,
L on each occurrence, identically or differently, denotes F, Cl, CN, SCN, $SF_5$ or straight-chain or branched, in each case optionally fluorinated alkyl, alkoxy, alkylcarbonyl, alkoxycarbonyl, alkylcarbonyloxy or alkoxycarbonyloxy having up to 12 C atoms,
or a polymer obtainable by polymerization of one or more compounds of the formula I.

5. The liquid crystal medium according to claim 4, wherein said medium further comprises one or more other polymerizable compounds and/or one more unpolymerizable liquid-crystalline compounds.

6. The liquid crystal medium according to claim 4, wherein said medium comprises the following components:
a polymerizable component A comprising one or more compounds of formula I,
a liquid-crystalline component B comprising one or more compounds of formulla II

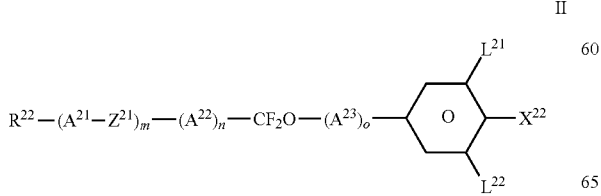

II in which the individual radicals have the following meanings:

$R^{22}$ denotes H, F, Cl or straight-chain or branched alkyl having 1 to 20 C atoms, which is unsubstituted or mono- or polysubstituted by F, Cl or CN, and in which, in addition, one or more non-adjacent $CH_2$ groups may also each be replaced, independently of one another, by —O—, —S—, —NH—, —$NR^{01}$—, —$SiR^{01}R^{02}$—, —CO—, —COO—, —OCO—, —O—CO—O—, —S—CO—, —CO—S—, —$CY^{01}$=$CY^{02}$— or —C≡C— in such a way that O and/or S atoms are not linked directly to one another, $Y^{01}, Y^{02}$ each, independently of one another, denote F, Cl or CN, one of the radicals $Y^{01}$ and $Y^{02}$ also denotes H, $R^{01}, R^{02}$ each, independently of one another, denote H or alkyl having 1 to 12 C atoms, $A^{21}, A^{22}, A^{23}$ each, independently of one another and on each occurrence identically or differently, denote

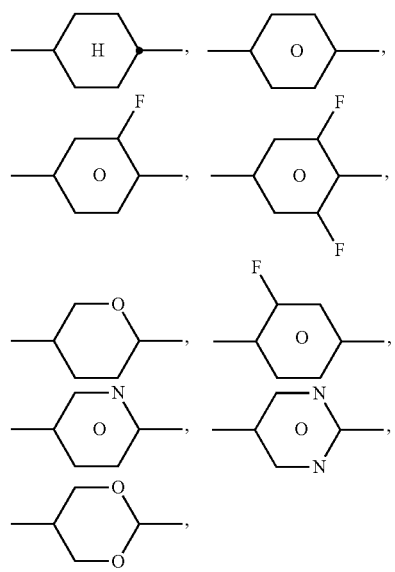

$Z^{21}$ on each occurrence, identically or differently, denotes a single bond, —$(CH_2)_4$—, —$CH_2CH_2$—, —$CF_2$—$CF_2$—, —$CF_2$—$CH_2$—, —$CH_2$—$CF_2$—, —CH=CH—, —CF=CF—, —CF=CH—, —$(CH_2)_3O$—, —$O(CH_2)_3$—, —CH=CF—, —C≡C—, —$CH_2O$—, —$OCH_2$—, —$CF_2O$—, —$OCF_2$—, —CO—O— or —O—CO—, $X^{22}$ denotes F, Cl, —CN, —NCS, —$SF_5$, —$SO_2CF_3$, or alkyl, alkenyl, alkenyloxy, alkylalkoxy or alkoxy having up to 3 C atoms, which is mono- or polysubstituted by F, Cl or CN, $L^{21}, L^{22}$ each, independently of one another, denote H or F, m denotes 0, 1 or 2, n denotes 1, 2 or 3, o denotes 0, 1 or 2, where m+n+o denotes 1, 2, 3 or 4, optionally a liquid-crystalline component C comprising one or more compounds of formula III

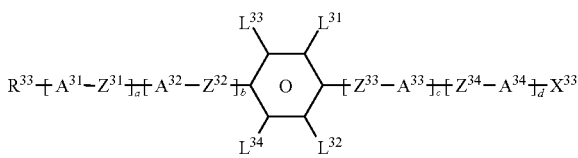

in which
a, b, c, d each, independently of one another, denote 0, 1 or 2, where
a+b+c+d is 0, 1, 2, 3 or 4,
$A^{31}$, $A^{32}$, $A^{33}$, $A^{34}$ each, independently of one another and on each occurrence identically or differently, denote

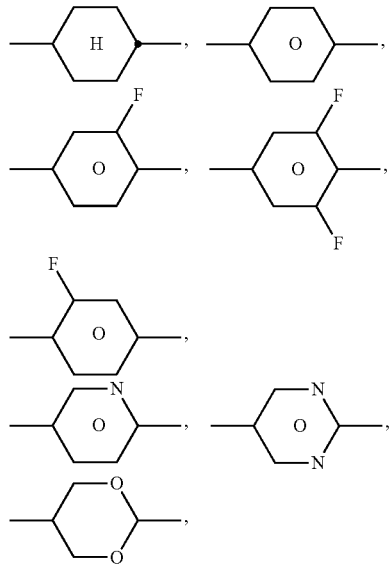

$Z^{31}$, $Z^{32}$, $Z^{33}$, $Z^{34}$ each, independently of one another and on each occurrence identically or differently, denote a single bond, —(CH$_2$)$_4$—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —(CH$_2$)$_3$O—, —O(CH$_2$)$_3$—, —CH=CF—, —C≡C—, —CH$_2$O—, —OCH$_2$—, —CF$_2$O—, —OCF$_2$—, —CO—O— or —O—CO—,
$R^{33}$ denotes alkyl or alkoxy having 1 to 15 C atoms, which is unsubstituted or mono- or polysubstituted by F, Cl or CN, and in which, in addition, one or more non-adjacent CH$_2$ groups may also each be replaced, independently of one another, by —O—, —S—, —SiR$^x$R$^y$—, —CH=CH—, —C≡C—, —CO—O— or —O—CO— in such a way that O and/or S atoms are not linked directly to one another, preferably a straight-chain alkyl, alkoxy, alkenyl, alkenyloxy or —O-alkylene-O— radical having up to 10 C atoms, which is unsubstituted or mono- or polysubstituted by F or Cl,
$L^{31}$, $L^{32}$, $L^{33}$, $L^{34}$ each, independently of one another, denote H, F, Cl, CN, or alkyl or alkoxy having 1 to 15 C atoms, which is unsubstituted or mono- or polysubstituted by F, Cl or CN, and in which, in addition, one or more non-adjacent CH$_2$ groups may also each be replaced, independently of one another, by —O—, —S—, —SiR$^x$R$^y$—, —CH=CH—, —C≡C—, —CO—O— or —O—CO— in such a way that O and/or S atoms are not linked directly to one another, with the proviso that at least one of the radicals $L^{31}$, $L^{32}$, $L^{33}$ and $L^{34}$ is other than H,
$X^{33}$ denotes F, Cl, CF$_3$, OCF$_3$, CN, NCS, —SF$_5$ or —SO$_2$—R$^z$,
$R^x$ and $R^y$ each, independently of one another, denote H, alkyl or alkoxy having 1 to 7 C atoms, and
$R^z$ denotes alkyl having 1 to 7 C atoms, which is unsubstituted or mono- or polysubstituted by F or Cl,
and a component D comprising one or more optically active and/or chiral compounds.

7. A process for the preparation of an liquid crystal medium according to claim 4, wherein one or more liquid-crystalline compounds or a liquid-crystal medium are mixed with said one or more compounds of formula I,
and optionally with further chiral and/or optically compounds and/or additives.

8. A liquid crystal display containing a liquid crystal medium according to claim 4.

9. The liquid crystal display according to claim 8, wherein said display is a display having a blue phase, a PS or PSA display, a PSA-VA, PSA-OCB, PSA-IPS, PSA-FFS or PSA-TN display.

10. The liquid crystal display according to claim 8, wherein said display comprises a liquid crystal cell having two substrates and two electrodes, where at least one substrate is transparent to light and at least one substrate has one or two electrodes, and a layer, located between said substrates, of said liquid crystal medium wherein said medium comprises a polymerized component and a low-molecular-weight component, wherein said polymerized component is obtainable by polymerisation of one or more polymerisable compounds in said liquid crystal medium between said substrates of said liquid crystal cell wherein at least one of the polymerizable compounds is a compound of said formula I.

11. A method for stabilizing the blue phase of an liquid crystal medium comprising adding one or more compounds according to claim 1 in said medium.

12. A compound according to claim 1, wherein n1 denotes 0.

13. The medium according to claim 6, wherein, in formula II, m+n+o denotes 2, 3 or 4.

14. The medium according to claim 6, wherein, in formula III, $R^{33}$ denotes a straight-chain alkyl, alkoxy, alkenyl, alkenyloxy or —O-alkylene-O— radical having up to 10 C atoms, which is unsubstituted or mono- or polysubstituted by F or Cl.

15. The medium according to claim 6, wherein, in formula III, $R^x$ and $R^y$ each, independently of one another, denote methyl, ethyl, propyl or butyl.

16. The medium according to claim 6, wherein, in formula III, $R^z$ denotes CF$_3$, C$_2$F$_5$ or n-C$_4$F$_9$.

17. The medium according to claim 6, wherein, in formula III,
$R^{33}$ denotes a straight-chain alkyl, alkoxy, alkenyl, alkenyloxy or—O-alkylene-O—radical having up to 10 C atoms, which is unsubstituted or mono- or polysubstituted by F or Cl,
$R^x$ and $R^y$ each, independently of one another, denote methyl, ethyl, propyl or butyl, and
$R^z$ denotes CF$_3$, C$_2$F$_5$ or n-C$_4$F$_9$.

18. A compound according to claim 1, wherein $P^a$ and $P^b$ are each selected from vinyloxy, acrylate, methacrylate, fluoroacrylate, chloroacrylate, oxetane and epoxide groups.

19. A compound according to claim 1, wherein $Sp^a$ and $Sp^b$ are each selected from the formula Sp"-X", wherein Sp" denotes alkylene having 1 to 20, which is unsubstituted or mono- or polysubstituted by F, Cl, Br, I or CN, and in which, in addition, one or more non-adjacent $CH_2$ groups may each be replaced, independently of one another, by —O—, —S—, —NH—, —N(R°)—, —Si($R^{00}R^{000}$)—, —CO—, —CO—O—, —O—CO—, —O—CO—O—, —S—CO—, —CO—S—, —N($R^{00}$)—CO—O—, —O—CO—N($R^{00}$)—, —N($R^{00}$)—CO—N($R^{00}$)—, —CH═CH— or —C≡C— in such a way that O and/or S atoms are not linked directly to one another, X" denotes —O—, —S—, —CO—, —CO—O—, —O—CO—, —O—CO—O—, —CO—N($R^{00}$)—, —N($R^{00}$)—CO—, —N($R^{00}$)—CO—N($R^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH═N—, —N═CH—, —N═N—, —CH═CR°—, —CY$^2$═CY$^3$—, —C≡C—, —CH═CH—CO—O—, —O—CO—CH═CH— or a single bond, $R^{00}$ and $R^{000}$ each, independently of one another, denote H or alkyl having 1 to 12 C atoms, and $Y^2$ and $Y^3$ each, independently of one another, denote H, F, Cl or CN.

20. A compound according to claim 1, wherein $Sp^a$ and $Sp^b$ are each selected from —(CH$_2$)$_{p1}$—, —(CH$_2$)$_{p1}$—O—, —(CH$_2$)$_{p1}$—O—CO—, —(CH$_2$)$_{p1}$—O—CO—O—, in which p1 is an integer from 1 to 12.

21. A compound according to claim 1, wherein s1 and s2 each denote 1.

22. A compound according to claim 1, wherein n1 denotes 1.

23. A compound according to claim 1, wherein $A^2$ and $Q^1$ together denote a group of the formula

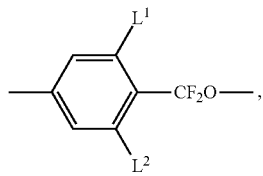

in which $L^1$ is F and $L^2$ is H or F.

24. A compound according to claim 1, wherein said compound is selected from the following formula:

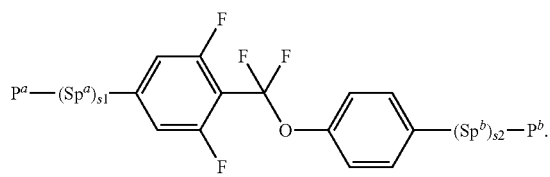

25. A compound according to claim 1, wherein said compound is selected from the following formula:

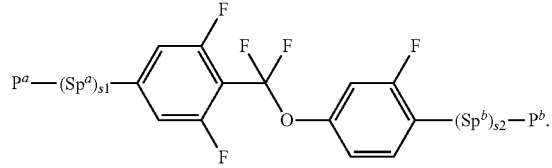

26. A compound according to claim 1, wherein said compound is selected from the following formula:

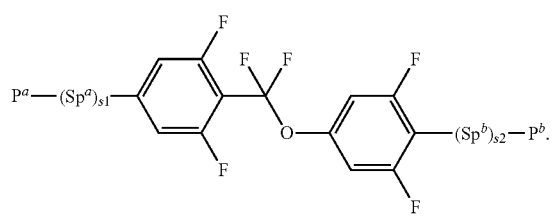

27. A compound according to claim 1, wherein said compound is selected from the following formula:

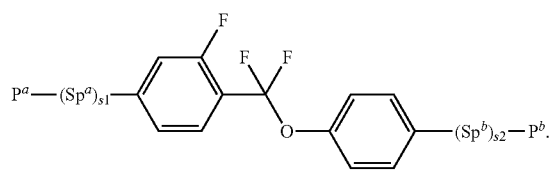

28. A compound according to claim 1, wherein said compound is selected from the following formula:

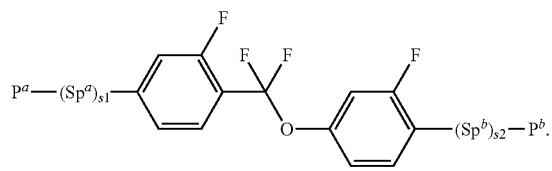

29. A compound according to claim 1, wherein said compound is selected from the following formula:

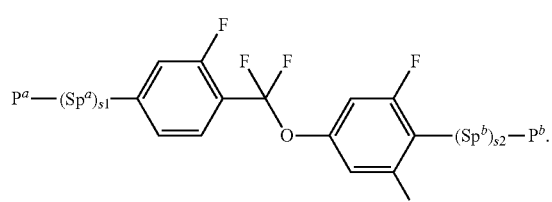

* * * * *